US009957570B2

(12) United States Patent
Mori et al.

(10) Patent No.: US 9,957,570 B2
(45) Date of Patent: May 1, 2018

(54) DNA HYPERMETHYLATION DIAGNOSTIC BIOMARKERS FOR COLORECTAL CANCER

(75) Inventors: Yuriko Mori, Baltimore, MD (US); Stephen Meltzer, Lutherville, MD (US); Ajay Goel, Dallas, TX (US); Clement Boland, Dallas, TX (US)

(73) Assignees: The Johns Hopkins University, Baltimore, MD (US); Baylor Research Institute, Dallas, TX (US)

( * ) Notice: Subject to any disclaimer, the term of this patent is extended or adjusted under 35 U.S.C. 154(b) by 0 days. days.

(21) Appl. No.: 13/876,568

(22) PCT Filed: Oct. 4, 2011

(86) PCT No.: PCT/US2011/054781

§ 371 (c)(1),
(2), (4) Date: Jul. 1, 2013

(87) PCT Pub. No.: WO2012/047899

PCT Pub. Date: Apr. 12, 2012

(65) Prior Publication Data

US 2013/0288247 A1 Oct. 31, 2013

Related U.S. Application Data

(60) Provisional application No. 61/389,304, filed on Oct. 4, 2010, provisional application No. 61/443,562, filed on Feb. 16, 2011.

(51) Int. Cl.
*C12Q 1/68* (2006.01)

(52) U.S. Cl.
CPC ..... *C12Q 1/6886* (2013.01); *C12Q 2600/154* (2013.01); *C12Q 2600/178* (2013.01)

(58) Field of Classification Search
CPC ............ C12Q 1/6886; C12Q 2600/154; C12Q 2600/178
See application file for complete search history.

(56) References Cited

U.S. PATENT DOCUMENTS

2008/0221056 A1 9/2008 Baylin et al.
2009/0047214 A1 2/2009 Esteller
(Continued)

OTHER PUBLICATIONS

Kneip, C. et al. BioTechniques 47(3):737 (Sep. 2009).*
(Continued)

*Primary Examiner* — Diana B Johannsen
(74) *Attorney, Agent, or Firm* — Johns Hopkins Technology Ventures

(57) ABSTRACT

The present invention relates to the field of cancer. More specifically, the present invention relates to the use of biomarkers to detect colorectal cancer. In one aspect, the present invention provides methods for qualifying colorectal cancer status including, but not limited to, diagnosis, prognosis, and risk stratification, in patients. In one embodiment, a method for diagnosing colorectal cancer (CRC) in a patient comprises the steps of (a) collecting a sample from the patient; (b) measuring the methylation levels of one or more biomarkers in the sample collected from the patient; and (c) comparing the methylation levels of the one or more biomarkers with predefined methylation levels of the same biomarkers that correlate to a patient having CRC and predefined methylation levels of the same biomarkers that correlate to a patient not having CRC, wherein a correlation to one of the predefined methylation levels provides the diagnosis.

5 Claims, 20 Drawing Sheets

(56) References Cited

U.S. PATENT DOCUMENTS

2009/0155791 A1 6/2009 Wojdacz et al.
2010/0240068 A1 9/2010 Karl et al.

OTHER PUBLICATIONS

Mori, Y. et al. Endocrine-Related Cancer 18:465 (Jun. 2011).*
Sirnes, S. et al. Epigenetics 6(5):602 (May 2011).*
Balaguer, et al., Cancer Res., Aug. 3, 2010, vol. 70, No. 16, pp. 6609-6618.
Toyota, et al., Can Res., (1999), vol. 59, No. 10, pp. 2307-2312.
Fraga, et al., Trends in Genetics, (2007), vol. 28, No. 8, pp. 413-418.
Kim, et al., Genes, Chromosomes & Cancer, (2006) 45:781-789.
Uhlmann, et al., Electrophoresis, (2002) 23:4072-4079.
Eads, et al., Nucleic Acids Research, (2000) vol. 28, No. 8, pp. e32.
Estecio, et al., Genome Research, (2007) 17:1529-1536.
Mori, et al., Gastroenterology, (2006) 131:797-808.
Toyota, et al., Cancer Res 2008;68(11):4123-32.
Worthley, et al., Oncogene (2009) 29; 1653-1662.
Ahlquist, et al., Molecular Cancer (2008), 7:94.
Belshaw, et al., British Journal of Cancer (2008) 99:136-142.
Menigatti, et al., Oncology Reports, (2007) 17:1421-1427.
Belshaw, et al., Carcinogenesis, (2010) vol. 31 No. 6 pp. 1158-1163.
Svrcek, et al., Gut, (2010), 59:1516e1526.
Nosho, et al., Gastroenterology, (2009) 137:1609-1620.
Weisenberger, et al., Nature Genetics, (2006) vol. 38, No. 7, pp. 787-793.
Shen, et al., Journal of the National Cancer Institute, (2005) vol. 97, No. 18, pp. 1330-1338.

* cited by examiner

TABLE 1 TISSUE DEMOGRAPHIC DATA

| ASSAY | MICROARRAY | | qMSP | | | | | | |
|---|---|---|---|---|---|---|---|---|---|
| TISSUE | NON-NEOPLASTIC | NEOPLASTIC | NON-NEOPLASTIC | | | NEOPLASTIC | | | |
| TYPE / CATEGORIES | CONTROL NC (CRC-FREE, >40 y.o.) | CRC | YOUNG CONTROL NC (CRC-FREE, <40 y.o.) | CONTROL NC (CRC-FREE, ≥40 y.o.) | CRC-NC (CRC PATIENT) | ADENOMA | CRC (ALL) | DUKES AB CRC | DUKES CD CRC |
| TOTAL NUMBER | 8 | 17 | 9 | 26 | 19 | 9 | 51 | 24 | 27 |
| AGE | | | | | | | | | |
| MEAN | 67.5 | 63.2 | 31.2*** | 61.7 | 63.4 | 64.1 | 65.1 | 64.5 | 85.6 |
| s.o. | 8.5 | 10.8 | 7.1 | 12.6 | 8.7 | 8.9 | 11.1 | 13.3 | 9.0 |
| Min-max | 56-77 | 36-80 | 23-39 | 43-80 | 36-75 | 51-77 | 36-87 | 36-87 | 51-81 |
| Gender | | | | | | | | | |
| F | 0(0.0%) | 5(29.4%) | 7(77.8%)** | 2(7.7%) | 4(21.1%) | 0(0.0%) | 11(21.6%) | 6(25.0%) | 5(18.5%) |
| M | 8(100.0%) | 12(70.6%) | 2(22.2%) | 24(92.3%) | 15(78.9%) | 9(100.0%) | 40(78.4%) | 18(75.0%) | 22(81.5%) |
| Site | | | | | | | | | |
| L | 4(50.0%) | 10(58.8%) | 5(55.6%) | 17(65.4%) | 13(68.4%) | 6(66.7%) | 30(58.8%) | 15(62.5%) | 15(55.6%) |
| R | 4(50.0%) | 7(41.2%) | 4(44.4%) | 9(34.6%) | 6(31.6%) | 3(33.3%) | 21(41.2%) | 9(37.5%) | 12(44.4%) |
| Histology | | | | | | | | | |
| WD-WMD | NA | 0(0.0%) | NA | NA | NA | NA | 11(22.4%) | 6(26.1%) | 5(19.2%) |
| MD | NA | 9(60.0%) | NA | NA | NA | NA | 26(53.1%) | 11(47.8%) | 15(57.7%) |
| MPD-PD | NA | 6(40.0%) | NA | NA | NA | NA | 11(22.4%) | 5(21.7%) | 6(23.1%) |
| MUC | NA | 0(0.0%) | NA | NA | NA | NA | 1(2.0%) | 1(4.3%) | 0(0.0%) |
| TA | NA | NA | NA | NA | NA | 6(66.7%) | NA | NA | NA |
| TA+HGD | NA | NA | NA | NA | NA | 1(11.1%) | NA | NA | NA |
| TVA | NA | NA | NA | NA | NA | 2(22.2%) | NA | NA | NA |
| UNK | | 2 | | | | | 2 | 1 | 1 |
| Dukes stage | | | | | | | | | |
| A | NA | 1(5.9%) | NA | NA | NA | NA | 7(13.7%) | 7(29.2%) | NA |
| B | NA | 7(41.2%) | NA | NA | NA | NA | 17(33.3%) | 17(70.8%) | NA |
| C | NA | 6(35.3%) | NA | NA | NA | NA | 17(33.3%) | NA | 17(63.0%) |
| D | NA | 3(17.6%) | NA | NA | NA | NA | 10(19.6%) | NA | 10(37.0%) |
| C/MP | | | | | | | | | |
| + | NA | 5(29.4%) | NA | NA | NA | 0(0.0%) | 5(9.8%) | 2(8.3%) | 3(11.1%) |
| − | NA | 12(70.6%) | NA | NA | NA | 9(100.0%) | 46(90.2%) | 22(91.7%) | 24(88.9%) |
| MSI | | | | | | | | | |
| H | NA | 5(29.4%) | NA | NA | NA | 0(0.0%) | 6(11.8%) | 2(8.3%) | 4(14.8%) |
| L | NA | 4(23.5%) | NA | NA | NA | 0(0.0%) | 5(9.8%) | 4(16.7%) | 1(3.7%) |
| S | NA | 8(47.1%) | NA | NA | NA | 7(100.0%) | 40(78.4%) | 18(75.0%) | 22(81.5%) |
| UNK | | | | | | 2 | | | |

UNK, unknown; NA, not applicable; WD, well differentiated; WMD, well-to moderately differentiated; MD, moderately differentiated; MPD, moderately to poorly differentiated; PD, poorly differentiated; MUC, mucinous adenocarcinoma; TA, tubular adenoma; TVA, tubulovillous adenoma; HGD, high-grade dysplasia. Statistically significant difference relative to control NC in respective assay; *, , *, significant difference from control NCs at P level <0.05, <0.01, and <1×10⁻⁶ respectively. No significant difference was observed between Dukes stage A/B CRCs versus Dukes stage C/D/CRCs for age, gender, tumor site, histological differentiation, or CIMP status. Similarly, no significant difference was observed between CRCs versus adenomas for age, gender, tumor site, or CIMP status.

FIG. 4

Table 2 The ROC curve analysis data for the discrimination from control NCs

| Target tissue | CRC (n=51) | | Dukes AB CRC (n=24) | | Dukes CD CRC (n=27) | | Adenoma (n=9) | | CRC-NC (n=19) | |
|---|---|---|---|---|---|---|---|---|---|---|
| Loci | AUROC: mean (95% CI) | P value | AUROC: mean (95% CI) | P value | AUROC: mean (95% CI) | P value | AUROC: mean (95% CI) | P value | AUROC: mean (95% CI) | P value |
| VSX2 | 0.93 (0.88-0.99) | $<1.0\times10^{-6}$ | 0.94 (0.87-1.00) | $<1.0\times10^{-6}$ | 0.92 (0.85-0.99) | $<1.0\times10^{-6}$ | 0.74 (0.53-0.96) | $1.3\times10^{-2}$ | 0.56 (0.38-0.74) | $2.7\times10^{-1}$ |
| BEND4 | 0.92 (0.86-0.98) | $<1.0\times10^{-6}$ | 0.92 (0.83-1.00) | $<1.0\times10^{-6}$ | 0.92 (0.84-0.99) | $<1.0\times10^{-6}$ | 0.74 (0.52-0.96) | $1.7\times10^{-2}$ | 0.65 (0.48-0.81) | $4.0\times10^{-2}$ |
| ALX3 | 0.90 (0.82-0.97) | $<1.0\times10^{-6}$ | 0.97 (0.93-1.00) | $<1.0\times10^{-6}$ | 0.83 (0.71-0.95) | $<1.0\times10^{-6}$ | 0.57 (0.31-0.82) | $3.0\times10^{-1}$ | 0.78 (0.65-0.92) | $5.1\times10^{-5}$ |
| NPTX1 | 0.87 (0.79-0.95) | $<1.0\times10^{-6}$ | 0.86 (0.75-0.97) | $<1.0\times10^{-6}$ | 0.87 (0.77-0.97) | $<1.0\times10^{-6}$ | 0.76 (0.56-0.96) | $5.2\times10^{-3}$ | 0.61 (0.45-0.77) | $9.1\times10^{-2}$ |
| miR34b | 0.84 (0.75-0.93) | $<1.0\times10^{-6}$ | 0.87 (0.76-0.98) | $<1.0\times10^{-6}$ | 0.81 (0.68-0.94) | $2.2\times10^{-6}$ | 0.76 (0.49-1.00) | $2.8\times10^{-2}$ | 0.47 (0.29-0.65) | $6.4\times10^{-1}$ |
| BTG4 | 0.82 (0.72-0.91) | $<1.0\times10^{-6}$ | 0.85 (0.73-0.97) | $<1.0\times10^{-6}$ | 0.79 (0.66-0.91) | $4.1\times10^{-6}$ | 0.67 (0.42-0.92) | $8.8\times10^{-2}$ | 0.54 (0.36-0.71) | $3.3\times10^{-1}$ |
| GLP1R | 0.81 (0.71-0.90) | $<1.0\times10^{-6}$ | 0.84 (0.72-0.96) | $<1.0\times10^{-6}$ | 0.78 (0.65-0.91) | $1.3\times10^{-5}$ | 0.61 (0.39-0.84) | $1.7\times10^{-1}$ | 0.55 (0.37-0.72) | $2.9\times10^{-1}$ |
| HOMER2 | 0.77 (0.68-0.86) | $<1.0\times10^{-6}$ | 0.75 (0.62-0.87) | $6.2\times10^{-5}$ | 0.79 (0.67-0.90) | $<1.0\times10^{-5}$ | 0.83 (0.66-1.00) | $7.2\times10^{-5}$ | 0.57 (0.43-0.70) | $1.7\times10^{-1}$ |
| ZNF583 | 0.69 (0.62-0.76) | $<1.0\times10^{-6}$ | 0.70 (0.59-0.80) | $8.5\times10^{-5}$ | 0.68 (0.58-0.78) | $1.2\times10^{-4}$ | 0.56 (0.45-0.66) | $1.6\times10^{-1}$ | 0.58 (0.49-0.56) | $3.3\times10^{-2}$ |
| GJC1 | 0.66 (0.54-0.78) | $5.0\times10^{-3}$ | 0.72 (0.58-0.87) | $1.5\times10^{-3}$ | 0.60 (0.44-0.76) | $1.1\times10^{-1}$ | 0.38 (0.16-0.59) | $1.3\times10^{-1}$ | 0.55 (0.38-0.72) | $2.9\times10^{-1}$ |
| DOCK8 | 0.59 (0.49-0.68) | $4.0\times10^{-2}$ | 0.55 (0.43-0.67) | $1.9\times10^{-1}$ | 0.62 (0.50-0.74) | $2.7\times10^{-2}$ | 0.47 (0.35-0.59) | $3.1\times10^{-1}$ | 0.42 (0.35-0.49) | $9.8\times10^{-1}$ |

CI, Confidence interval. The ROC curve analysis results are shown for the detection of respective tissue class from control NCs. Mean AUROC and 95% CI are shown as well as the P values corresponds to the comparison to non-discriminative curve.

FIG. 5

| Biomarker | Forward Primer Sequence (5'>3') | Reverse Primer Sequence (5'>3') | TaqMan Probe Sequence (5'>3') |
|---|---|---|---|
| ALX3 | GTTCGGGTTAGCGTTAATTCGGTTTTC (SEQ ID NO:1) | CTTCCTACTTATCTCTCCCGCTCG (SEQ ID NO:2) | AAGTCGTGGCGAAAGGCGAGAG (SEQ ID NO:3) |
| CCDC4 | TTTTGCGTTTGGAATTGTTGCGGC (SEQ ID NO:4) | CCTAATAAAACTACCGCACGTACGAACG (SEQ ID NO:5) | TTCGTTGTTGTTGATGGAGACGGCG (SEQ ID NO:6) |
| CHX10 | AAAATTTTCGGATTCGGGTTTCGGC (SEQ ID NO:7) | CAAAAAACCTACGAACGCCCG (SEQ ID NO:8) | ACCGTCCCATCCCTAAACTCAAACTAACC (SEQ ID NO:9) |
| DOCK8 | GGTTTCGGGTAGAGCGCGTC (SEQ ID NO:10) | TAACGCGAAACAACGACGAACG (SEQ ID NO:11) | AGTATCGGGAGGTTAGTTTCGCGTTGG (SEQ ID NO:12) |
| GJA7 | TTCGGGTAGTTGTCGGTATCGTC (SEQ ID NO:13) | CGCGAAAATATCGAACGACGATCG (SEQ ID NO:14) | AAACGACGCGCACTCGACGAC (SEQ ID NO:15) |
| GLP1R | AGTTCGGGATTAGTTTTCGTACGC (SEQ ID NO:16) | AACCGAAAACGCCGACCATAACG (SEQ ID NO:17) | TCGTAGGTGGTAGCGATGGTTTAGTTTTGA (SEQ ID NO:18) |
| HOMER2 | GGAAGGGTTACGGGTTTCGC (SEQ ID NO:19) | CGAAAATCTAAAACCACCTAACCCGCG (SEQ ID NO:20) | TTTGTTGGGTGTTCGCGTGTTTCGG (SEQ ID NO:21) |
| BTG4 | ATTCGTTTCGTTTCGCGTTCGTTTC (SEQ ID NO:22) | CGGGAGGGTTTTGAGAGGAGC (SEQ ID NO:23) | AACGACCAACCGTCCTTAAAACCC (SEQ ID NO:24) |
| miR34b | CGCTCTAAACGACCGAATAACTATAA CG (SEQ ID NO:25) | CTCCCAAACCGAAAACCGCG (SEQ ID NO:26) | TACCAAACCTCCCCTTCCCGCAAC (SEQ ID NO:27) |
| NME4 | GTTTCGGGTTGGTATCGTTTTTCGC (SEQ ID NO:28) | CGCCAAAAAAAACCGCCCATAACG (SEQ ID NO:29) | TTTCGCGTTTATAGCGGTTCGCGG (SEQ ID NO:30) |
| NPTX1 | AGTTTTCGAGCGTTCGTCGTTTGC (SEQ ID NO:31) | TCTAACGCCAAAAAACGACGACCG (SEQ ID NO:32) | TGAGTCGGGGTTGCGTTTTCGTTG (SEQ ID NO:33) |
| TMEM42 | GTAGGGCGTCGTCGTATTTTCGTC (SEQ ID NO:34) | TACCACCCCAACTAACCGCAACG (SEQ ID NO:35) | TTTGTTTCGTCGGGGTTTCGGGTCG (SEQ ID NO:36) |
| TTLL12 | GCGTTTGTGGTTTGGTTGTCGTC (SEQ ID NO:37) | TCCCGACATTCCCCGAAATCG (SEQ ID NO:38) | TGCGTACGCGTATTTGATGGTGGTTGA (SEQ ID NO:39) |
| ZNF583 | GATTTGCGGTCGTTCGGGGTTTTC (SEQ ID NO:40) | AACCCTAAAACAAACCGCAAAAACCG (SEQ ID NO:41) | TTTGCGTCGCGTCGGTTTCGGATTT (SEQ ID NO:42) |

FIG. 6

| Locus | p-value | CRC mean /NC mean | p-value<0.01 and fold change>0.5 | CRC min.> NC max. | REFERENCE |
|---|---|---|---|---|---|
| BMP3 | 2E-02 | 0.38 | no | no | (Zou, et al. 2007) |
| GATA4 | 9E-03 | 0.91 | yes | no | (Hellebrekers, et al. 2009) |
| GATA5 | 5E-05 | 1.04 | yes | no | (Hellebrekers, et al. 2009) |
| HIC1 | 9E-06 | 1.16 | yes | no | (Lenhard, et al. 2005) |
| HPP1 | 1E-06 | 2.90 | yes | no | (Belshaw, et al. 2004) |
| ITGA4 | 1E-05 | 0.56 | yes | no | (Ausch, et al. 2009) |
| MAL | 7E-03 | 0.93 | yes | no | (Mori, et al. 2006) |
| MGMT | 7E-02 | 0.49 | no | no | (Belshaw, et al. 2004) |
| NDRG4 | 6E-02 | 0.08 | no | no | (Melotte, et al. 2009) |
| NELL1 | 1E-04 | 1.65 | yes | no | (Mori, et al. 2006) |
| OSMR | 4E-04 | 1.15 | yes | no | (Kim, et al. 2009) |
| RASSF2 | 9E-07 | 1.26 | yes | no | (Nagasaka, et al. 2009) |
| SFRP2 | 1E-12 | 4.10 | yes | yes | (Muller, et al. 2004) |
| TFPI2 | 2E-07 | 2.98 | yes | no | (Glockner, et al. 2009) |
| VIM | 5E-03 | 0.35 | yes | no | (Chen, et al. 2005) |
| WIF1 | 1E-01 | 0.93 | no | no | (Lee, et al. 2009) |

APC, SEPT9, AND ALX4 LOCI WERE NOT INFORMATIVE IN THE CURRENT MCAM ANALYSIS.

Supplementary Table 2 MCAM-derived methylation profiles of the previously reported CRC methylation markers.

FIG. 7

| Locus | | | Microarray (Log2 intensity) | | | | MSP |
|---|---|---|---|---|---|---|---|
| Nucleotide position (hg18) | Corresponding genes | Location | CRC: mean (SD) | NC: mean (SD) | CRC/NC | t-test p-value | Hypermethylation in CRCs |
| chr4:154929653-154930045 | SFRP2 | 5'UTR-Exon1 | 1.37 (1.10) | -2.72 (0.35) | 4.10 | 1E-12 | (+) |
| chr14:73777277-73777554 | VSX2 | Intron1 | 1.57 (1.19) | -1.77 (0.45) | 3.34 | 8E-10 | (+) |
| chr6:41714264-41714529 | MDFI | Exon1-Intron1 | 1.89 (0.95) | -1.33 (0.37) | 3.23 | 1E-11 | (+) |
| chr4:154930045-154930197 | SFRP2 | 5'UTR-Exon1 | 1.82 (1.14) | -1.22 (0.20) | 3.04 | 1E-09 | (+) |
| chr1:110414310-110414409 | ALX3 | Intron1 | 1.58 (1.00) | -0.94 (0.12) | 2.52 | 3E-09 | (+) |
| chr17:76066388-76066727 | NPTX1 | 5'UTR | 1.48 (0.52) | -0.39 (0.19) | 1.87 | 3E-12 | (+) |
| chr6:39124527-39124750 | GLP1R | 5'UTR-Intron1 | 0.79 (0.55) | -0.75 (0.24) | 1.54 | 1E-09 | (+) |
| chr3:44878617-44878768 | TMEM42/miR564 | Intron1 | 1.09 (0.18) | -0.16 (0.40) | 1.26 | 6E-12 | (+) |
| chr22:37432155-37432530 | GTPBP1 | Intron1 | 0.62 (0.18) | -0.51 (0.22) | 1.13 | 1E-14 | (-) |
| chr11:110888513-110888739 | miR34b-BTG4 | 5'UTR | 0.62 (0.32) | -0.42 (0.22) | 1.04 | 3E-10 | (+) |
| chr15:81412032-81412142 | HOMER2 | Intron1 | 0.71 (0.37) | -0.28 (0.23) | 1.00 | 8E-09 | (+) |
| chr22:41912965-41913471 | TTLL12 | 5'UTR-Intron1 | 0.31 (0.21) | -0.65 (0.21) | 0.96 | 3E-12 | (+) |
| chr11:67985025-67985286 | SAPS3 | Intron1 | 0.55 (0.29) | -0.28 (0.13) | 0.84 | 6E-10 | (-) |
| chr1:154988383-154990056 | HDGF | 5'UTR-Intron1 | 0.45 (0.15) | -0.36 (0.17) | 0.82 | 1E-13 | (-) |
| chr19:3012272-3012428 | AES | Intron1 | 0.30 (0.19) | -0.48 (0.18) | 0.78 | 1E-11 | (-) |
| chr16:387138-387279 | NME4 | 5'UTR-Exon1 | 0.37 (0.21) | -0.39 (0.10) | 0.76 | 5E-12 | (+) |
| chr9:204673-204810 | DOCK8 | 5'UTR | 0.37 (0.23) | -0.36 (0.10) | 0.73 | 8E-11 | (+) |
| chr19:61607426-61607563 | ZNF583 | 5'UTR-Exon1 | -0.03 (0.19) | -0.65 (0.14) | 0.62 | 4E-10 | (+) |
| chr17:40262574-40262867 | GJC1 | Intron1 | -0.32 (0.19) | -0.29 (0.11) | 0.61 | 1E-10 | (+) |
| chr4:41848650-41849315 | BEND4 | Intron1-Exon2 | 0.03 (0.13) | -0.56 (0.09) | 0.58 | 2E-13 | (+) |

Supplementary Table 3 Preliminary validation results of the twenty candidate loci for cancer-specific hypermethylation.

FIG. 8

ALX3 (SEQ ID NO:54)

>chr1:110411689-110414926
TCCCTACCAGCGGCTGCTTCTAAGCCACTGTGCAGCCAGGAAGCAGCGCCGCAGCAGGCCCGAGTGCTCCACTGT
CCCCACAGAAGGCATCCATTGAGACCGCGGGACCAGCCTTGGCTTTCACATTTCGCTGCAGCCTTGTCCCGCGCC
GCACTGTTTCCTCCGGCCACTGTGGGGTCACTAAGCGACCTGCAGAACTCGCTGAGGCCCAGGCTCCTGCAGCTC
CCGCCGAAGACTCAAAGCCAGAGTGGACATAAACGCCGTGGGCAGGACCCCGGTGAGGCCTCGGTGCCCTTCTTG
GGGGTTCTCAGCGTTGGCCCAGAAGCCTCAGCCCGGGTCTAAGAACTTGGGACTCTCCTCGACTTTGGCGATCGG
CCGGGTCATCCGGCTCAGGGCCTCAGCGGCAGCGGGCAAAACTCTAGTAGGAGTCTCTTGCCGAGGGCGTGTTTC
GACGTCAGAGCCAAACTCGGGACAGACTAGCCAAGCGCGGACGGCGCGAGAGTGGCTGGCAGCGCCAGCACGCAG
CCTGGGTTCAGAGCAAGGCTGGGCGCTCTCAGCAAAGGGCGGCCTGGGGCTGCGCGGGCGGCGGACTGCAGGCGG
GAGAAGAGCGAGGTGCGCCAGGCTCTGGGGCGCGCAACTGCCCAGCCTCGTGAAAGATCGCGCCGCAGATGGGGC
GCAGCTGCGCGCTCACTCGTGTGGACTGGAAACGCTCCCGAGCCGGTTATTTTAAAAACCGGGAAATAAGGCGGGT
TCCCTCTTCGCCCGCCACTTCCCACCAAGTAGGCTGTGCGGCCCTGGGGGCTGACTGTCCTCAAGCAGCCAGGCT
CCACCGCGCGCCGCGCTGCGCCGAGGTCCGCTCTGCCGCAGGGACGCTGGCAGCCCGTTGAACACCGGCAAGAGC
GCCAGAGGCTAGCGGCCGCCAGGATCTCTACCAGGCTCTGCTCGCACCCGCCTGCCTCCCTTTCGTTTGGCCTGT
CCTCCGTTCAACTGAAATCGTTAATTTTCTTACCCCCTTGTTCTCATTTTGATATATTCTACGCTTTAAACATGC
TCCGTTTTCTTTTGTTTAGTCTGCTCCCTCCCTCTTTGTCCTTTCCCCCTTCTCTAGTTATCCGTTTCGTTCGAT
CTTGCTCCTGCTTTTTTTATTCGTTCGTTCCTCATTTATTCATTTTAGTTCATCCCAGCTCGCCGACTGCCATTT
ACCCTCTCGTTCTCGCCGCGCTCTCCGTTGTTTTGTTCAATTTCCCTTCCCCTTTTCTTGGTTGTCGCTCGCTTT
CTTTGGTTTTCTTTCTCGGTATTTCGTTGTCAAGGCCACCCTTGCCCTCGGATCCCGGGGTGCTGGGTTTCTCCC
GGCCGCTCGTTCCGCACCAGCGCTCTCTGCAGTTCGCGCGGCACCGGTGTGGTCCGGGGGCCCGAGCTGTCGGTG
CCGGATGCGGCGCGCCTAGCAGGGACGCGGGCCTGGGGGGGTGGCTCCTGCCCGACGCGGAGCGCTGAGCCAGGC
CGGGTACCTGTCTCTGGCGGTGCTCACCGCACTGCGCGGCCTCTGCCGTCTGGCTGGGATCAGAGGAGCCAGGCC
AACTGCTTCTCATTAAGTCCCAACTGTGGTTTTTATCAGGAAAGCCTCTTTCAAAGGGCACAGACACGAAGCTCC
GCGGACTCGTTCATTTCCTCCGTTGACCCACACACACCTCCCCGCCCTCCCCTACACATTCCCACCGCCCCCGCT
GGGCGAAAGCCGGAGATGCCCGGCCACTCCGTGGAGGCCCGCGAGGCGCCAGCCGGGCGGCGGCAGGGGGTTGAG
GCGGATCTTGGAGGATCCAGTTCTGGGCCTAGGCTGCGGGATATGGCAGCGCAGATAAGGTGGGTGCAGTGCGGA
AGCCGAGACGCCTTACAGGTCATAGGGTGCGGCGGACGGCCGCAGAGCTGCCGATCAGCCTGCCAGGCCCCTGCC
TTCAGGCGCATTCTCGGATGCCGGCGCGGTCCAGCCGGCCTTAGCACAGGGCACCCGCCCCGTGAGCCCCGCCGC
CAGGGGGTTAGGCTGCCCAGGGCTGCTCCTGACTGCCCAGCGGTGATGATCCAGCGCGGGGAAGCCAAGACTGCC
AGAAGGGCGGCTATCATAGTGCATAACGGCAGGGAGGCCAGCTTAGTATGAGAAATAAGAATACAGTTATTCCGT
CTTGAGGACAGCCCTGGCATTGCACGACCAGTCGCGGCCAGACTGTGCCAGTCTGCCGCACAGGCAGCACCCTTC
CTGTGAAGGCTAGGCCCGGGGAGGAGAGACGGGCCAAGACCAGGCCGCAGTCCCCAGCCGACCCCGATTTGACCA
CTCTAGGTTGAGGCCCAGCCTCAGGGCCCTCAAAGGGCGCCAGACACAAAAGCCGCGCTTCTTCGTCAGGTCTCA
GTGTGGCTCCACAGCCCTCGGCCGGGTCTGGGCTTCAGGGTAGGTGGCAGTTCCAGTCCAACTTCGGCAGAGCAT
GCTCTCTCCTTCCCAGGTCCAACTGCTTTCGGGCCCCGACTGGACTCCGGGCCGTCGCCACTGCACCTTCCCTCG
ACCTCCCGCCTTCCATTCCCGCCGCCGAGGAACGGTGGTTCACCCTCCCGCCCCACACTGGCCTTTGCCTGGCCC
GGGCCAGCGCCAACCCGGCTTCCGTGGAAGCCGTGGCGAAAGGCGAGAGGGGCAAAAAGTTGAGAAATAGGCGAG
CGGGAGAGATAAGCAGGAAGGCCCGGGTGGGCCCCGGGTAAGGAAGAAGAAGAGAGGGTCGGGCTGCGCCTACGC
CCCGCGCCCGCGGTTAC*CTTCCGCGGGGCCCTCGTAGAAGTGGCCGCCGTTGAGGGCCGGGCCGGCCCCGAGGTC*
*CTGCAGGTACTTGGCGGGCGGCTTGGCCGGCTCTGGGAGGTAGGGCTCCAGGGGCCCGCAGGCCGGAAAGCGGGT*
*CAGCCGCGGGCCGCGGGGCGGCGCGGGGTGCAGGTGAGGCGCAGCGGCGGGGGTTCCCTGCCGGCCCCGAGGCTC*
*GTCCCCCGAGGCCACATAGGGGCCGGGTGCAGGCCCCACGCGGAAAGGCGCGCAGTGCTCGGGGTCCATGCCGGC*
*TCAGGCGCACAGGCCTCCGGGGCTCCGGGGCTCGCGCTGCCCGCGCCCGCCTGTGAGCGCCCGCCAAGGGGGAGG*
*GACCTGG*GCGCGGGGGCGCCGGAGCCCCCGGGAGCGGCGCGCGCCCGCGGGGGCGGGGGCGGGGGCAGGGGAGG
GGGCCGCGCCTCT

FIG. 14

VSX2 (SEQ ID NO:55)

>chr14:73775842-73778045
tAGtTtTGAttttAtTTGGGtTGtCGttTGGTTGGATAAAAGGGGAATtTttTTGGGtTttAGAGtATTAGAtAt
CGGAGGGGGtAttTGGGAttAAtTTCGCGAAGCGGGAAGttCGGCGGGGGGGTGGGGGGAGtTAAAGAttTGCGG
ttTtAGttttTttAAAGAAtAGGGAGATGACGGGGAAAGtAGGGGAAGCGtTGAGtAAGtttAAATtCGAGAtAG
TGGttAAGAGTAttTCGGGGGGCGtttCGGttAGGTGtAtTGGGTTCGGtATttAGGAGATttTGGGtTTGAAtA
AGGAGttttCGAGtTtttAttCGCGGGtAGCGtTCGACGGttTGGttttCGGGtAtTTGtTGGCGGCGCGtTtAG
TGtTtAGtttCGCGGGGGTGGGCGGtATGGGGtTTtTGGGGttCGGGGGGtTtttTGGtTTtTAtACGtAGtttA
ttTTttTGGAAGTGtTGTtCGAttCGtAGAGCGTttAtTTGtAGttATTGGGtAGAGtATCGGGGtCGtTGGAtA
ttAGttAGACGGttAGtTCGGGTAGGTGAGGAGAGGTTGCGtTGtTGttTGAtTGGGGGGCGAtAGtCGGGAGtt
tCGCGtCGTCGGtTtTCGtTTGtTGGAttAGGttTttAGGCGGAAAAGTTttTGttAGGtCGGGGGTCGtCGttT
GGGttTTGGGtCGACGCGttTGGTGATGGGGttCGGGAGGATGtTTCGGCGTtCGtAGGGTTTCGGtttAAGCG
TTTCGGGCGGtCGCGtAGTTtTttAGTtttCGCGTCGGGtAGGGtTCGGttACGGtAtTtTGTTGGAGttttAtT
GAAAAtTGGGTTTGGGGTGTCGGAGttCGTGGTGtAGAGTCGtCGGtCGTGTCGGAGGGttttAGtAtCGtTGtT
ttAtTGCGGtttCGGttTGGTGTAGGATtCGtAtTttTCGAGttCGATGtTGTTtCGGtTtCGGtttATttttTG
GTGTttAAAGTTGTtTGATTttAAATttCGCGtTGGTtAAtTGGGGTTTATTTTTtAttttACGAGtTtAGAt
AAttCGGttATCGCGGtAGtTAAAGCGGtCGttATttTtTtttACGTAAGCGttAtTATATAtTGGAGtCGGG
ACGCGCGGGtTCGGGGAtttTGGGTGAttTtTtCGttTTtTtttCGCGtTGtTTTtCGGGAGGTGTGTCGCGGtt
CGtTCGAAttTtCGATTttTGTTTGAGtTTGGtAATTttttCGATTTTTCGTTGCGTTTTAtTTTGTTTTACGTG
GAAAGGtAACGAAAAttAGCGCGTCGtAGGtTtTCGGGttTCGAGTAGGGACGtATTGTGtCGttTTGCGAAAAG
GACGGTGtTCGGtAGttttAGTtTTttCGGAGtttAGtTttttACGttTtCGtTtCGtTttTCGtTttTCGAGG
ttAAtTTTtCGGttCGGGGtATTGGGGtTGGtCGCGtAGGGtAGGGCGtAGtAGGGTCGCGAGCGtTGtCGGGGA
TtTtTGCGGttttTAAGGtTGttTCGtTtTtCGTCGTttCGGTtttAAGCGCGtCGGGGttTTTGttTtTtTTA
tAACGAAATtTGTTtAAAAttTtCGGATTCGGGtttCGGCGCGGGAGAGGTtAGttTGAGtTtAGGGATGGGACG
GttAtCGGGGCGttCGtAGGtTTttTGGGGAGAtAGAGtAGGTtttCGtCGtTCGCGGAGGtAGttCGGGGTGGG
GtttTCGCGGGTTTCGGGtAtAGCGGAGCGCGTtttttAtTtTGtCGtATGTttttTACGttCGtTTTTtAGATTt
TGAAGATGTTTttTttAGCGATCGAAAAATGTttAAATtTGtTTTAAAttAGAttAAGAAACGGAAGAAGCGGCG
AtAtAGGTGAGGttttCGtTTTtTGTTAttTtTttTGttCGCGtAtttCGtTGtCGTttttCGTTtCGGGATCGG
GTtTtTCGGAtttTATTTTCGtCGAtAACGGATtTGAGGTtCGAGGtCGTGttAGGGCGtAGAttACGGGTTGTT
TGGCGGAATtTGttCGGGGGttTTGGCGTCGGtAtCGGTTGAGtAGGATGAGTGGtCGtCGGGAAAGCGGttCGG
TTCGGGtTTTtTttTttTTGTTtAGGAGAAAGGAAAGGtTttAAtAtAGGttAAAtTGAGttAtAGAGTGGGGGC
CGTttttAGATttCGtAttAGTAtATTt

FIG. 15

NPTX1 (SEQ ID NO:56)

>chr17:76064003-76067478

CTCCAGGGTGTTCACCCGGGACAGCACCTGCCTCTCCAGCTCATCGATCTTGCTCTGCAGCAGATCCTTGAGGCT
GTTGGTCTGGCTGGAGGAATTGAGGCGGCTGTACTGCTGCGGGGTGCAAGGGCGGGGGAAACCACACCGTTAGGC
GAGGCGCGGGGACCGTGCTGGAAGGCCCGCGGCGCGGTCCCCTCTGGGCGACTGCGGGGGCGGCCTGGCAGGGAG
CTGGGGCGAGTGGCCGCCGCGGGGCCTCGCAGGCGCGGGGAGGCACCGGCCCGGCACCCGCGCGGCTGAGGCGAG
GGCGGGGGATGCCTGGCCGGGTAGGGAACGGGGTGGGGGAGGGCAGAGGGGCGAGCGAGCCGGAGGGGGAACCGG
AGCCGAGGGCGCGCGGACCTCGAGGTTCTCCAGGCGGGTTTTGAGCGATTGCAAAGTTTGCCCGAGTTGGCTG
AGCGTCTCGGCGGCCGGTGTCCGGGACAGGTCGCCCATGGTGTTCTTGCCCGAGCCGGGCTGCTTGCGGCCGCCG
CCCGCCCGGGCCTCGCCGGCTCCGGGGTCCAGCGTGCTCTGGCTCTCGCAGCGGCCCAGCTTGGCGGTCAGCTCG
CGGATGGTCTCCTTCTGGCTCAGGATGGTCTCCTTCTGCTGCAGCACCGTCTCGCGGAGCTGCAGCACGCTGCTC
CGGAGCTCCTCGGCGCCGCCGGCGGCCACCGACGCGGCGCACATGTCGGCGTCCACGGGCACCGAGGTGCAGATG
AAGCGCGTCGGCCCGAAATCCTGGGCCCCGGCGCCCAGGAGGCAGAGGCGAGCAGCGCACAGGTGCGCGCGGCG
CGGCCGGCCGGCATGGCTGCGGGCACCGGGCGCTCCGGGCCCGGCTCGGCTCGGCTGGGGCTCGGCTCCGGCTGG
GACCCGGCTCGGGCTGTGGCTCCGCGAGCGGCCCGCGCTCTGGGCGCCGCGCTCTTCGGCCGCGCGGTCCACACC
GCCGCGCTATCAGGCCCCCACTGCCGCCTGCGCTGCGGAGCCCGCGCCTTTTATGCCGCCGCGGGAGGGGCCTCG
AGCCGCCGACGTCAGCGGGGGAGGAATCCCGCTTTAATTGTCCGCGGCCCGGCCCGCGGCGCGGCGGGGGTCTC
ACGAGCGCGCCACCGGGGCTGCCTCCGCTCGCGTCCCCCCCGCCCTTCTGGGAGCTGCCGCGGCCCCCTCCTCCC
CCGCCCCCGCCTGGGCCGGCGCTGCTGCCCCGAAGGCTCCGAGAGCTCAGGGGGAAGGAAGTCGGGCTCCGGCCC
CGGACTCCAGGATGGACCACCTGCGTGGTGTCCCCGAACCTCCGACGGGGCTCCAGGCGGGCGGGAAACCACCGC
GTCCGGGAGATAGAATTCGGTTCGGCCCTCCTGGCTGCACTGAACACCCTTGGGCCGGGGTCGTTTGGAGCCGGG
CTGGGTGCCCAAGGACCCAGGTCGTCAACACCCGAGTGCCCGGTGGTCAACGGCTCGGAGTGGGGCCTCGCCGCG
CCACTAAGTCCAGAGCGGGGGTCACCGGGCCGCCCCCGCGTTTCTTAGATGTCCGTGTGCTATTGAGAAGCCGCCG
GGCAGCCTGGGTACAGGGACTTCCCACGGGTCGGGGCCCCCGGCGCCTCCCCTCCCCCAGCTCCCGGGCTCTGTG
GACCCGGCCCCGTCCCCGGGGGACTGTCAGTCCCCACCCCGTGCGGGCGGGGCGCTGGGGACTTCTCGGAGGCAG
ACCTAGCTGATCGAGCCTTTCCTGTCCGCGGCGCCGGCCCGATCGCCGGCAGGCGGCGTCGCCCGGGCTGGACGT
TCGCAGCGGCGCTTCGGAAGGGGGCCCCGCGGGAGCAGCCGCCCGCGTCTCCAGCAGCTTCCCCTTGCCAGGCGC
CGCGCGCGCCCGGTATCCCCGGGTGTCCACCTGTGCGTGGGGGGCTGTTTCCCGTCTGTCCAGCCGCGCCCACTT
CTCAGGCCCAAAGGCCAGCAGGAAGGGTCCCGGAGGTGGCTGGGGGCGTCCACCTGAGAAGCTCCGCTCTCGCTC
AGACACCCCACCCGGCACCGGCGCACTCGGCGCCTTCATCTGGACCGCGGGGCTCGGCTCCCGAGATCGCGGTCCG
GGTTCCGGCGCCGGGCTGGGGGCTCAGGACCAGGGCTGGCGCAGCCGCCCCGCCCCGCCCCGCCCCGGGGCTATC
AGAGCGGTCAAAGCCTCGGAAATCCCTCCGTCCACGCTCCCGTGGTACAGAGAAGGAAACTGAGGCTCCGAGACT
GCGGGGCCGGGCTACAGCCGTGGCCCCCCGACCCCTCCCCGCCGCCCCCGGCTTCTCTGGTCTCTGCGTTCTGCA
GCCTTTCCCTGCGCGCAGCCGGGGGCTGGGGGTCCCCAGCCAGCAGGGACCCACGGGCAGTCCCGGTGCCGGA
TCGGCTCCCCCCTCGGCGGAGCAGAGGCCGCTCATGGAGACCTTTTTGAGAAATGGCGCCTCTACCC
CCCCCCCAGCCCCCAGCCCCCCTCTGCTTCAGCATCTCAGCTTTTAAGCCTCCCTGAGCCGGGCTGCT
TCTCTTGTCTCCTTCGCCCCCTTCCTGGCCCAGAGGGACCCCCCGCCCCACGGCCTGTCCTCGCTC
CCCTCGAGGGTGTGCGGTTCCCCTCCCTGGCCCCCTTGCCCACCACGCCCCCCAAACCCACCCGCCC
CCGCCCCTTGCTGCTCTGCCACCCCGGCCGCAGGAGGGGTTAGCCTCGCCGGTCCCCACGCGGGGTCTGCG
CCGGCAGCGCCACGGGCTGGAACGCGCCTCGGGAGAAATTACCCGCGCGGGGTCGCGGCGTCTTCTGCCCCAACT
CCCGTAGGGAGCCGCTAGGCGGGTGCCCTCCTGGCCCCAGCGCTTTGGCCTCGCCGCCCTCCCGCACGCGTCCAG
TGGGAGGCCGCGCCCGTCAGGCCTGGAGCCGGACCGTGCCCAGCCGAGAGCGCGCGGCGCCGGAGAGGAGCCC
TGCCCTGCCCAGGGCAGGCTGTTTAGACGGGGCGGGAACCCTTAGCCTGGCCCCGCGTCTCTATCCCCAGCAGCC
GTGGAGCCTTCCTAGCCGCCCAAGGCCAGGGACCCTGCCTGGCTTTTCCTCCAGGGCAGCAGATCTCAGCGGCCT
GGCACCTCGGCACAGAGGAGCGTGTCCCCCTTCCGCAGAGGAAGGGAGTGGACGGCGTCAGAAAGGGAGGGGAGC
CTGGGGCGGTGTCTGGGGCTAGCGGGACCTCTGGGCACTGTGGGGCCCCAGGAGAGGAGACCCTCGGGTCCAGCC
TGCAACTGTTGTGCAGGAGGCGCTGGGCGGGACACCTGCAGGCGCTGCACACACACGCGAGGGCCACCATGCCGC
GTTTCTCCTTCACAAGACCCTGGGCAAGCGGAGGGTCGTATTTAGGATTCCCTCGGCCTCCCCAGTGTTCTGAAA
GTATCTGAGAGGGAGGGAGCAGGAAA

FIG. 16

BEND4 (SEQ ID NO:57)

>chr4:41847424-41849841
ACTGGGAGCTGGTGGAGAGGTCCCTTGGGCGCAGGCCTCAGGCTGTGGCCTCGCAACCAGCCCATCTCGCTCCCT
GCAGGCAGGCAGTGGGCTGCTTTGCCGGGCAGCGCCCGCAGACTCGAGATAAAGGAGAGGAGTCGCGGACCCCAG
AGTGGGTGCCTCCCACGAGGCGTTTCTGTAAGGCTCGGGCCGAGATGCTCGGGAGGGGCAGGACCCCGCCGCGCG
GCAGCGTGCCACGGACGGGGACGAGGGGATGGCGGGGACGACGACGTGGGCGGTGGGAGCAGAGTGCCTGCGACT
CCCGGGGCAGGAAGGAGGGGCGGGATGGTTCCCCGCGCCCGAAATCCACGGCGTGGCGGACGCGGAGGAGCCCCG
AGTCTCACAACCAAGGGGTGGGAAGGAAAAGGGACAGAGCGAGACAGAGCGCCCCCGAGAAACACAGGCGCACAA
AAAAAGACAGAAGGAAAAACGGAACTGAGAGCCAGCCAGCATGGACTGCGACAGCGTGAGAGTGCATCAAAGAGG
TGGCGAAGAAAGCACTAGAAGGCAAAGGAGAAGTGGAGAGAAGAAGAAACAAATGGAGGAAGAAGGAGAAAGGGA
AAAAGCAGACGGAAAAAGTGAAGTAGTACGAGGGCGTCCCAGCGGGGCGGCCCGAGAAGCTCCAGCTTCTTCCCG
AGCGGCCGCCGCTATCCCCCGGGGGGGCGTCTGGCCCCACTCCGGACCACGCCCGAGCGATCCTGGTCGCCGACT
GCCACAGCCGTGCTTCCCGGCGCGGGATCCAAGCCGCGGAGCCACCTGTTAGGCGCGCGCCCGTCGGAAGCCCAGG
CGCGGCGGCGCTGGAGAATCCTCTCGAAGTTTCCGGGTGCGCGGGGAGGCCCCAGGTGCGCCCCGACATCCCGAC
ACGGCCCAGCACGGGTAAGTGTCGGCGGCCCCCCGCTTCTCCTTCCTGGGTCCCCTCCCGCTGCCCCCGGCCGTG
GCGGGAAGGAAAGTTGTGCGGAGAGTTGGTACCTGCGCTGAGCTCCAGGCTGGCGCTGTCGCTACCCGTGCCGCC
CGTGCCGGCGGCCGCCGCCGCGCCTGGGCCATACCTGACGACAGCGGCCAACGAAGACGACGAGGAGGCGGCCGG
GGACGCGGGCGGCGGCTGCGCCGGAGTCCTCAAGTGGCCCTGGGATGTGGCGGGCGTGCAGGACGGCGACGACGA
CGAAGCGGCGGCGGCGGCCCGGCCGGGCC GGGGGGTAGGAGCTCTG CCTGGAACTGCTG G G GCT
CTGCTGCTGATGGAGA G G TG G AAGGG G GGGG G GGGG CC CA TG GCAG
CTCCACCAGGGTGGGT CT TAG CTTGGCCAG C GTCTCTTGCTGGGGAA TCTTGAGGA CTGTA
GGGGCTG CTGCTTGTAGATTTTGGGGA CTGGGCCCCTCCTCTGC GCTGCATCTCTTCCTCCATC G
CCT GGGC GTCCCT GAGCA TCCCCTCCC C GG C GGCTC AGGGTGCCTC C CCTGCC
C GGTCTGCCCTGGTG TGTGGGAGGGTGTGTGTCTGTGC TGGC C C C C CCTGT
CTGAGGCTGGCAT C AGCCCC GGGGGCTGC CC AGCTCCTGATTGACAGGCTGCCT CCAAT
GCCTGGAGGGAGAAAGGAGGTAAAGAGCAAGTGTTTAGGGTAATATCTGCTAATGATAATGGGGG GGG GGG
CCTGG C CAGC CC GGGTCTGCCTGG GCTC CCTC A GGGAG GGGGAAGGGGGAAAG
AGGACCTGGAGGA CC GGAACTGGTGAAGAAGGTGGGGATCCGGGATCTGGCTACGGCGAGACTTTAGAG
ACCCAGATGTGGACTCGAGGCTTCTGCGGCTGCGGGCCGGGGTCCGGCTTCCGAAACGAGCTCGTGGCGCCCCCTG
CATGACCCCAAACTCTCGGGGTTGCACAGAGGAGGGGCTAGTCGTTGGGGCGGGGTCGTCAGAGTACGTGTGTAT
TACAGCAAGTTCTTCTACCAATCGGGAATTGCTCTCCGATCCTTCTGAAAAGAACCTCTTGAAGATCTTGGCCCG
GGTGGTCGCGCGGTGTTTACGGGGCTTTGGGGTCCTGCTTTCCCCGAGCATCGCGGCCTCTGAGCTCATGCGGAA
CATAAAAGCTCGCAAGGCGTAGAACTTTTTCACGTTTTCATTTGTTTCCCGTAGGGGCCCCGAGAACGTGCATGA
CACCATGATTTCCCCCCCATTATAAAGATGAGAAAACCGAGGCTCTGAGAGGTTGAAGGGAATTGCCCAAAGTCA
GACACTCGGGAGTGTGCG

FIG. 17

BTG4 and miR34b (SEQ ID NO:58)

>chr11:110888000-110889202

AAGTCCCCAACAGAGCACAGAGGTGCAGATGAGACTCTCCAAGCCATCCTCCCATATGTCAGAGGCTACCCAAGC
CCACCTCCATTTGGAAAATTCAAACCTATAATTTGAGGTACCTGGGAAGCCGCTTTCCCAGGGCGGAATGGTCAC
GGAAACTGGGTAGGCTGGGGGCCTTCTTGGGGAATGAGGGAGTGGAGGAGCTCTTTGTCCCTCCTGCTAGATCAG
AAAGAGAAACCGTCTCAAGAATCTGGGCCTCCATCTTCTAGGCGTCTCCCTTGGAGGCCCCTTCAGGGACCGCCCAC
AGCGCTTTCTCTCAGCCTCCTCCCCCCCCCCATCCCCTCCCCCACC CCC TCT CC CCC CCCCT
GCC GGGTTCCAAGGA GTTGGT CCCC CCACAGTCACT GC CTCAGAG G GGG CA G
GGT AGAGAGCCAGCTCTAGGGTTTGGGGCTGGGAACTGAAGCCTGG TGAAGGAAGTGGGAGCCCGGGC A
GGAGG AAGGGGAAAGGAAAAG AGGGGAACCTGAG GGAGGGCCCTGAGAGGAG GGAGGCTG GGAAG
GGGAGGCCTGGCACTCCTGGGGGTCATGGGGGT GGG GCTCC GCCTGGGAGGG GGTCCTCCC
GCAG C CC CTGGCCCAGCTA TGTTGTG CTG AGGC G GGGGTCC CTGGGCC GGGGT
GTCCT GGGGC CTTG CCCAGCCATGGTAGGG TCCCC GTGAAATGGGGTC AGG GGCCC ACC
CCGCGTCGGCGCTGCGGACCGTCCGGGAGCTGCAGCCGCCGGTGCCCGGTGCTCGGTTTGTAGGCAGTGTCATTA
GCTGATTGTACTGTGGTGGTTACAATCACTAACTCCACTGCCATCAAAACAAGGCACAGCATCACCGCCGCCCGG
CCGGGAAGAAGACCGCCGGCTCGGGCAGCCGCCAGCCTTCGAGAGAAGATGCCTGAGAAGCCGCGGCGTCGGCGTGG
GTCCTGCGCAGCCTGCCCCGCCGAGCCGCCCGCTGCAAGTGCGAGGAAACCCGCCGGTTTCTCCAGATACAGTTAAAC
TGTTAGCTCTCTCTAGGAGTCACAGAAGATGAAACAGTCTCATGCCAGGAAAGCAAAATCCCTGGAGGTGAAGCC
CCT

FIG. 18

GLP1R (SEQ ID NO:59)

>chr6:39124186-39125076
TTGAGGGACCCTGAATGGGCGGGGGTTGCTGTAGCTTTCCTCAGCTGGGAGACCCGGGAGGAGGTCCGGGGTGCC
AGGGTGGGAGGAGGGCCTGGCTTGTCGCTGAAAGCCGGCCAGGCGCACTGTCGGCGCTCAGAGCTGGTGGCCGCC
TCCTGCGCTTCCTGATTCCCAGCCGCGCTCGCTCGGAGAGCAGTGCCCGCTATCTCCTGGCCCGGGACCGGCAGA
GGGGTGCGGCGGGGCGGGCCCAGGGGTCTCTGGCGGCCGGAAGAACCGGGACCCTGCCAGGCCCCTCCCGCGGGC
AGGGCGGCCCCTCGCCGGCTCCTCCCCCACCGCCCCGCCACCAGCC GGATCAGTCTCCGCACCGCGTTCCGCAG
GTGGCAGCGATGGCCCAGTCCTGAACTCCCCGCCATGGCCGGCGCCCCCGGCCCGCTGCGCCTTGCGCTGCTGCT
GCTCGGGATGGTGGGCAGGGCCGGCCCCCGCCCCCAGGTGAGATCCAGGGACCC A ACAC GGGGAGG G
GTGGCTCTG GGCTGCAGG CAGTGTCCTGGTGGAGGGCCC GGACTTGAACGAAACTCCGAGACCGCTGGC
GGGGGCATCCGAAAGCCTCGGGGGGAGTAGGGACTGGAGACTTGGTGCCCCTGGGCTGGAAGGCCCAGGTGAGGG
CTTGGACTACAGAGGATTCCCCCCAACCCCAGCGAGGCGCCCTCTTCCTCGCCACCGGGTCCCTCTGCCCGGGC
ACCCGCTGCCCCGCGGCCGCCCCTGCGCTGACTTCTGCTCCGCTTCTCCTTTGTCCCCAGCACTTTCCCAACTCCT
TCTAAACCGTGTCAGCGGCCCTGGCACAGCCCGGCATCCTCCCGGACTCCCTCTGCCCCACAGTCT

FIG. 19

HOMER2 (SEQ ID NO:60)

>chr15:81411855-81412831
ATTATTTCCAGGAAAACTTCGATTTCCATTTTGCTTGTAATAAATCCAAACGTGGAGAACGACAAACTGCTTAGA
CTCACACAGGCCCTGGAGTTGACTGCGCCCAGGGGCGAAGAGACCGCGGAATGGCCGAGGCAGGAGGCCGGCCAG
GGCACCGGTCCCCGTCAGGTGCCCCCGTGCC GGCTGTATGGGAGGGGAAGGGCCA GGCTC CCCAGGC
CAGGGTGCCCCTGCTGGGTGTC TGCCC G GAGGG GGTCAGGTGGCCCCAGACTCC GGCGCAG
AGTGTGCGCTCGCTCCGGCTTGGGGAGGCGGGGGCCGGCCCGCCCGGAGGCTCCGAGCCCGGTTACGCCAGCCGC
GGCCCCGCAGTCCCTCCCGAGGGGCGCGCGGAGAGCGCGCGGCGCCGGGCTCACTCAC*CCCATCTCCGGCGCTGCT*
*CCGGCGGCCGCTCCGACGGGGCCTCTCGCGCTCGCTCTCCGCCCGCTCGGCAGCCGCTCCCCGCGCCGGCACATGC*
*CGCGGCCCGTGCGCGCCCGGCTCAGCCCCGGCGCCCGCTCCATTCCGCGGGGCTGCGCCGGCTGCCACTGCTGCCAC*
*TGCCGCCACCGCCGCCAGG*CGCAGGCGGGCGGGGGCTGGGCGGCCGCGCTGGGGCGGTGCCCGCCCCGCCCTCCC
CAGCCGCTACCCCCGCCCCGGCTCCTTACGTAACCTCGTGGCCCCCGGGCCGCGGCAGCGAGCCAAGAGGCGGGGG
GCGCAGCACTGTGTGCACCGTCCCCCGCGCAGCCGCCGCAGTCGCCCGCTTTTCTCCCGGCCACCCAGTCCTCGGT
GCCCGCCCCGCGTTGGCGCGCCCCCGCCCCACGCCGACCCCGGGCCCTGGCGCAGTGCCATCAACATCCTGCCTG
ATGGACTTAAAGTCCCATTCACACCTGGCGGGGACTTTAGGGCTACCTTTACTTTGCAGATAAGGGAACCGAGGC
CT

FIG. 20

GJC1 (SEQ ID NO:61)

>chr17:40262237-40263687
CTCTTAATTTTGAAGCTAGAGACTTAAGGAAACACACACACACACAAAACAGTTCTCAAGTTTGACAAAGTGGGG
GAAAAGTCATTTTAAGTAAAGACAACGAGTTAATCAGGAGGCGATGAGCCCAGTCCTTCCGCCCCGCTTTCCCGC
TTCCAGCCCTCGAACGAACCCTCCTCTAACCCCCGGGAGGCAGGAGTTCCAGCGGGGAGATGCGGGAAGCCTCAG
ACGAGCCCGCACGCCGCCCGGAGACGCAGGGATCGAGGTCGGGGAGACAAAGAGCAGCCCGCGAAGAGCC GG
G AGGGG GCC GCTC CCCTG CCCCTAAC CC GGTAGTTGT GCAC C GGG C C AG
TG C CTTCTGTC GGCTCCC AC T CC ACACCTC GCCCAGGACACCCC AGC TTTC
CCTCC ATTTGGAGC CCTGGGGACAAAGAGGGAGGGTG C GGGACAGTGGCAGGA GGC
G A CCCCTC GACT G GGAACCCCT G G CCCCCCTCCTTCTCC CTCTGGC CTCCTCC
C GACCTC GAGGTTCTCCT GCCCCTCCC GGCTCCCCAAGAGTTCTCCCGCCTCCCCCTGGGACCCCGC
CCCTGGCCCCGCTTCTCCTCAGCCGGCCCTGCGGCCGCCCCTCAC*CCGGCCGGCCGGTTCCCCCGGAGCCGCCTCCT*
*CCGCCGGGCCTCGGCCCGTCCCGCCGGTCGCGGCCTCATGTGCCCCGCGTCGCCATCGCCTTCACCCTCGCCTCT*
*CCTCCACCTCCTCCGCCGCTGCCGCCCTTCGCCTCAGTCTCCAGCCGAGGCAGAAGCCGCTCCCGCCCGCTGC*CGCC
GCCGCCGCCGCCTCCCGCTCCCGCCGCCGCGACCCGCGGGAAGGCGCCTGCGCACTGCGCGCTGCGGTGGGGCG
GGGGCGTCCCGCCGCGGCCCCGGAGCGGGGGGCGCGCGCACCGTGGCGCTCGAGTGGGAGGGGGGCGCCCCAGAA
CGCGCGGGAAGCGACGCGAGCGCCAACTTTCCGCGGTCGAGTCCTCGCCGCTCTCTCGGATAGTCCGGACGCGG
CGGAGGCGCGGCGCGCGTGGGAGTCACCCGCGTGGAGTCTGGACCCCGGGTGGGCGCAGACTTCGCTCCGGACAG
TTCATTCTTCCAAGCTGATTTTCGGGCGAGAGTCCCCCGCCAGCCGCGCCTCAGTTTGAGCGGGCCGCTAACGGC
GCCGTGGGTTCTCGCCTTACCTGGGTATCCTGGGTTGGTTTAGCGGGCCCAGAGTTGTCTTCTGCGCGCTCCGCC
GAGGCCTTGGTCCATTGTAGCACGGGATGCTAATGTCTCCTCCCAGGTTCTGCTCTACAATTCCTCGAGGATCTG
GCGGGCCCTGCGTGGATCTAGCTAGA

FIG. 21

DOCK8 (SEQ ID NO:62)

>chr9:204487-205531
CAACCCTTAATAACACCTAGCCTTACGAATCCCTGGGGTGATTCCCGACCTCGCCAGCTTTGTGGGGCTCCCCCG
ACTTGCCTACATTCCCTGGCAGCCTCGCAGCTTCGGCAGATGGAGCTTCCGGCCTGCCGCGCAGTGGTCGCCTGT
CGTCCGCCCGCGCTCCCTTCGGCCGGAGGTCGGCGGCCCCGGGCAGAGCGCGCCGTCTGCCCCAGTATCGGGAGG
CCAGTTCCGCGCTGGGCCCACGCCCTCCTCGCCCGCCGCTGCCTGCGCGCCAGGCCGGGTGGCGGAGCCGGCCGT
CGCTGCTCCGAGCTCGGACCCTCCCCCGGGGTGATTTCGGCTTAGAAGGTGGAAATGCGGAAGTTTCCAGCGCCG
*ACCGACAGACGAGGTTTGCGCTTGGCTGGGCATGTTCCGCGGCTACTCTGCGGCGCGCCAGGCCCCGCTTTCCG*
*CACCCCGCGACCCTAGAAGCCACCGAACCGCCGGCGGCCATGGCCACTCTGCCGAGCCGCAGAGCGCCGCGCGTT*
*CGCGCTCAAGATCAACAGGTAAGACGCCCCCCGCGGCGCGCAGGTTGCGGCCGGACAGCCCAGCG*CTGGTGTGAA
GCGGAGCTTCGCTGCAGGGGCCGAGGCCGGACCGAGTCCATTCGCGTCCGCGGCGGGGCGCGCCTGAGACCTGGGG
CGCCCGGTTCCCGAGGCTGCGGCCGGTGGAGCCGCTGGACGCGCGGCCGCTCCTGCGCTGGGCCCGGCCGAGGTCCT
CCCCAAGAATCTCGGTGCTCCTGGATGTCCTCAGCCGCCGGGGATCCCTTCCCCGAACAACCTCGCCCGCTCCGC
CCTCCAGGTTCTTACAGGTGGCCGGGTCCCAGAAGGGTGATAGGCGCCTGGGTAACCGTGTTGGGCGCGCCACGG
AGTGTCTCATAAACGGCTCCTTCCTTTGAGGCAAGTCTGAGCGCGGGGGGAAGAAGTGAAGTGGCTGAAATTAGA
GTTGCGTTTGAGGCAGGCTGCAAGCCTTCTGTCGTCCTGAGCAAGGCTCCGTCCTCGCCTGCTTCATTAT

FIG. 22

ZNF583 (SEQ ID NO:63)

>chr19:61607069-61607768
TTAATCACACGTACATCCTACCGGGCCCCTCTCCAGCTGGCTCAGGCTCCACACTGGTCCTCCAGCTCCCTTTTC
TCAGCGATGGACTCACAGCCCCACCCGGAGCGCTGGAGCGCGGACGCGGTCACTGCGCGTGCGCCTCACCGCGCT
GGCACCCCGGCCTGGCAGCCTTTGGGGACCTGAACCAGCTGCGCCTGCGCAGGTGGAACGGGTGGAACGGGTGGG
GGAGCGGACAGTCGAACGGCCTGAGAGGGCTCAGCTGGTCCGGGTGGGATTCTGAAGGCCAGCGGAGGTGGGCTT
ACTAGGGAAAGGGGCGCAGCAGTAACTACCCGCAACTGAGCGGCGGGATCTGCGGCCGCCCGGGGCCCTCGGCCA
ACATCCCAGCATCCTCTGCGCCGCGCCGGCCCCGGACTCCATTTCCCAGCGGCCCCTGCGGCCTGCCCTAGGGCT
GCGGCGCCTTT*GTGAGCGCGGCCGCCCGGCCAGGATCGAGCCCTGGCCCGGGCCCTGGCCCAGCCCCGGCCTCCAA*
*GGACCGCGCCGAAGGAGGTGCCCACTGGAGGGAGGAGGCG*GTGAGGAGCGCGGGATGGAGCTGACGCCGGGAGCG
GCCATGCCACCATGTGTGGGACCGTGTGTGACAGTGTGTGAGAATGTGTGAGACATTAAGGAACCGTGTGTGACA
ATGTGTTTGACAGTGTGGAATCGTG

FIG. 23

NME4 (SEQ ID NO:64)

>chr16:386938-387750

GTGGGCCTTCCTCCGTGGGAAAGCGTTAAAACGATAGTTAACGGTTGCGTCGGTGTAAAGACGAATGCAATTCGA
GAAGGATTCATTATTATTTTGTTTTTTCTTCTGATTTTTAACAGAAATTGGCTTGAACATTTCCCCCTGAGC
CCGGCCACGGGGTCCGGGCGCGGGGGCTCCGGGCGCGGGGGCTCCCGGCGGCGGGGCGGTCT
CGGCTGGCACCCCCTCCCCCCCTCCT*CGCGCTCACAGCGGCCCGCGGGCCGGGCGTCATGGGCGGCCTC*
*TTCTGGCGCTCCGCGCTGCGGGGGCTGCGCTGCGGCCCGCGGGCCCCGGGCCCGAGCCTGCTAGTGCGCCACGG*
*CTCG*GGTGAGTGGGGCCGCGCGCCCCGGCGGGGACGCGGAGGGGAGGAAGGGGCGCGCGCCGCTCGGCCTTTGTG
CGCGCACGTGCGGGCTGGGGTCCGACTCCCCCAGAGGCCTCGGGGCGCGGGCTGCGGGGTCCGTCCGAGTTGGGG
AAGGCGCCCGGCTCGCACCCGCACGCCCCTCCAGTGCCCGTCCGGCTCTGCGGCTCCTTCTCGCCTCCCCAGGCCC
CAGGCTGCAGGCGCCCGGCGAGTTGGCAGCCTGGGCGGGTCCGGGGCGACCGAGGGCCCGGGAGCCCAAGGAAGG
CAGAGGCCGGCTGCAGCACTGGGCGGGGAGGGGGTCTCCCGGCCGGGGTGGGGGTGGGGGTGTGGGGGGTGAGG
GAGTCGGGGGGTGGGGGTGGGGGTGTGGGGGGGTGAGGGAGTCGGGGGGTGGGGGTGGGGGGAGCC

FIG. 24

SEQUENCE LISTING

```
<160> NUMBER OF SEQ ID NOS: 64

<210> SEQ ID NO 1
<211> LENGTH: 27
<212> TYPE: DNA
<213> ORGANISM: Artificial Sequence
<220> FEATURE:
<223> OTHER INFORMATION: Forward primer sequence for ALX3

<400> SEQUENCE: 1

gttcgggtta gcgttaattc ggttttc                                   27


<210> SEQ ID NO 2
<211> LENGTH: 24
<212> TYPE: DNA
```

-continued

<213> ORGANISM: Artificial Sequence
<220> FEATURE:
<223> OTHER INFORMATION: Reverse primer sequence for ALX3

<400> SEQUENCE: 2
cttcctactt atctctcccg ctcg 24

<210> SEQ ID NO 3
<211> LENGTH: 22
<212> TYPE: DNA
<213> ORGANISM: Artificial Sequence
<220> FEATURE:
<223> OTHER INFORMATION: TaqMan probe sequence for ALX3

<400> SEQUENCE: 3
aagtcgtggc gaaaggcgag ag 22

<210> SEQ ID NO 4
<211> LENGTH: 24
<212> TYPE: DNA
<213> ORGANISM: Artificial Sequence
<220> FEATURE:
<223> OTHER INFORMATION: Forward primer sequence for CCDC4

<400> SEQUENCE: 4
ttttgcgttt ggaattgttg cggc 24

<210> SEQ ID NO 5
<211> LENGTH: 28
<212> TYPE: DNA
<213> ORGANISM: Artificial Sequence
<220> FEATURE:
<223> OTHER INFORMATION: Reverse primer sequence for CCDC4

<400> SEQUENCE: 5
cctaataaaa ctaccgcacg tacgaacg 28

<210> SEQ ID NO 6
<211> LENGTH: 25
<212> TYPE: DNA
<213> ORGANISM: Artificial Sequence
<220> FEATURE:
<223> OTHER INFORMATION: TaqMan probe sequence for CCDC4

<400> SEQUENCE: 6
ttcgttgttg ttgatggaga cggcg 25

<210> SEQ ID NO 7
<211> LENGTH: 25
<212> TYPE: DNA
<213> ORGANISM: Artificial Sequence
<220> FEATURE:
<223> OTHER INFORMATION: Forward primer sequence for CHX10

<400> SEQUENCE: 7
aaaattttcg gattcgggtt tcggc 25

<210> SEQ ID NO 8
<211> LENGTH: 21
<212> TYPE: DNA
<213> ORGANISM: Artificial Sequence
<220> FEATURE:
<223> OTHER INFORMATION: Reverse primer sequence for CHX10

<400> SEQUENCE: 8
caaaaaacct acgaacgccc g 21

-continued

<210> SEQ ID NO 9
<211> LENGTH: 29
<212> TYPE: DNA
<213> ORGANISM: Artificial Sequence
<220> FEATURE:
<223> OTHER INFORMATION: TaqMan Probe Sequence for CHX10

<400> SEQUENCE: 9
accgtcccat ccctaaactc aaactaacc 29

<210> SEQ ID NO 10
<211> LENGTH: 20
<212> TYPE: DNA
<213> ORGANISM: Artificial Sequence
<220> FEATURE:
<223> OTHER INFORMATION: Forward primer sequence for DOCK8

<400> SEQUENCE: 10
ggtttcgggt agagcgcgtc 20

<210> SEQ ID NO 11
<211> LENGTH: 22
<212> TYPE: DNA
<213> ORGANISM: Artificial Sequence
<220> FEATURE:
<223> OTHER INFORMATION: Reverse primer sequence for DOCK8

<400> SEQUENCE: 11
taacgcgaaa caacgacgaa cg 22

<210> SEQ ID NO 12
<211> LENGTH: 27
<212> TYPE: DNA
<213> ORGANISM: Artificial Sequence
<220> FEATURE:
<223> OTHER INFORMATION: TaqMan probe sequence for DOCK8

<400> SEQUENCE: 12
agtatcggga ggttagtttc gcgttgg 27

<210> SEQ ID NO 13
<211> LENGTH: 23
<212> TYPE: DNA
<213> ORGANISM: Artificial Sequence
<220> FEATURE:
<223> OTHER INFORMATION: Forward primer sequence for GJA7

<400> SEQUENCE: 13
ttcgggtagt tgtcggtatc gtc 23

<210> SEQ ID NO 14
<211> LENGTH: 24
<212> TYPE: DNA
<213> ORGANISM: Artificial Sequence
<220> FEATURE:
<223> OTHER INFORMATION: Reverse primer sequence for GJA7

<400> SEQUENCE: 14
cgcgaaaata tcgaacgacg atcg 24

<210> SEQ ID NO 15
<211> LENGTH: 21
<212> TYPE: DNA
<213> ORGANISM: Artificial Sequence
<220> FEATURE:

-continued

<223> OTHER INFORMATION: TaqMan probe sequence for GJA7

<400> SEQUENCE: 15
aaacgacgcg cactcgacga c 21

<210> SEQ ID NO 16
<211> LENGTH: 24
<212> TYPE: DNA
<213> ORGANISM: Artificial Sequence
<220> FEATURE:
<223> OTHER INFORMATION: Forward primer sequence for GLP1R

<400> SEQUENCE: 16
agttcgggat tagttttcgt acgc 24

<210> SEQ ID NO 17
<211> LENGTH: 23
<212> TYPE: DNA
<213> ORGANISM: Artificial Sequence
<220> FEATURE:
<223> OTHER INFORMATION: Reverse primer sequence for GLP1R

<400> SEQUENCE: 17
aaccgaaaac gccgaccata acg 23

<210> SEQ ID NO 18
<211> LENGTH: 30
<212> TYPE: DNA
<213> ORGANISM: Artificial Sequence
<220> FEATURE:
<223> OTHER INFORMATION: TaqMan probe sequence for GLP1R

<400> SEQUENCE: 18
tcgtaggtgg tagcgatggt ttagttttga 30

<210> SEQ ID NO 19
<211> LENGTH: 20
<212> TYPE: DNA
<213> ORGANISM: Artificial Sequence
<220> FEATURE:
<223> OTHER INFORMATION: Forward primer sequence for HOMER2

<400> SEQUENCE: 19
ggaagggtta cgggtttcgc 20

<210> SEQ ID NO 20
<211> LENGTH: 27
<212> TYPE: DNA
<213> ORGANISM: Artificial Sequence
<220> FEATURE:
<223> OTHER INFORMATION: Reverse primer sequence for HOMER2

<400> SEQUENCE: 20
cgaaaatcta aaaccaccta acccgcg 27

<210> SEQ ID NO 21
<211> LENGTH: 25
<212> TYPE: DNA
<213> ORGANISM: Artificial Sequence
<220> FEATURE:
<223> OTHER INFORMATION: TaqMan probe sequence for HOMER2

<400> SEQUENCE: 21
tttgttgggt gttcgcgtgt ttcgg 25

-continued

<210> SEQ ID NO 22
<211> LENGTH: 25
<212> TYPE: DNA
<213> ORGANISM: Artificial Sequence
<220> FEATURE:
<223> OTHER INFORMATION: Forward primer sequence for BTG4

<400> SEQUENCE: 22
attcgtttcg tttcgcgttc gtttc 25

<210> SEQ ID NO 23
<211> LENGTH: 21
<212> TYPE: DNA
<213> ORGANISM: Artificial Sequence
<220> FEATURE:
<223> OTHER INFORMATION: Reverse primer sequence for BTG4

<400> SEQUENCE: 23
cgggagggtt ttgagaggag c 21

<210> SEQ ID NO 24
<211> LENGTH: 24
<212> TYPE: DNA
<213> ORGANISM: Artificial Sequence
<220> FEATURE:
<223> OTHER INFORMATION: TaqMan Probe Sequence for BTG4

<400> SEQUENCE: 24
aacgaccaac cgtccttaaa accc 24

<210> SEQ ID NO 25
<211> LENGTH: 28
<212> TYPE: DNA
<213> ORGANISM: Artificial Sequence
<220> FEATURE:
<223> OTHER INFORMATION: Forward primer sequence for miR34b

<400> SEQUENCE: 25
cgctctaaac gaccgaataa ctataacg 28

<210> SEQ ID NO 26
<211> LENGTH: 20
<212> TYPE: DNA
<213> ORGANISM: Artificial Sequence
<220> FEATURE:
<223> OTHER INFORMATION: Reverse primer sequence for miR34b

<400> SEQUENCE: 26
ctcccaaacc gaaaaccgcg 20

<210> SEQ ID NO 27
<211> LENGTH: 24
<212> TYPE: DNA
<213> ORGANISM: Artificial Sequence
<220> FEATURE:
<223> OTHER INFORMATION: TaqMan probe sequence for miR34b

<400> SEQUENCE: 27
taccaaacct ccccttcccg caac 24

<210> SEQ ID NO 28
<211> LENGTH: 25
<212> TYPE: DNA
<213> ORGANISM: Artificial Sequence
<220> FEATURE:
<223> OTHER INFORMATION: Forward primer sequence for NME4

-continued

<400> SEQUENCE: 28
gtttcgggtt ggtatcgttt ttcgc 25

<210> SEQ ID NO 29
<211> LENGTH: 24
<212> TYPE: DNA
<213> ORGANISM: Artificial Sequence
<220> FEATURE:
<223> OTHER INFORMATION: Reverse primer sequence for NME4

<400> SEQUENCE: 29
cgccaaaaaa aaccgcccat aacg 24

<210> SEQ ID NO 30
<211> LENGTH: 24
<212> TYPE: DNA
<213> ORGANISM: Artificial Sequence
<220> FEATURE:
<223> OTHER INFORMATION: TaqMan probe sequence for NME4

<400> SEQUENCE: 30
tttcgcgttt atagcggttc gcgg 24

<210> SEQ ID NO 31
<211> LENGTH: 24
<212> TYPE: DNA
<213> ORGANISM: Artificial Sequence
<220> FEATURE:
<223> OTHER INFORMATION: Forward primer sequence for NPTX1

<400> SEQUENCE: 31
agttttcgag cgttcgtcgt ttgc 24

<210> SEQ ID NO 32
<211> LENGTH: 24
<212> TYPE: DNA
<213> ORGANISM: Artificial Sequence
<220> FEATURE:
<223> OTHER INFORMATION: Reverse primer sequence for NPTX1

<400> SEQUENCE: 32
tctaacgcca aaaaacgacg accg 24

<210> SEQ ID NO 33
<211> LENGTH: 24
<212> TYPE: DNA
<213> ORGANISM: Artificial Sequence
<220> FEATURE:
<223> OTHER INFORMATION: TaqMan probe sequence for NPTX1

<400> SEQUENCE: 33
tgagtcgggg ttgcgttttc gttg 24

<210> SEQ ID NO 34
<211> LENGTH: 24
<212> TYPE: DNA
<213> ORGANISM: Artificial Sequence
<220> FEATURE:
<223> OTHER INFORMATION: Forward primer sequence for TMEM42

<400> SEQUENCE: 34
gtagggcgtc gtcgtatttt cgtc 24

<210> SEQ ID NO 35
<211> LENGTH: 23

-continued

<212> TYPE: DNA
<213> ORGANISM: Artificial Sequence
<220> FEATURE:
<223> OTHER INFORMATION: Reverse primer sequence for TMEM42

<400> SEQUENCE: 35
taccacccca actaaccgca acg 23

<210> SEQ ID NO 36
<211> LENGTH: 25
<212> TYPE: DNA
<213> ORGANISM: Artificial Sequence
<220> FEATURE:
<223> OTHER INFORMATION: TaqMan probe sequence for TMEM42

<400> SEQUENCE: 36
tttgtttcgt cggggtttcg ggtcg 25

<210> SEQ ID NO 37
<211> LENGTH: 23
<212> TYPE: DNA
<213> ORGANISM: Artificial Sequence
<220> FEATURE:
<223> OTHER INFORMATION: Forward primer sequence for TTLL12

<400> SEQUENCE: 37
gcgtttgtgg tttggttgtc gtc 23

<210> SEQ ID NO 38
<211> LENGTH: 21
<212> TYPE: DNA
<213> ORGANISM: Artificial Sequence
<220> FEATURE:
<223> OTHER INFORMATION: Reverse primer sequence for TTLL12

<400> SEQUENCE: 38
tcccgacatt ccccgaaatc g 21

<210> SEQ ID NO 39
<211> LENGTH: 27
<212> TYPE: DNA
<213> ORGANISM: Artificial Sequence
<220> FEATURE:
<223> OTHER INFORMATION: TaqMan probe sequence for TTLL12

<400> SEQUENCE: 39
tgcgtacgcg tatttgatgg tggttga 27

<210> SEQ ID NO 40
<211> LENGTH: 24
<212> TYPE: DNA
<213> ORGANISM: Artificial Sequence
<220> FEATURE:
<223> OTHER INFORMATION: Forward primer sequence for ZNF583

<400> SEQUENCE: 40
gatttgcggt cgttcggggt tttc 24

<210> SEQ ID NO 41
<211> LENGTH: 26
<212> TYPE: DNA
<213> ORGANISM: Artificial Sequence
<220> FEATURE:
<223> OTHER INFORMATION: Reverse primer sequence for ZNF583

<400> SEQUENCE: 41

-continued aaccctaaaa caaaccgcaa aaaccg 26

<210> SEQ ID NO 42
<211> LENGTH: 25
<212> TYPE: DNA
<213> ORGANISM: Artificial Sequence
<220> FEATURE:
<223> OTHER INFORMATION: TaqMan probe sequence for ZNF583

<400> SEQUENCE: 42
tttgcgtcgc gtcggtttcg gattt 25

<210> SEQ ID NO 43
<211> LENGTH: 25
<212> TYPE: DNA
<213> ORGANISM: Artificial Sequence
<220> FEATURE:
<223> OTHER INFORMATION: Linker designated RMCA24

<400> SEQUENCE: 43
tttgcgtcgc gtcggtttcg gattt 25

<210> SEQ ID NO 44
<211> LENGTH: 12
<212> TYPE: DNA
<213> ORGANISM: Artificial Sequence
<220> FEATURE:
<223> OTHER INFORMATION: Linker designated RMCA12

<400> SEQUENCE: 44
ccgggcagaa ag 12

<210> SEQ ID NO 45
<211> LENGTH: 25
<212> TYPE: DNA
<213> ORGANISM: Artificial Sequence
<220> FEATURE:
<223> OTHER INFORMATION: Forward primer sequence for VSX2

<400> SEQUENCE: 45
aaaattttcg gattcgggtt tcggc 25

<210> SEQ ID NO 46
<211> LENGTH: 22
<212> TYPE: DNA
<213> ORGANISM: Artificial Sequence
<220> FEATURE:
<223> OTHER INFORMATION: Reverse primer sequence for VSX2

<400> SEQUENCE: 46
caaaaaacct acgaacgccc cg 22

<210> SEQ ID NO 47
<211> LENGTH: 29
<212> TYPE: DNA
<213> ORGANISM: Artificial Sequence
<220> FEATURE:
<223> OTHER INFORMATION: TaqMan probe sequence for VSX2

<400> SEQUENCE: 47
accgtcccat ccctaaactc aaactaacc 29

<210> SEQ ID NO 48
<211> LENGTH: 24
<212> TYPE: DNA
<213> ORGANISM: Artificial Sequence
<220> FEATURE:
<223> OTHER INFORMATION: Forward primer sequence for BEND4

<400> SEQUENCE: 48
ttttgcgttt ggaattgttg cggc 24

<210> SEQ ID NO 49
<211> LENGTH: 28
<212> TYPE: DNA
<213> ORGANISM: Artificial Sequence
<220> FEATURE:
<223> OTHER INFORMATION: Reverse primer sequence for BEND4

<400> SEQUENCE: 49
cctaataaaa ctaccgcacg tacgaacg 28

<210> SEQ ID NO 50
<211> LENGTH: 25
<212> TYPE: DNA
<213> ORGANISM: Artificial Sequence
<220> FEATURE:
<223> OTHER INFORMATION: TaqMan probe sequence for BEND4

<400> SEQUENCE: 50
ttcgttgttg ttgatggaga cggcg 25

<210> SEQ ID NO 51
<211> LENGTH: 23
<212> TYPE: DNA
<213> ORGANISM: Artificial Sequence
<220> FEATURE:
<223> OTHER INFORMATION: Forward primer sequence for GJC1

<400> SEQUENCE: 51
ttcgggtagt tgtcggtatc gtc 23

<210> SEQ ID NO 52
<211> LENGTH: 24
<212> TYPE: DNA
<213> ORGANISM: Artificial Sequence
<220> FEATURE:
<223> OTHER INFORMATION: Reverse primer sequence for GJC1

<400> SEQUENCE: 52
cgcgaaaata tcgaacgacg atcg 24

<210> SEQ ID NO 53
<211> LENGTH: 21
<212> TYPE: DNA
<213> ORGANISM: Artificial Sequence
<220> FEATURE:
<223> OTHER INFORMATION: TaqMan probe sequence for GJC1

<400> SEQUENCE: 53
aaacgacgcg cactcgacga c 21

<210> SEQ ID NO 54
<211> LENGTH: 3238
<212> TYPE: DNA
<213> ORGANISM: Homo sapiens
<220> FEATURE:
<221> NAME/KEY: misc_feature
<223> OTHER INFORMATION: ALX3

<400> SEQUENCE: 54
tccctaccag cggctgcttc taagccactg tgcagccagg aagcagcgcc gcagcaggcc 60

-continued

```
cgagtgctcc actgtcccca cagaaggcat ccattgagac cgcgggacca gccttggctt    120
tcacatttcg ctgcagcctt gtcccgcgcc gcactgtttc ctccggccac tgtggggtca    180
ctaagcgacc tgcagaactc gctgaggccc aggctcctgc agctcccgcc gaagactcaa    240
agccagagtg gacataaacg ccgtgggcag gaccccggtg aggcctcggt gcccttcttg    300
ggggttctca gcgttggccc agaagcctca gcccgggtct aagaacttgg gactctcctc    360
gactttggcg atcggccggg tcatccggct cagggcctca gcggcagcgg gcaaaactct    420
agtaggagtc tcttgccgag ggcgtgtttc gacgtcagag ccaaactcgg gacagactag    480
ccaagcgcgg acggcgcgag agtggctggc agcgccagca cgcagcctgg gttcagagca    540
aggctgggcg ctctcagcaa agggcggcct ggggctgcgc gggcggcgga ctgcaggcgg    600
gagaagagcg aggtgcgcca ggctctgggg cgcgcaactg cccagcctcg tgaaagatcg    660
cgccgcagat ggggcgcagc tgcgcgctca ctcgtgtgga ctggaaacgc tccgagccgg    720
ttattttaaa aaccgggaaa taaggcgggt tccctcttcg cccgccactt cccaccaagt    780
aggctgtgcg gccctggggg ctgactgtcc tcaagcagcc aggctccacc gcgcgccgcg    840
ctgcgccgag gtccgctctg ccgcagggac gctggcagcc cgttgaacac cggcaagagc    900
gccagaggct agcggccgcc aggatctcta ccaggctctg ctcgcacccg cctgcctccc    960
tttcgtttgg cctgtcctcc gttcaactga aatcgttaat tttcttaccc ccttgttctc   1020
atttgatat attctacgct ttaaacatgc tccgttttct tttgtttagt ctgctccctc   1080
cctctttgtc ctttcccccct tctctagtta tccgtttcgt tcgatcttgc tcctgctttt   1140
tttattcgtt cgttcctcat ttattcattt tagttcatcc cagctcgccg actgccattt   1200
accctctcgt tctcgccgcg ctctccgttg ttttgttcaa tttcccttcc ccttttcttg   1260
gttgtcgctc gctttctttg gttttctttc tcggtatttc gttgtcaagg ccacccttgc   1320
cgtcggatcc cggggtgctg ggtttctccc ggccgctcgt tccgcaccag cgctctctgc   1380
agttcgcgcg gcaccggtgt ggtccggggg cccgagctgt cggtgccgga tgcggcgcgc   1440
ctagcaggga cgcgggcctg ggggggtggc tcctgcccga cgcggagcgc tgagccaggc   1500
cgggtacctg tctctggcgg tgctcaccgc actgcgcggc ctctgccgtc tggctgggat   1560
cagaggagcc aggccaactg cttctcatta agtcccaact gtggttttta tcaggaaagc   1620
ctctttcaaa gggcacagac acgaagctcc gcggactcgt tcatttcctc cgttgaccca   1680
cacacacctc cccgccctcc cctacacatt cccaccgccc cggctgggcg aaagccggag   1740
atgcccggcc actccgtgga ggcccgcgag gcgccagccg ggcggcggca gggggttgag   1800
gcggatcttg gaggatccag ttctgggcct aggctgcggg atatggcagc gcagataagg   1860
tgggtgcagt gcggaagccg agacgcctta caggtcatag ggtgcggcgg acggccgcag   1920
agctgccgat cagcctgcca ggcccctgcc ttcaggcgca ttctcggatg ccggcgcggt   1980
ccagccggcc ttagcacagg gcaccggccc gtgagcccgc ggcgccaggg ggttaggctg   2040
cccagggctg ctcctgactg cccagcggtg atgatccagc gcggggaagc caagactgcc   2100
agaagggcgg ctatcatagt gcataacggc agggaggcca gcttagtatg agaaataaga   2160
atacagttat tccgtcttga ggacagccct ggcattgcac gaccagtcgc ggccagactg   2220
tgccagtctg ccgcacaggc agcacccttc ctgtgaaggc taggcccggg gaggagagac   2280
gggccaagac caggccgcag tccccagccg accccgattt gaccactcta ggttgaggcc   2340
cagcctcagg gccctcaaag ggcgccagac acaaaagccg cgcttcttcg tcaggtctca   2400
```

```
gtgtggctcc acagccctcg gccgggtctg ggcttcaggg taggtggcag ttccagtcca   2460
acttcggcag agcatgctct ctccttccca ggtccaactg ctttcgggcc ccgactggac   2520
tccgggccgt cgccactgca ccttccctcg acctcccgcc ttccattccc gccgccgagg   2580
aacggtggtt caccctcccg ccccacactg gcctttgcct ggcccgggcc agcgccaacc   2640
cggcttccgt ggaagccgtg gcgaaaggcg agaggggcaa aaagttgaga aataggcgag   2700
cgggagagat aagcaggaag gcccgggtgg gcccgggtaa ggaagaagaa gagagggtcg   2760
ggctgcgcgc tacgccccgc gccgcgcgtt accttccgcg gggccctcgt agaagtggcc   2820
gccgttgagg gccgggccgg gcccgaggtc ctgcaggtac ttggcgggcg gcttggccgg   2880
ctctgggagg tagggctcca ggggcccgca ggccggaaag cgggtcagcc gcgggccgcg   2940
gggcggcgcg gggtgcaggt gaggcgcagc ggcgggggtt ccctgcgggc ccggaggctc   3000
gtcccccgag gccacatagg ggccgggtgc aggccccacg cggaaaggcg cgcagtgctc   3060
ggggtccatg ccggctcagg gcgcacaggc ctccggggct ccggggctcg cgctgcccgc   3120
gccgcctgtg agcgcccgcc aagggggagg gacctgggcg cgggggcgcg gagccccccgg  3180
gagcggcgcg cgccgcgggg ggcgggggc gggggcagg ggagggggcc gcgcctct       3238
```

```
<210> SEQ ID NO 55
<211> LENGTH: 2204
<212> TYPE: DNA
<213> ORGANISM: Homo sapiens
<220> FEATURE:
<221> NAME/KEY: misc_feature
<223> OTHER INFORMATION: VSX2

<400> SEQUENCE: 55
```

```
tagttttgat tttatttggg ttgtcgtttg gttggataaa aggggaattt ttttgggttt     60
tagagtatta gatatcggag ggggtatttg ggattaattt cgcgaagcgg gaagttcggc    120
ggggggggtgg ggggagttaa agatttgcgg ttttagtttt tttaaagaat agggagatga   180
cggggaaagt aggggaagcg ttgagtaagt ttaaattcga gatagtggtt aagagtattt    240
cggggggcgt ttcggttagg tgtattgggt tcggtattta ggagattttg ggtttgaata    300
aggagttttc gagtttttat tcgcgggtag cgttcgacgg tttggttttc gggtatttgt    360
tggcggcgcg tttagtgttt agtttcgcgg gggtgggcgg tatggggttt ttggggttcg    420
gggggttttt tggtttttat acgtagttta ttttttttgga agtgttgttc gattcgtaga   480
gcgtttattt gtagttattg ggtagagtat cggggtcgtt ggatattagt tagacggtta    540
gttcgggtag gtgaggagag gttgcgttgt tgtttgattg gggggcgata gtcgggagtt    600
tcgcgtcgtc ggttttcgtt tgttggatta ggtttttagg cggaaaagtt tttgttaggt    660
cgggggtcgt cgtttgggtt ttgggtcgac gcgtttggtg atggggttcg ggaggatgtt    720
tcggcgttcg tagggtttcg gttttaagcg tttcgggcgg tcgcgtagtt ttttagtttt    780
cgcgtcgggt agggttcggt tacggtattt tgttggagtt ttattgaaaa ttgggtttgg    840
ggtgtcggag ttcgtggtgt agagtcgtcg gtcgtgtcgg agggttttag tatcgttgtt    900
ttattgcggt ttcggtttgg tgtaggattc gtatttttcg agttcgatgt tgtttcggtt    960
tcggttttat ttttggtgtt taaagttgtt tgatttttaa atttcgcgtt ggttaattgg   1020
ggtttatttt ttatttttac gagtttagat aattcggtta tcgcggtagt taaagcggtc   1080
gttattttttt tttacgtaag cgttattata tattggagtt cggggacgcg cgggttcggg  1140
gattttgggt gatttttcg tttttttttc gcgttgtttt tcgggaggtg tgtcgcggtt    1200
```

-continued

```
cgttcgaatt ttcgattttt gtttgagttt ggtaattttt tcgatttttc gttgcgtttt   1260

attttgtttt acgtggaaag gtaacgaaaa ttagcgcgtc gtaggttttc gggtttcgag   1320

tagggacgta ttgtgtcgtt ttgcgaaaag gacggtgttc ggtagttttt agttttttcg   1380

gagtttagtt ttttacgttt tcgtttcgtt tttcgttttt cgaggttaat ttttcggttc   1440

ggggtattgg ggttggtcgc gtagggtagg gcgtagtagg gtcgcgagcg ttgtcgggga   1500

tttttgcggt tttttaaggt tgtttcgttt ttcgtcgttt cggttttaag cgcgtcgggg   1560

tttttgtttt ttttataacg aaatttgttt aaaattttcg gattcgggtt tcggcgcggg   1620

agaggttagt ttgagtttag ggatgggacg gttatcgggg cgttcgtagg ttttttgggg   1680

agatagagta ggttttcgtc gttcgcggag gtagttcggg gtggggtttt cgcgggtttc   1740

gggtatagcg gagcgcgttt tttattttgt cgtatgtttt tacgttcgtt ttttagattt   1800

tgaagatgtt ttttttagcg atcgaaaaat gtttaaattt gttttaaatt agattaagaa   1860

acggaagaag cggcgatata ggtgaggttt tcgttttttg ttattttttt tgttcgcgta   1920

tttcgttgtc gtttttcgtt tcgggatcgg gtttttcgga ttttattttc gtcgataacg   1980

gatttgaggt tcgaggtcgt gttagggcgt agattacggg ttgtttggcg gaatttgttc   2040

gggggttttg gcgtcggtat cggttgagta ggatgagtgg tcgtcgggaa agcggttcgg   2100

ttcgggtttt tttttttttg tttaggagaa aggaaaggtt ttaatatagg ttaaattgag   2160

ttatagagtg ggggcggttt ttagattttc gtattagtat attt                    2204
```

```
<210> SEQ ID NO 56
<211> LENGTH: 3476
<212> TYPE: DNA
<213> ORGANISM: Homo sapiens
<220> FEATURE:
<221> NAME/KEY: misc_feature
<223> OTHER INFORMATION: NPTX1

<400> SEQUENCE: 56

ctccagggtg ttcacccggg acagcacctg cctctccagc tcatcgatct tgctctgcag     60

cagatccttg aggctgttgg tctggctgga ggaattgagg cggctgtact gctgcggggt    120

gcaagggcgg gggaaaccac accgttaggc gaggcgcggg gaccgtgctg gaaggcccgc    180

ggcgcggtcc cctctgggcg actgcggggg cggcctggca gggagctggg gcgagtggcc    240

gccgcggggc ctcgcaggcg cggggaggca ccggccgggc acccgcgcgg ctgaggcgag    300

ggcgggggat gcctggccgg gtagggaacg gggtggggga gggcagaggg gcgagcgagc    360

cggagggggga accggagccg agggcgcgcg cggacctcga ggttctccag gcgggttttg    420

agcgattgca aagtttgccc gagttggctg agcgtctcgg cggccggtgt ccgggacagg    480

tcgcccatgg tgttcttgcc cgagccgggc tgcttgcggc cgccgcccgc ccgggcctcg    540

ccggctccgg ggtccagcgt gctctggctc tcgcagcggc ccagcttggc ggtcagctcg    600

cggatggtct ccttctggct caggatggtc tccttctgct gcagcaccgt ctcgcggagc    660

tgcagcacgc tgctccggag ctcctcggcg ccgccggcgg ccacggacgc ggcgcacatg    720

tcggcgtcca cgggcaccga ggtgcagatg aagcgcgtcg gcccgaaatc ctgggccccg    780

gcgcccagga ggcagagggc gagcagcgca caggtgcgcg cggcgcggcc ggccggcatg    840

gctgcgggca ccgggcgctc cgggcccggc tcggctcggc tggggctcgg ctccggctgg    900

gacccggctc gggctgtggc tccgcgagcg gcccgcgctc tgggcgccgc gctcttcggc    960

cgcgcggtcc acaccgccgc gctatcaggc ccccactgcc gcctgcgctg cggagcccgc   1020
```

-continued

```
gccttttatg ccgccgcggg aggggcctcg agccgccgac gtcagcgggg gaggaatccc   1080
gctttaattg tccgcggccc gggcccgcgg cgcggcgggg gtctcacgag cgcgccaccg   1140
gggctgcctc cgctcgcgtc ccccccgccc ttctgggagc tgccgcggcc ccctcctccc   1200
ccgcccccgc ctgggccggc gctgctgccc cgaaggctcc gagagctcag gggaaggaa   1260
gtcgggctcc ggccccggac tcgaggatgg accacctgcg tggtgtcccc gaacctccga   1320
cggggctcca ggcgggcggg aaaccaccgc gtccgggaga tagaattcgg ttcggccctc   1380
ctggctgcac tgaacaccct tgggccgggg tcgtttggag ccgggctggg tgcccaagga   1440
cccaggtcgt caacacccga gtgcccggtg gtcaacggct cggagtgggg cctcgcggcg   1500
ccactaagtc cagagcgggg gtcaccgggc cgccccgcgt ttcttagatg tccgtgtgct   1560
attgagaagc cgccgggcag cctgggtaca gggacttccc acgggtcggg gcccccggcg   1620
cctcccctcc cccagctccc gggctctgtg gacccggccc cgtccccggg ggactgtcag   1680
tccccacccc gtgcgggcgg ggcgctgggg acttctcgga ggcagaccta gctgatcgag   1740
cctttcctgt ccgcggcgcc ggcccgatcg cgggcaggcg gcgtcgccgg ggctggacgt   1800
tcgcagcggc gcttcggaag gggcccccgc gggagcagcc gcccgcgtct ccagcagctt   1860
ccccttgcca ggcgccgcgc gcgcccggta tccccgggtg tccacctgtg cgtgggggc   1920
tgtttcccgt ctgtccagcc gcgcccactt ctcaggccca aaggccagca ggaagggtcc   1980
cggaggtggc tgggggcgtc cacctgagaa gctccgctct cgctcagaca ccccacccgg   2040
cacccgcgca ctcgcgcctt catctggacc gcggggctcg gctcccgaga tcgcggtccg   2100
ggttccggcg ccgggctggg ggctcaggac cagggctggc gcagccgccc cgccccgccc   2160
cgccccgggg ctatcagagc ggtcaaagcc tcggaaatcc ctccgtccac gctcccgtgg   2220
tacagagaag gaaactgagg ctccgagact gcggggccgg gctacagccg tggcccccg   2280
acccctcccc gccgcccccg gcttctctgg tctctgcgtt ctgcagcctt tccctgcgcg   2340
cagccggggg ctgggggtcc ccagccagca gggacccacg ggcagtcccg ggtgccggga   2400
tcgggcgtcc gcccctcggg cgggagcaga ggccggctcg atggagacct tttgagaaa   2460
tggcggcctc tacccgcccc ccagcccccg agcgcccgcc gtctgcgttc agcatctcag   2520
cttttaagcc tccctgagcc ggggctgcgt tctcgttgtc tccttcggcc gccgcttcct   2580
ggcgccagag ggaccccgcg gcccgcacgg gcctgtcctc ggctccgctc ggagggtgtg   2640
cgggttcccg ctccgctggc cccgcttgcc caccacggcg cgcccaaacc cacgcggccc   2700
gcggcccctt gcgtgctctg ccgaccccgg gccgcaggag gggttagcct cgccggtccc   2760
cacgcggggt ctgcgccggc agcgccacgg gctggaacgc gcctcgggag aaattacccg   2820
cgcggggtcg cggcgtcttc tgccccaact cccgtaggga gccgctaggc gggtgccctc   2880
ctggccccag cgctttggcc tcgccgccct cccgcacgcg tccagtgggg aggccgcgcc   2940
cgtcaggcct ggagccggac cgtgcccagc cgagagcgcg cgggcgcggg agaggagccc   3000
tgccctgccc agggcaggct gtttagacgg ggcgggaacc cttagcctgg ccccgcgtct   3060
ctatccccag cagccgtgga gccttcctag ccgcccaagg ccagggaccc tgcctggctt   3120
ttcctccagg gcagcagatc tcagcggcct ggcacctcgg cacagaggag cgtgtccccc   3180
ttccgcagag gaagggagtg gacggcgtca gaaagggagg ggagcctggg gcggtgtctg   3240
gggctagcgg gacctctggg cactgtgggg ccccaggaga ggagaccctc gggtccagcc   3300
tgcaactgtt gtgcaggagg cgctgggcgg gacacctgca ggcgctgcac acacacgcga   3360
gggccaccat gccgcgtttc tccttcacaa gaccctgggc aagcggaggg tcgtatttag   3420
```

gattccctcg gcctccccag tgttctgaaa gtatctgaga gggagggagc aggaaa 3476

<210> SEQ ID NO 57
<211> LENGTH: 2418
<212> TYPE: DNA
<213> ORGANISM: Homo sapiens
<220> FEATURE:
<221> NAME/KEY: misc_feature
<223> OTHER INFORMATION: BEND4

<400> SEQUENCE: 57
actgggagct ggtggagagg tcccttgggc gcaggcctca ggctgtggcc tcgcaaccag 60
cccatctcgc tccctgcagg caggcagtgg gctgctttgc cgggcagcgc ccgcagactc 120
gagataaagg agaggagtcg cggaccccag agtgggtgcc tcccacgagg cgtttctgta 180
aggctcgggc cgagatgctc gggaggggca ggaccccgcg gcgcggcagc gtgccacgga 240
cggggacgag gggatggcgg ggacgacgac gtgggcggtg ggagcagagt gcctgcgact 300
cccggggcag gaaggagggg cgggatggtt ccccgcgccc gaaatccacg gcgtggcgga 360
cgcggaggag ccccgagtct cacaaccaag gggtgggaag gaaaagggac agagcgagac 420
agagcgcccc cgagaaacac aggcgcacaa aaaaagacag aaggaaaaac ggaactgaga 480
gccagccagc atggactgcg acagcgtgag agtgcatcaa agaggtggcg aagaaagcac 540
tagaaggcaa aggagaagtg gagagaagaa gaaacaaatg gaggaagaag gagaaaggga 600
aaaagcagac ggaaaaagtg aagtagtacg agggcgtccc agcggggcgg cccgagaagc 660
tccagcttct tcccgagcgg ccgccgctat cccccggggg ggcgtctggc cccactccgg 720
accacgcccg agcgatcctg gtcgccgact gccacagccg tgcttcccgg cgcgggatcc 780
aagccgcgga gccacctgtt aggcgcgcgc cgtcggaagc ccaggcgcgg cggcgctgga 840
gaatcctctc gaagtttccg ggtgcgcggg gaggccccag gtgcgccccg acatcccgac 900
acggcccagc acgggtaagt gtcggcggcc ccccgcttct ccttcctggg tcccctcccg 960
ctgcccccgg ccgtggcggg aaggaaagtt gtgcggagag ttggtacctg cgctgagctc 1020
caggctggcg ctgtcgctac ccgtgccgcc ggtgccggcg gccgccgccg cgcctgggcc 1080
atacctgacg acagcggcga acgaagacga cgaggaggcg gcgggggacg cgggcggcgg 1140
ctgcgccgga gtcctcaagt ggccctggga tgtggcgggc gtgcaggacg gcgacgacga 1200
cgaagcggcg gcggcggccc ggccgggccc ggggggtag gagctctgcg cctggaactg 1260
ctgcggcggc ggctcgctgc tgctgatgga gacggcggcg tgcggcgcga agggcggcgg 1320
gggcggcggg ggcgcccgca cgtgcggcag ctccaccagg gtgggtcgct cgtagcgctt 1380
ggccagcgcc ggtctcttgc tggggaacgt cttgaggacg ctgtaggggc tgcgctgctt 1440
gtagattttg gggacgctgg gcccctcctc tgccggctgc atctcttcct ccatccggcg 1500
cctcggggcc ggtccctcgg agcacgtccc ctccccgccg ggcgccgggc tccgagggtg 1560
cctccgccgc ctgcccgccg ggtctgccct ggtgcgcgcg tgtgggaggg tgtgtgtctg 1620
tgccgtggcc gccgccgccg ccgcctgtcg ctgaggctgg catcgccgag cccccgcgcg 1680
gggggctgcc gcccgagctc ctgattgaca ggctgcctcg ccaatgcctg gagggagaaa 1740
ggaggtaaag agcaagtgtt tagggtaata tctgctaatg ataatggggg cggggcgggg 1800
cctggcgccg cagccgcccg cggggtctgc ctggcggctc cgcgcctccg acggggagcg 1860
ggggaagggg gaaagcgagg acctggagga cgcccgggaa ctggtgaaga aggtggggat 1920
ccgggatctg gctacggcga gactttagag acccagatgt ggactcgagg cttctgcggc 1980

```
tgcgggcggg gtccggcttc cgaaacgagc tcgtggcgcc ccctgcatga ccccaaactc   2040

tcggggttgc acagaggagg ggctagtcgt tggggcgggg tcgtcagagt acgtgtgtat   2100

tacagcaagt tcttctacca atcgggaatt gctctccgat ccttctgaaa agaacctctt   2160

gaagatcttg gcccgggtgg tcgcgcggtg tttacggggc tttggggtcc tgctttcccc   2220

gagcatcgcg gcctctgagc tcatgcggaa cataaaagct cgcaaggcgt agaacttttt   2280

cacgttttca tttgtttccc gtaggggccc cgagaacgtg catgacacca tgatttcccc   2340

cccattataa agatgagaaa accgaggctc tgagaggttg aagggaattg cccaaagtca   2400

gacactcggg agtgtgcg                                                 2418
```

<210> SEQ ID NO 58
<211> LENGTH: 1203
<212> TYPE: DNA
<213> ORGANISM: Homo sapiens
<220> FEATURE:
<221> NAME/KEY: misc_feature
<223> OTHER INFORMATION: BTG4 and miR34b

<400> SEQUENCE: 58

```
aagtccccaa cagagcacag aggtgcagat gagactctcc aagccatcct cccatatgtc     60

agaggctacc caagcccacc tccatttgga aaattcaaac ctataatttg aggtacctgg    120

gaagccgctt tcccagggcg gaatggtcac ggaaactggg taggctgggg gccttcttgg    180

ggaatgaggg agtggaggag ctctttgtcc ctcctgctag atcagaaaga gaaacgtctc    240

aagaatctgg gcctccatct tctaggcgtc tcccttggag gcccttcagg gaccgcccac    300

agcgctttct ctcagcctcc tcccccccc catcccctcc cccacccgcc ccgtctcgcg    360

cccgccccgc ccctcggccc gcggggttcc aaggacggtt ggtcgccccc gccacagtca    420

ctcggccgct cagagcggcg gggcgcacgg ggtcgagaga gccagctcta gggtttgggg    480

ctgggaactg aagcctggcg tgaaggaagt gggagcccgg gccgaggagg cgaaggggaa    540

aggaaaagcg aggggaacct gagcgggagg gccctgagag gagcgggagg ctgcgggaag    600

gggaggcctg gcactcctgg gggtcatggg ggtcggggcg cggctcccgg cctgggaggg    660

cgcgggtcct ccccggcagc gccgcccgct ggcccagcta cgcgtgttgt gcgctgcgag    720

gccggcgggg gtcccgctgg gcccgggggt gtcctcgggg gccgcttgcg cccagccatg    780

gtagggcgtc ccccggtgaa atggggtccg aggcgggccc cgaccccgcg tcggcgctgc    840

ggaccgtccg ggagctgcag ccgcgggtgc ccggtgctcg gtttgtaggc agtgtcatta    900

gctgattgta ctgtggtggt tacaatcact aactccactg ccatcaaaac aaggcacagc    960

atcaccgccg cccggccggg aagaagacgc cggctcgggc agcccgcagc cttcgagaga   1020

agatgcctga gaagcgcggc gtcggcgtgg gtcctgcgca gcctgccccg cgagcgcccg   1080

ctgcaagtgc gaggaaaccc gcggtttctc cagatacagt taaactgtta gctctctcta   1140

ggagtcacag aagatgaaac agtctcatgc caggaaagca aaatccctgg aggtgaagcc   1200

cct                                                                 1203
```

<210> SEQ ID NO 59
<211> LENGTH: 891
<212> TYPE: DNA
<213> ORGANISM: Homo sapiens
<220> FEATURE:
<221> NAME/KEY: misc_feature
<223> OTHER INFORMATION: GLP1R

<400> SEQUENCE: 59
ttgagggacc ctgaatgggc gggggttgct gtagctttcc tcagctggga gacccgggag 60
gaggtccggg gtgccagggt gggaggaggg cctggcttgt cgctgaaagc cggccaggcg 120
cactgtcggc gctcagagct ggtggccgcc tcctgcgctt cctgattccc agccgcgctc 180
gctcggagag cagtgcccgc tatctcctgg cccgggaccg gcagaggggt gcggcggggc 240
gggcccaggg gtctctggcg gccggaagaa ccgggaccct gccaggcccc tcccgcgggc 300
agggcggccc ctcgccggct cctcccccac cgcccgccac cagcccggga tcagtctccg 360
cacgcggttc cgcaggtggc agcgatggcc cagtcctgaa ctccccgcca tggccggcgc 420
ccccggcccg ctgcgccttg cgctgctgct gctcgggatg gtgggcaggg ccggcccccg 480
cccccaggtg agatccaggg accccgacga caccggggga ggcgggtggc tctgcgggct 540
gcaggcgcag tgtcctggtg gagggccccg ggacttgaac gaaactccga gaccgctggc 600
gggggcatcc gaaagcctcg gggggagtag ggactggaga cttggtgccc ctgggctgga 660
aggcccaggt gagggcttgg actacagagg attcccccca accccagcga ggcgccctct 720
tcctcgccac ccgggtccct ctgcccgggc acccgctgcc ccgcggccgc cctgcgctga 780
cttctgctcc gcttctcctt tgtccccagc actttcccaa ctccttctaa accgtgtcag 840
cggccctggc acagcccggc atcctcccgg actccctctg ccccacagtc t 891

<210> SEQ ID NO 60
<211> LENGTH: 977
<212> TYPE: DNA
<213> ORGANISM: Homo sapiens
<220> FEATURE:
<221> NAME/KEY: misc_feature
<223> OTHER INFORMATION: HOMER2

<400> SEQUENCE: 60
attatttcca ggaaaacttc gatttccatt ttgcttgtaa taaatccaaa cgtggagaac 60
gacaaactgc ttagactcac acaggccctg gagttgactg cgcccagggg cgaagagacc 120
gcggaatggc cgaggcagga ggccggccag ggcaccggtc cccgtcaggt gccccccgtgc 180 ccgggctgta tgggagggga agggccacgg gctccgcgcc caggccaggg tgcccctgct 240
gggtgtccgc gtgccccggc ggagggcgcg ggtcaggtgg ccccagactc ccgggcgcag 300
agtgtgcgct cgctccggct tggggaggcg ggggccggcc cgccgggagg ctccgagccc 360
ggttacgcca gccgcggccc cgcagtccct ccggaggggc gcgcggagag cgcgcggcgc 420
gggctcactc accccatctc cggcgctgct ccggcggccg ctccgacggg gcctctcgcg 480
ctcgctctcc gcccgctcgg cagccgctcc ccgcgcggca catgcggcgg cccgtgcgcg 540
cccggctcag ccccggcgcc gctccattcc gcggggctgc gcggctgcca ctgctgccac 600
tgccgccacc gccgccaggc gcgggcgggc gggggctggg cggccgcgct ggggcggtgc 660
ccgccccgcc ctccccagcc gctacccccg cccggctcct tacgtaacct cgtggccccc 720
gggccgcggc agcgagccaa gaggcggggg gcgcagcact gtgtgcaccg tcccccgcgc 780
agccgcgcag tcgccgcttt tctcccgggc cacccagtcc tcggtgccgg ccccgcgttg 840
gcgcgccccc gccccacgcc gacccggggc cctggcgcag tgccatcaac atcctgcctg 900
atggacttaa agtcccattc acacctggcg gggactttag ggctaccttt actttgcaga 960
taagggaacc gaggcct 977

<210> SEQ ID NO 61

-continued

<211> LENGTH: 1451
<212> TYPE: DNA
<213> ORGANISM: Homo sapiens
<220> FEATURE:
<221> NAME/KEY: misc_feature
<223> OTHER INFORMATION: GJC1

<400> SEQUENCE: 61

```
ctcttaattt tgaagctaga gacttaagga aacacacaca cacacaaaac agttctcaag      60
tttgacaaag tgggggaaaa gtcattttaa gtaaagacaa cgagttaatc aggaggcgat     120
gagcccagtc cttccgcccc gctttcccgc ttccagccct cgaacgaacc ctcctctaac     180
ccccgggagg caggagttcc agcggggaga tgcgggaagc ctcagacgag cccgcacgcc     240
gccggagacg cagggatcga ggtcggggag acaaagagca gcccgcgaag agcccgggcg     300
gcgaggggcg gcccggctcc gccctgcgcc cctaaccgcc cgggtagttg tcggcaccgc     360
cggggcgccg ccgagtgcgc gccgcttctg tccgggctcc ccgaccgtcg cccgacacct     420
ccgcggccca ggacaccccc gagccgtttc cctcccgatt tgggagccgc gcgcctgggg     480
acaaagaggg agggtgcgcc ggggacagtg gcaggacgcg ggccggcgac gcccctccgg     540
actcggcggg aacccctcgg cggcgccccc ctccttctcc cgctctggcc gcgctcctcc     600
ccggacctcc ggaggttctc ctcggcccct ccccgggctc cccaagagtt ctcccgcctc     660
cccctgggac cccgcccctg gcccgcttct cctcagccgg ccctgcggcc gcccctcacc     720
cggcggcggg ttcccccgga gccgcctcct ccgccgggcc tcggcccgtc ccgccggtcg     780
cggcctcatg tgccccgcgt cgccatcgcc ttcaccctcg cctctcctcc acctcctccg     840
ccgctgccgc cttcgcctca gtctccagcc gaggcagaag ccgctcccgc cgctgccgcc     900
gccgccgccg cctcccgctc ccgccgccgc gacccgcggg aaggcgcctg cgcactgcgc     960
gctgcggtgg gggcgggggc gtcccgccgc ggcccgggag cggggggcgc gcggcacgtg    1020
gcgctcgagt gggagggggg cgccccagaa cgcgcgggaa gcgacgcgag cgccaacttt    1080
ccgcggtcga gtcctcgccg ctctctcgga tagtccggga cgcggcggag gcgcggcgcg    1140
cgtgggagtc acccgcgtgg agtctggacc ccgggtgggc gcagacttcg ctccggacag    1200
ttcattcttc caagctgatt ttcgggcgag agtcccccgc cagccgcgcc tcagtttgag    1260
cgggccgcta acggcgccgt gggttctcgc cttacctggg tatcctgggt tggtttagcg    1320
ggcccagagt tgtcttctgc gcgctccgcc gaggccttgg tccattgtag cacgggatgc    1380
taatgtctcc tcccaggttc tgctctacaa ttcctcgagg atctggcggg ccctgcgtgg    1440
atctagctag a                                                         1451
```

<210> SEQ ID NO 62
<211> LENGTH: 1045
<212> TYPE: DNA
<213> ORGANISM: Homo sapiens
<220> FEATURE:
<221> NAME/KEY: misc_feature
<223> OTHER INFORMATION: DOCK8

<400> SEQUENCE: 62

```
caacccttaa taacacctag ccttacgaat ccctggggtg attcccgacc tcgccagctt      60
tgtggggctc ccccgacttg cctacattcc ctggcagcct cgcagcttcg ggcagatgga     120
gcttccggcc tgcgcgcagt ggtcgcctgt cgtccgcccg cgctcccttc ggccggaggt     180
cggcggcccc gggcagagcg cgccgtctgc cccagtatcg ggaggccagt tccgcgctgg     240
gcccacgccc tcctcgcccg ccgctgcctg cgcgccaggc cgggtggcgg agccggccgt     300
```

cgctgctccg agctcggacc ctcccccggg gtgatttcgg cttagaaggt ggaaatgcgg 360
aagtttccag cgccgaccga cagacgaggt ttgcgcttgg ctgggcatgt tccgcggcta 420
ctctgcggcg cgccaggccc ccgctttccg caccccgcga ccctagaagc caccgaaccg 480
ccggcgggcc atggccactc tgccgagcgc agagcgccgc gcgttcgcgc tcaagatcaa 540
caggtaagac gccccccgcg gcgcgcaggt tgcggccgga cagcccagcg ctggtgtgaa 600
gcggagcttc gctgcagggg ccgaggccgg acgagtccat tcgcgtccgc ggcggggcgc 660
gcctgagacc tggggcgccc ggttcccgag gctgcggcgg tggagccgct ggacgcgcgg 720
cggctcctgc gctgggcccg gcgaggtcct ccccaagaat ctcggtgctc ctggatgtcc 780
tcagccgccg gggatccctt ccccgaacaa cctcgcccgc tccgccctcc aggttcttac 840
aggtggccgg gtcccagaag ggtgataggc gcctgggtaa ccgtgttggg cgcgccacgg 900
agtgtctcat aaacggctcc ttcctttgag gcaagtctga gcgcgggggg aagaagtgaa 960
gtggctgaaa ttagagttgc gtttgaggca ggctgcaagc cttctgtcgt cctgagcaag 1020
gctccgtcct cgcctgcttc attat 1045

<210> SEQ ID NO 63
<211> LENGTH: 700
<212> TYPE: DNA
<213> ORGANISM: Homo sapiens
<220> FEATURE:
<221> NAME/KEY: misc_feature
<223> OTHER INFORMATION: ZNF583

<400> SEQUENCE: 63
ttaatcacac gtacatccta ccgggcccct ctccagctgg ctcaggctcc acactggtcc 60
tccagctccc ttttctcagc gatggactca cagccccacc cggagcgctg gagcgcggac 120
gcggtcactg cgcgtgcgcc tcaccgcgct ggcaccccgg cctggcagcc tttggggacc 180
tgaaccagct gcgcctgcgc aggtggaacg ggtggaacgg gtgggggagc ggacagtcga 240
acggcctgag agggctcagc tggtccgggt gggattctga aggccagcgg aggtgggctt 300
actagggaaa ggggcgcagc agtaactacc cgcaactgag cggcgggatc tgcggccgcc 360
cggggccctc ggccaacatc ccagcatcct ctgcgccgcg ccggccccgg actccatttc 420
ccagcggccc ctgcggcctg ccctagggct gcggcgcctt tgtgagcgcg gccgccggcc 480
aggatcgagc cctggcccgg gccctggccc agccccggcc tccaaggacc gcgccgaagg 540
aggtgcccac tggagggagg aggcggtgag gagcgcggga tggagctgac gccgggagcg 600
gccatgccac catgtgtggg accgtgtgtg acagtgtgtg agaatgtgtg agacattaag 660
gaaccgtgtg tgacaatgtg tttgacagtg tggaatcgtg 700

<210> SEQ ID NO 64
<211> LENGTH: 813
<212> TYPE: DNA
<213> ORGANISM: Homo sapiens
<220> FEATURE:
<221> NAME/KEY: misc_feature
<223> OTHER INFORMATION: NME4

<400> SEQUENCE: 64
gtgggccttc ctccgtggga aagcgttaaa acgatagtta acggttgcgt cggtgtaaag 60
acgaatgcaa ttcgagaagg attcattatt attttgtttt ttcttctgat ttttaacaga 120
aattggcgtt gaacatttcc cccgtgagcg ccgggccacg gggtccgggg gcggcggggg 180

-continued

```
gctccggggc ggcggggggc tcccgggcgg gcgggggcgg gtctcgggct ggcaccgccc    240

tccgcgcccg ctcctcgcgc tcacagcggc ccgcgggccg ggcgtcatgg gcggcctctt    300

ctggcgctcc gcgctgcggg ggctgcgctg cggcccgcgg gccccgggcc cgagcctgct    360

agtgcgccac ggctcgggtg agtggggccg cgcgccccgg cggggacgcg gaggggagga    420

aggggcgcgc gccgctcggc ctttgtgcgc gcacgtgcgg gctggggtcc gactccccca    480

gaggcctcgg ggcgcgggct gcggggtccg tccgagttgg ggaaggcgcc ggctcgcacc    540

cgcacgcccc tccagtgccc gtccggctct gcggctcctt ctcgcctccc caggccccag    600

gctgcaggcg cccggcgagt tggcagcctg ggcgggtccg gggcgaccga gggcccggga    660

gcgcaaggaa ggcagaggcc ggctgcagca ctgggcgggg agggggtctc ccggccgggg    720

tgggggtggg ggtgtggggg ggtgagggag tcggggggtg ggggtggggg tgtggggggg    780

tgagggagtc ggggggtggg ggtgggggga gcc                                 813
```

DNA HYPERMETHYLATION DIAGNOSTIC BIOMARKERS FOR COLORECTAL CANCER

CROSS-REFERENCE TO RELATED APPLICATIONS

This application is a 35 U.S.C. §371 U.S. national entry of International Application PCT/US2011/054781 having an international filing date of Oct. 4, 2011, which claims the benefit of U.S. Provisional Application No. 61/443,562 filed Feb. 16, 2011 and U.S. Provisional Application No. 61/389,304 filed Oct. 4, 2010, the contents of each of the aforementioned applications are herein incorporated by reference in their entireties.

STATEMENT OF GOVERNMENTAL INTEREST

This invention was made with U.S. government support under grant no. U01CA084986 and grant no. R01CA0133012. The U.S. government has certain rights in the invention.

FIELD OF THE INVENTION

The present invention relates to the field of cancer. More specifically, the present invention relates to the use of biomarkers to detect colorectal cancer.

INCORPORATION-BY-REFERENCE OF MATERIAL SUBMITTED ELECTRONICALLY

This application contains a sequence listing. It has been submitted electronically via EFS-Web as an ASCII text file entitled "P11173-02_Sequence_Listing_ST25.txt." The sequence listing is 36,807 bytes in size, and was created on Oct. 3, 2011. It is hereby incorporated by reference in its entirety.

BACKGROUND OF THE INVENTION

In the United States, colorectal cancer (CRC) is the third most prevalent and the second most deadly cancer in both sexes. Jemal et al., 58 CANCER J. FOR CLINICIANS 71-96 (2008). CRC is highly curable in its early, localized stages, with a 5-year survival rate exceeding 90%. Id. Unfortunately, 61% of new cases are already advanced at the time of diagnosis. Id. Delayed diagnosis occurs due to the asymptomatic nature of most early-stage CRCs; thus, the key to reducing deaths from CRC is periodic screening of the entire colon in the average risk population. Kahi et al., 135 GASTROENTEROLOGY 380-99 (2008). The current gold standard method for screening is colonoscopy. Id. However, invasive screening modalities, including colonoscopy, are not ideal for application to the asymptomatic population. Therefore, active investigations are now underway to discover noninvasive biomarkers, such as those found in stool, which could supplement or supplant colonoscopic screening.

Hypermethylation of CpG islands (CGIs) is a promising CRC biomarker with high potential for translation into non-invasive CRC detection modalities. CGI hypermethylation is a common epigenetic DNA abnormality that has been strongly linked to CRC. Fraga et al., 23 TRENDS IN GEN. 413-18 (2007). CGI hypermethylation possesses several advantages as a biomarker: 1) hypermethylation at multiple CGIs often exists in adenomas, suggesting its potential utility in early detection (Kim et al., 45 GENES, CHROMOSOMES & CANCER 781-89 (2006)); 2) only one assay per locus is generally needed, in contrast to gene mutation, which frequently require multiple assays due to the presence of mutational hotspots; and 3) quantitative methylation assays are applicable to low-integrity DNA commonly encountered in clinical specimens (Uhlmann et al., 23 ELECTROPHORESIS 4072-79 (2002); Fads et al., 28 NUCL. ACIDS RES. E32 (2000)). However, known cancer-specific methylation targets in the colon have in the past been identified based on their functional relevance to neoplastic progression, rather than on their merit as biomarkers, partly due to the previous lack of genome-wide, high-resolution methodologies for the direct analysis of methylation.

Recent technological advances now offer the ability to perform high-throughput, direct assays of DNA methylation. See Estecio et al., 17 GENOME RES. 1529-36 (2007). In this study, loyed a microarray-based direct scanning assay of DNA methylation to extensively search for CGI hypennethylation events, based purely on their performance as CRC biomarkers, for ultimate application to the average-risk population.

SUMMARY OF THE INVENTION

The present invention is based, at least in part, on the discovery of twelve DNA regions at which abnormal methylation occurs uniquely and prevalently in colorectal neoplasias. Real-time quantitative methylation-specific polymerase chain reaction (PCR) analysis of these DNA regions revealed that all of these methylation markers, as individual markers and multi-locus panel markers, can distinguish colorectal neoplasias from colonic mucosae of colonic neoplasia-free control cases with high accuracy. Abnormal methylation of these DNA regions was similarly prevalent in advanced adenomas, local colorectal carcinomas, and metastatic colorectal carcinomas, indicating the utility of these methylation markers for the detection of a wide range of diseases.

Accordingly, in one aspect, the present invention provides methods for qualifying colorectal cancer status including, but not limited to, diagnosis, prognosis, and risk stratification, in patients. In one embodiment, a method for diagnosing colorectal cancer (CRC) in a patient comprises the steps of (a) collecting a sample from the patient; (b) measuring the methylation levels of one or more biomarkers in the sample collected from the patient; and (c) comparing the methylation levels of the one or more biomarkers with predefined methylation levels of the same biomarkers that correlate to a patient having CRC and predefined methylation levels of the same biomarkers that correlate to a patient not having CRC, wherein a correlation to one of the predefined methylation levels provides the diagnosis.

In particular embodiments, the one or more biomarkers is selected from the group consisting of VSX2, NPTX1, BEND4, ALX3, miR34b, BTG4, GLP1R, HOMER2, GJC1, DOCK8, ZNF583, and NME4. Any of the foregoing biomarkers be used individually or in combination with one another or other known biomarkers to qualify disease status as described herein. In a specific embodiment, the one or more biomarkers comprise ALX3, miR34b or both. In another embodiment, the one or more biomarkers comprises VSX2. In yet another embodiment, the one or more biomarkers comprise VSX2, NPTX1, BEND4, miR34b, and HOMER2. In a further embodiment, the one or more biomarkers comprise VSX2, BEND4, GLP1R, HOMER2, GJC1, ZNF583. In such an embodiment, the one or more biomarkers further comprises NME4.

In another embodiments of the present invention, a method for diagnosing colorectal cancer (CRC) in a patient comprises the steps of (a) collecting a sample from the patient; (b) measuring the methylation levels of a panel of biomarkers in the sample collected from the patient, wherein the panel of biomarkers comprises VSX2, NPTX1, BEND4, ALX3, miR34b, BTG4, GLP1R, HOMER2, GJC1, DOCK8, ZNF583, and NME4; and (c) comparing the methylation levels of the panel of biomarkers with predefined methylation levels of the same panel of biomarkers that correlate to a patient having CRC and predefined methylation levels of the same panel of biomarkers that correlate to a patient not having CRC, wherein a correlation to one of the predefined methylation levels provides the diagnosis.

In an alternative embodiment, a method for diagnosing colorectal cancer (CRC) in a patient comprises the steps of (a) collecting a sample from the patient; (b) measuring the methylation levels of a panel of biomarkers in the sample collected from the patient, wherein the panel of biomarkers comprises VSX2 and ALX3; and (c) comparing the methylation levels of the panel of biomarkers with predefined methylation levels of the same biomarkers that correlate to a patient having CRC and predefined methylation levels of the same biomarkers that correlate to a patient not having CRC, wherein a correlation to one of the predefined methylation levels provides the diagnosis. In a specific embodiment, the panel of biomarkers further comprises miR34b. In another embodiment, the panel of biomarkers further comprises miR34b, NPTX1, BEND4, BTG4, GLP1R, HOMER2, GJC1, DOCK8, ZNF583, and NME4.

In a more specific embodiment, a method for diagnosing colorectal cancer (CRC) in a patient comprises the steps of (a) collecting a stool sample from the patient; (b) measuring the methylation levels of a panel of biomarkers in the stool sample collected from the patient, wherein the panel of biomarkers comprises ALX3 and miR34b; and (c) comparing the methylation levels of the panel of biomarkers with predefined methylation levels of the same biomarkers that correlate to a patient having CRC and predefined methylation levels of the same biomarkers that correlate to a patient not having CRC, wherein a correlation to one of the predefined methylation levels provides the diagnosis. In a further embodiment, the panel of biomarkers further comprises VSX2. In yet another embodiment, the panel of biomarkers further comprises VSX2, NPTX1, BEND4, BTG4, GLP1R, HOMER2, GJC1, DOCK8, ZNF583, and NME4.

In a specific embodiment, a method for determining the CRC status in a patient comprises the steps of (a) collecting a sample from the patient; (b) measuring the methylation levels of a panel of biomarkers in the sample collected from the patient, wherein the panel of biomarkers comprises VSX2, NPTX1, BEND4, ALX3, miR34b, BTG4, GLP1R, HOMER2, GJC1, DOCK8, ZNF583, and NME4; and (c) comparing the methylation levels of the panel of biomarkers with predefined methylation levels of the same panel of biomarkers that correlate to one or more CRC statuses selected from the group consisting of having CRC, not having CRC, progressing CRC, and regressing CRC, wherein a correlation to one of the predefined methylation levels determines the CRC status of the patient.

In certain embodiments of the present invention, the measuring step can comprise restriction enzyme digestion of the sample followed by real-time quantitative methylation-specific polymerase chain reaction. Further, the sample can be any suitable biological sample including, but not limited to, a stool, blood or serum sample. In a specific embodiment, the sample is a stool sample. In another embodiment, the sample is a serum sample.

In another aspect, the present invention provides kits useful for determining CRC status in a patient. In certain embodiments, a kit comprises (a) a substrate for collecting a biological sample from the patient; and (b) a means for measuring the methylation levels of one or more biomarkers selected from the group consisting of VSX2, NPTX1, BEND4, ALX3, miR34b, BTG4, GLP1R, HOMER2, GJC1, DOCK8, ZNF583, and NME4. In particular embodiments, the means for measuring the methylation levels of one or more biomarkers are oligonucleotide primers specific for amplifying methylated regions of the biomarkers.

BRIEF DESCRIPTION OF THE FIGURES

FIG. 3 presents the receiver operating characteristic (ROC) curve-based assessment of the methylation markers' diagnostic accuracy.

FIG. 4 is a table summarizing demographic data for cases studied in microarray/methylation-specific PCR (MSP) experiments and real-time quantitative MSP (qMSP) experiments.

FIG. 5 is a table showing ROC curve analysis data for the discrimination from control NCs.

FIG. 6 is a table showing the primer sequences used in the methylation-specific polymerase chain reaction (PCR) analyses.

FIG. 7 depicts the MCAM-derived (Methylated CpG island amplification coupled with microarray) methylation profiles of previously reported CRC methylation markers.

FIG. 8 shows validation results of twenty candidate loci for cancer-specific hypermethylation.

FIG. 9 demonstrates MCAM data reproducibility and reliability.

FIG. 12 depicts the performance of the stool methylation biomarker ALX3.

FIG. 14 shows the ALX gene sequence. ALX3 exon 1: Italics and underlined(reverse direction). ALX3 qMSP amplicon: Boxed. Bold font: the region whose cancer-associated methylation is verified in the current study using methylation microarray, bisulfite sequencing, or qMSP.

FIG. 15 shows the VSX2 gene sequence. VSX2 exon 1 and exon 2: italics and underlined. VSX2 qMSP amplicon: boxed. Bold font: the region whose cancer-associated methylation is verified in the current study using methylation microarray, bisulfite sequencing, or qMSP.

FIG. 16 shows the NPTX1 gene sequence. NPTX1 exon 1 and 2: italics and underlined (reverse direction). NPTX1 qMSP amplicon: boxed. Bold font: the region whose cancer-associated methylation is verified in the current study using methylation microarray, bisulfite sequencing, or qMSP.

FIG. 17 shows the BEND4 sequence. BEND4 exon 1 and exon 2: italics and underlined(reverse direction). BEND4 qMSP amplicon: boxed. Bold font: the region whose cancer-associated methylation is verified in the current study using methylation microarray, bisulfite sequencing, or qMSP.

FIG. 18 shows the miR34b and BTG4 gene sequences. miR34b exon: boxed and gray highlight (forward direction). BTG4 exon 1: italics and underlined (reverse direction). BTG4 qMSP amplicon: boxed. miR34b qMSP amplicon: -Gray highlight. Bold font: the region whose cancer-associated methylation is verified in the current study using methylation microarray, bisulfite sequencing, or qMSP. Nucleotide numbering is according to the UCSC hg18.

FIG. 19 shows the GLP1R gene sequences. GLP1R exon 1: italics and underlined. GLP1R qMSP amplicon: boxed. Bold font: the region whose cancer-associated methylation is verified in the current study using methylation microarray, bisulfite sequencing, or qMSP.

FIG. 20 shows the HOMER2 gene sequences. HOMER2 exon 1: italics and underlined (reverse direction). HOMER2 qMSP amplicon: boxed. Bold font: the region whose cancer-associated methylation is verified in the current study using methylation microarray, bisulfite sequencing, or qMSP.

FIG. 21 shows the GJC1 gene sequence. GJC1 exon 1: italics and underlined (reverse direction). GJC1 qMSP amplicon: boxed. Bold font: the region whose cancer-associated methylation is verified in the current study using methylation microarray, bisulfite sequencing, or qMSP.

FIG. 22 shows the DOCK8 gene sequence. DOCK8 exon 1: italics and underlined. DOCK8 qMSP amplicon: boxed. Bold font: the region whose cancer-associated methylation is verified in the current study using methylation microarray, bisulfite sequencing, or qMSP.

FIG. 23 shows the ZNF583 gene sequence. ZNF583 exon 1: italics and underlined. ZNF583 qMSP amplicon: boxed. Bold font: the region whose cancer-associated methylation is verified in the current study using methylation microarray, bisulfite sequencing, or qMSP.

FIG. 24 shows the NME4 gene sequence. NME4 exon 1: italics and underlined. NME4 qMSP amplicon: boxed. Bold font: the region whose cancer-associated methylation is verified in the current study using methylation microarray, bisulfite sequencing, or qMSP.

DETAILED DESCRIPTION OF THE INVENTION

Figure 1:
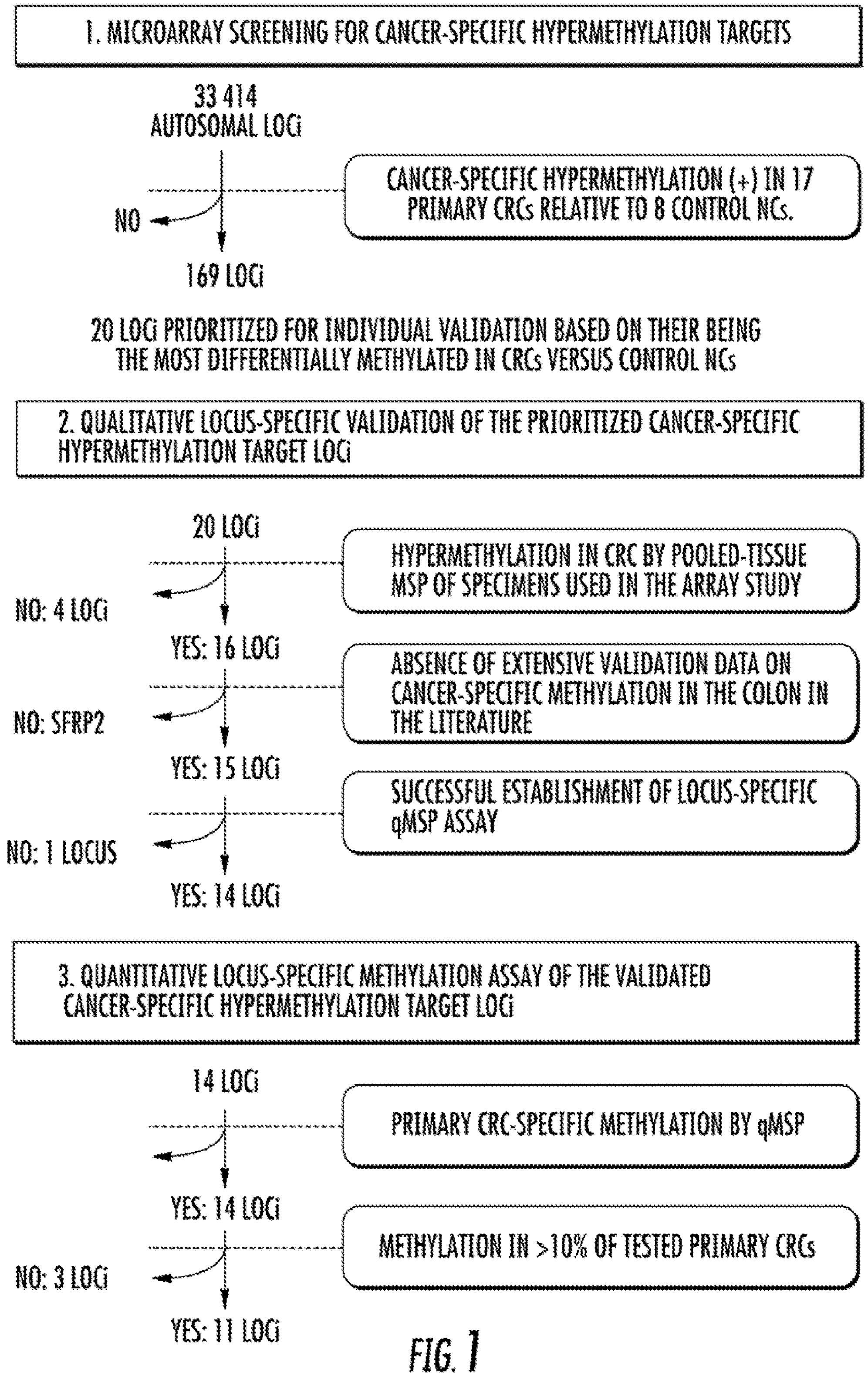
FIG. 1 is an outline of the experimental strategy and results.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly-understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

As used herein, the term "comparing" refers to making an assessment of how the proportion, level or cellular localization of one or more biomarkers in a sample from a patient relates to the proportion, level or cellular localization of the corresponding one or more biomarkers in a standard or control sample. For example, "comparing" may refer to assessing whether the proportion, level, or cellular localization of one or more biomarkers in a sample from a patient is the same as, more or less than, or different from the proportion, level, or cellular localization of the corresponding one or more biomarkers in standard or control sample. More specifically, the term may refer to assessing whether the proportion, level, or cellular localization of one or more biomarkers in a sample from a patient is the same as, more or less than, different from or otherwise corresponds (or not) to the proportion, level, or cellular localization of predefined biomarker levels that correspond to, for example, a patient having CRC, not having CRC, is responding to treatment for CRC, is not responding to treatment for CRC, is/is not likely to respond to a particular CRC treatment, or having/not having another disease or condition. In a specific embodiment, the term "comparing" refers to assessing whether the methylation level of one or more biomarkers of the present invention in a sample from a patient is the same as, more or less than, different from other otherwise correspond (or not) to methylation levels of the same biomarkers in a control sample (e.g., predefined levels that correlate to uninfected individuals, standard CRC levels, etc.).

As used herein, the terms "indicates" or "correlates" (or "indicating" or "correlating," or "indication" or "correlation," depending on the context) in reference to a parameter, e.g., a modulated proportion, level, or cellular localization in a sample from a patient, may mean that the patient has CRC. In specific embodiments, the parameter may comprise the methylation status or level of one or more biomarkers of the present invention. A particular set or pattern of methylation of one or more biomarkers may indicate that a patient has CRC (i.e., correlates to a patient having CRC). In other embodiments, a particular set or pattern of methylation of one or more biomarkers may be correlated to a patient being unaffected. In certain embodiments, "indicating," or "correlating," as used according to the present invention, may be by any linear or non-linear method of quantifying the relationship between methylation levels of biomarkers to a standard, control or comparative value for the assessment of the diagnosis, prediction of CRC or CRC progression, assessment of efficacy of clinical treatment, identification of a patient that may respond to a particular treatment regime or pharmaceutical agent, monitoring of the progress of treatment, and in the context of a screening assay, for the identification of an anti-CRC therapeutic.

The terms "patient," "individual," or "subject" are used interchangeably herein, and refer to a mammal, particularly, a human. The patient may have mild, intermediate or severe disease. The patient may be treatment naïve, responding to any form of treatment, or refractory. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The terms "measuring" and "determining" are used interchangeably throughout, and refer to methods which include obtaining a patient sample and/or detecting the methylation status or level of a biomarker(s) in a sample. In one embodiment, the terms refer to obtaining a patient sample and detecting the methylation status or level of one or more biomarkers in the sample. In another embodiment, the terms "measuring" and "determining" mean detecting the methylation status or level of one or more biomarkers in a patient sample. Measuring can be accomplished by methods known in the art and those further described herein including, but not limited to, quantitative polymerase chain reaction (PCR). The term "measuring" is also used interchangeably throughout with the term "detecting."

The term "methylation" refers to cytosine methylation at positions C5 or N4 of cytosine, the N6 position of adenine or other types of nucleic acid methylation. In vitro amplified DNA is unmethylated because in vitro DNA amplification methods do not retain the methylation pattern of the amplification template. However, "unmethylated DNA" or "methylated DNA" can also refer to amplified DNA whose original template was unmethylated or methylated, respectively. By "hypermethylation" or "elevated level of methylation" is meant an increase in methylation of a region of DNA (e.g., a biomarker of the present invention) that is considered statistically significant over levels of a control population. "Hypermethylation" or "elevated level of methylation" may refer to increased levels seen in a patient over time.

In particular embodiments, a biomarker would be unmethylated in a normal sample (e.g., normal or control tissue without disease, or normal or control body fluid, stool, blood, serum), most importantly in the healthy tissue the tumor originates from and/or in healthy stool, blood, serum, or other body fluid. In other embodiments, a biomarker would be hypermethylated in a large fraction of the tumors, preferably at a methylation frequency of at least about 50%, at least about 60%, at least about 70%, at least about 75%, at least about 80%, at least about 85%, at least about 90%, at least about 95%, or about 100%. In particular embodiment, the methylation status/levels of the biomarkers can be used to differentiate between different subtypes or tumor entities. Specific DNA methylation patterns may distinguish tumors with low and high metastatic potential making it possible to apply optimal treatment regimens early. In additional, methylation of certain DNA repair or damage response genes may be predictive of a positive therapeutic response.

A "methylation profile" refers to a set of data representing the methylation states or levels of one or more loci within a molecule of DNA from e.g., the genome of an individual or cells or sample from an individual. The profile can indicate the methylation state of every base in an individual, can comprise information regarding a subset of the base pairs (e.g., the methylation state of specific restriction enzyme recognition sequence) in a genome, or can comprise information regarding regional methylation density of each locus. In some embodiments, a methylation profile refers to the methylation states or levels of one or more biomarkers described herein, including VSX2, NPTX1, BEND4, ALX3, miR34b, BTG4, GLP1R, HOMER2, GJC1, DOCK8, ZNF583, and NME4.

The terms "methylation status" or "methylation level" refers to the presence, absence and/or quantity of methylation at a particular nucleotide, or nucleotides within a portion of DNA. The methylation status of a particular DNA sequence (e.g., a DNA biomarker or DNA region as described herein) can indicate the methylation state of every base in the sequence or can indicate the methylation state of a subset of the base pairs (e.g., of cytosines or the methylation state of one or more specific restriction enzyme recognition sequences) within the sequence, or can indicate information regarding regional methylation density within the sequence without providing precise information of where in the sequence the methylation occurs. The methylation status can optionally be represented or indicated by a "methylation value" or "methylation level." A methylation value or level can be generated, for example, by quantifying the amount of intact DNA present following restriction digestion with a methylation dependent restriction enzyme. In this example, if a particular sequence in the DNA is quantified using quantitative PCR, an amount of template DNA approximately equal to a mock treated control indicates the sequence is not highly methylated whereas an amount of template substantially less than occurs in the mock treated sample indicates the presence of methylated DNA at the sequence. Accordingly, a value, i.e., a methylation value, for example from the above described example, represents the methylation status and can thus be used as a quantitative indicator of methylation status. This is of particular use when it is desirable to compare the methylation status of a sequence in a sample to a threshold value.

A "methylation-dependent restriction enzyme" refers to a restriction enzyme that cleaves or digests DNA at or in proximity to a methylated recognition sequence, but does not cleave DNA at or near the same sequence when the recognition sequence is not methylated. Methylation-dependent restriction enzymes include those that cut at a methylated recognition sequence (e.g., Dpn1) and enzymes that cut at a sequence near but not at the recognition sequence (e.g., McrBC). For example, McrBC's recognition sequence is 5' RmC (N40-3000) RmC 3' where "R" is a purine and "mC" is a methylated cytosine and "N40-3000" indicates the distance between the two RmC half sites for which a restriction event has been observed. McrBC generally cuts close to one half-site or the other, but cleavage positions are typically distributed over several base pairs, approximately 30 base pairs from the methylated base. McrBC sometimes cuts 3' of both half sites, sometimes 5' of both half sites, and sometimes between the two sites. Exemplary methylation-dependent restriction enzymes include, e.g., McrBC, McrA, MrrA, BisI, GlaI and DpnI. One of skill in the art will appreciate that any methylation-dependent restriction enzyme, including homologs and orthologs of the restriction enzymes described herein, is also suitable for use in the present invention.

A "methylation-sensitive restriction enzyme" refers to a restriction enzyme that cleaves DNA at or in proximity to an unmethylated recognition sequence but does not cleave at or in proximity to the same sequence when the recognition sequence is methylated. Exemplary methylation-sensitive restriction enzymes are described in, e.g., McClelland et al., 22(17) Nucleic Acids Res. 3640-59 (1994) and http://rebase.neb.com. Suitable methylation-sensitive restriction enzymes that do not cleave DNA at or near their recognition sequence when a cytosine within the recognition sequence is methylated at position $C^5$ include, e.g., Mt II, Aci I, Acd I, Age I, Alu I, Ase I, Ase I, AsiS I, Bbe I, BsaA I, BsaH I, BsiE I, BsiW I, BsrF I, BssH II, BssK I, BstB I, BstN I, BstU I, Cla I, Eae I, Eag I, Fau I, Fse I, Hha I, HinP1 I, HinC II, Hpa II, Hpy99 I, HpyCH4 IV, Kas I, Mbo I, Mlu I, MapAl I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, and Zra I. Suitable methylation-sensitive restriction enzymes that do not cleave DNA at or near their recognition sequence when an adenosine within the recognition sequence is methylated at position $N^6$ include, e.g., Mbo I. One of skill in the art will appreciate that any methylation-sensitive restriction enzyme, including homologs and orthologs of the restriction enzymes described herein, is also suitable for use in the present invention. One of skill in the art will further appreciate that a methylation-sensitive restriction enzyme that fails to cut in the presence of methylation of a cytosine at or near its recognition sequence may be insensitive to the presence of methylation of an adenosine at or near its recognition sequence. Likewise, a methylation-sensitive restriction enzyme that fails to cut in the presence of methylation of an adenosine at or near its recognition sequence may be insensitive to the presence of methylation of a cytosine at or near its recognition sequence. For example, Sau3AI is sensitive (i.e., fails to cut) to the presence of a methylated cytosine at or near its recognition sequence, but is insensitive (i.e., cuts) to the presence of a methylated adenosine at or near its recognition sequence. One of skill in the art will also appreciate that some methylation-sensitive restriction enzymes are blocked by methylation of bases on one or both strands of DNA encompassing of their recognition sequence, while other methylation-sensitive restriction enzymes are blocked only by methylation on both strands, but can cut if a recognition site is hemi-methylated.

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of CRC. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, urine, saliva, stool and synovial fluid), solid tissue samples such as a biopsy specimen or tissue cultures or cells derived therefrom and the progeny thereof. In a specific embodiment, a sample comprises a blood sample. In another embodiment, a serum sample is used. In another embodiment, a sample comprises a stool sample. The definition also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

Various methodologies of the instant invention include a step that involves comparing a value, level, feature, characteristic, property, etc. to a "suitable control," referred to interchangeably herein as an "appropriate control" or a "control sample." A "suitable control," "appropriate control" or a "control sample" is any control or standard familiar to one of ordinary skill in the art useful for comparison purposes. In one embodiment, a "suitable control" or "appropriate control" is a value, level, feature, characteristic, property, etc., determined in a cell, organ, or patient, e.g., a control or normal cell, organ, or patient, exhibiting, for example, normal traits. For example, the biomarkers of the present invention may be assayed for their methylation level in a sample from an unaffected individual (UI) or a normal control individual (NC) (both terms are used interchangeably herein). In another embodiment, a "suitable control" or "appropriate control" is a value, level, feature, characteristic, property, etc. determined prior to performing a therapy (e.g., a CRC treatment) on a patient. In yet another embodiment, a transcription rate, mRNA level, translation rate, protein level, biological activity, cellular characteristic or property, genotype, phenotype, etc. can be determined prior to, during, or after administering a therapy into a cell, organ, or patient. In a further embodiment, a "suitable control" or "appropriate control" is a predefined value, level, feature, characteristic, property, etc. A "suitable control" can be a methylation profile of one or more biomarkers of the present invention that correlates to CRC, to which a patient sample can be compared. The patient sample can also be compared to a negative control, i.e., a methylation profile that correlates to not having CRC.

II. Hypermethylated Biomarkers and Detection Thereof

The biomarkers of the present invention are differentially methylated in CRC versus normal tissue. Such biomarkers can be used individually as diagnostic tool, or in combination as a biomarker panel. In particular embodiments, the biomarkers include VSX2, NPTX1, BEND4, ALX3, miR34b, BTG4, GLP1R, HOMER2, GJC1, DOCK8, ZNF583, and NME4. In fact, any combination of the biomarkers can be used as a diagnostic tool. The sequences of these biomarkers are publicly available, specifically, VSX2 (Gene Id No. 338917), NPTX1 (Gene Id No. 4884), BEND4 (Gene Id No. 389206), ALX3 (Gene Id No. 257), miR34b (Gene Id No. 407041), BTG4 (Gene Id No. 54766), GLP1R (Gene Id No. 2740), HOMER2 (Gene Id No. 9455), GJC1 (Gene Id No. 10052), DOCKS (Gene Id No. 81704), ZNF583 (Gene Id No. 27033), and NME4 (Gene Id No. 4833).

The DNA biomarkers of the present invention comprise fragments of a polynucleotide (e.g., regions of genome polynucleotide or DNA) which likely contain CpG island(s), or fragments which are more susceptible to methylation or demethylation than other regions of genome DNA. The term "CpG islands" is a region of genome DNA which shows higher frequency of 5'-CG-3' (CpG) dinucleotides than other regions of genome DNA. Methylation of DNA at CpG dinucleotides, in particular, the addition of a methyl group to position 5 of the cytosine ring at CpG dinucleotides, is one of the epigenetic modifications in mammalian cells. CpG islands often harbor the promoters of genes and play a pivotal role in the control of gene expression. In normal tissues CpG islands are usually unmethylated, but a subset of islands becomes methylated during the development of a disease (e.g., tumor development). Changes in DNA methylation patterns can occur in a developmental stage and tissue specific manner and often accompany tumor development, most notably in the form of CpG island hypermethylation. During tumorigenesis, both alleles of a tumor suppressor gene need to be inactivated by genomic changes such as chromosomal deletions or loss-of-function mutations in the coding region of a gene. As an alternative mechanism, transcriptional silencing by hypermethylation of CpG islands spanning the promoter regions of tumor suppressor genes is a common and important process in carcinogenesis. Since hypermethylation generally leads to inactivation of gene expression, this epigenetic alteration is considered to be a key mechanism for long-term silencing of tumor suppressor genes.

There are a number of methods that can be employed to measure, detect, determine, identify, and characterize the methylation status/level of a biomarker (i.e., a region/fragment of DNA or a region/fragment of genome DNA (e.g., CpG island-containing region/fragment)) in the development of a disease (e.g., colorectal cancer) and thus diagnose the onset, presence or status of the disease.

In some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. Alternatively, the method can encompass amplifying intact DNA after restriction enzyme digestion, thereby only amplifying DNA that was not cleaved by the restriction enzyme in the area amplified. See, e.g., U.S. Pat. No. 7,910,296; U.S. Pat. No. 7,901,880; and U.S. Pat. No. 7,459,274. In some embodiments, amplification can be performed using primers that are gene specific. Alternatively, adaptors can be added to the ends of the randomly fragmented DNA, the DNA can be digested with a methylation-dependent or methylation-sensitive restriction enzyme, intact DNA can be amplified using primers that hybridize to the adaptor sequences. In this case, a second step can be performed to determine the presence, absence or quantity of a particular gene in an amplified pool of DNA. In some embodiments, the DNA is amplified using real-time, quantitative PCR.

In other embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

The quantity of methylation of a locus of DNA can be determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using at least one methylation-sensitive or methylation-dependent restriction enzyme under conditions that allow for at least some copies of potential restriction enzyme cleavage, sites in the locus to remain uncleaved and subsequently quantifying the remaining intact copies and comparing the quantity to a control, average methylation density of a locus can be determined. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample. Such assays are disclosed in, e.g., U.S. Pat. No. 7,910,296.

Quantitative amplification methods (e.g., quantitative PCR or quantitative linear amplification) can be used to quantify the amount of intact DNA within a locus flanked by amplification primers following restriction digestion. Methods of quantitative amplification are disclosed in, e.g., U.S. Pat. No. 6,180,349; U.S. Pat. No. 6,033,854; and U.S. Pat. No. 5,972,602, as well as in, e.g., DeGraves, et al., 34(1) Biotechniques 106-15 (2003); Deiman B, et al., 20(2) Mol. Biotechnol. 163-79 (2002); and Gibson et al., 6 Genome Research 995-1001 (1996). Amplifications may be monitored in "real time."

Additional methods for detecting DNA methylation can involve genomic sequencing before and after treatment of the DNA with bisulfite. See, e.g., Frommer et al., 89 Proc. Natl. Acad. Sci. USA 1827-31 (1992). When sodium bisulfite is contacted to DNA, unmethylated cytosine is converted to uracil, while methylated cytosine is not modified. In some embodiments, restriction enzyme digestion of PCR products amplified from bisulfite-converted DNA is used to detect DNA methylation. See, e.g., Xiong & Laird, 25 Nucleic Acids Res. 2532-34 (1997); and Sadri & Hornsby, 24 Nucl. Acids Res. 5058-59 (1996).

In some embodiments, a MethyLight assay is used alone or in combination with other methods to detect DNA methylation. See, Eads et al., 59 Cancer Res. 2302-06 (1999). Briefly, in the MethyLight process genomic DNA is converted in a sodium bisulfite reaction (the bisulfite process converts unmethylated cytosine residues to uracil). Amplification of a DNA sequence of interest is then performed using PCR primers that hybridize to CpG dinucleotides. By using primers that hybridize only to sequences resulting from bisulfite conversion of unmethylated DNA, (or alternatively to methylated sequences that are not converted) amplification can indicate methylation status of sequences where the primers hybridize. Similarly, the amplification product can be detected with a probe that specifically binds to a sequence resulting from bisulfite treatment of a unmethylated (or methylated) DNA. If desired, both primers and probes can be used to detect methylation status. Thus, kits for use with MethyLight can include sodium bisulfite as well as primers or detectably-labeled probes (including but not limited to Taqman or molecular beacon probes) that distinguish between methylated and unmethylated DNA that have been treated with bisulfite. Other kit components can include, e.g., reagents necessary for amplification of DNA including but not limited to, PCR buffers, deoxynucleotides; and a thermostable polymerase.

In other embodiments, a Methylation-sensitive Single Nucleotide Primer Extension (Ms-SNuPE) reaction is used alone or in combination with other methods to detect DNA methylation. See Gonzalgo & Jones, 25 Nucleic Acids Res. 2529-31 (1997). The Ms-SNuPE technique is a quantitative method for assessing methylation differences at specific CpG sites based on bisulfite treatment of DNA, followed by single-nucleotide primer extension. Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Typical reagents (e.g., as might be found in a typical Ms-SNuPE-based kit) for Ms-SNuPE analysis can include, but are not limited to: PCR primers for specific gene (or methylation-altered DNA sequence or CpG island); optimized PCR buffers and deoxynucleotides; gel extraction kit; positive control primers; Ms-SNuPE primers for a specific gene; reaction buffer (for the Ms-SNuPE reaction); and detectably-labeled nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

In further embodiments, a methylation-specific PCR reaction is used alone or in combination with other methods to detect DNA methylation. A methylation-specific PCR assay entails initial modification of DNA by sodium bisulfite, converting all unmethylated, but not methylated, cytosines to uracil, and subsequent amplification with primers specific for methylated versus unmethylated DNA. See, Herman et al., 93 Proc. Natl. Acad. Sci. USA 9821-26, (1996); and U.S. Pat. No. 5,786,146.

Additional methylation detection methods include, but are not limited to, methylated CpG island amplification (see, Toyota et al., 59 Cancer Res. 2307-12 (1999)) and those methods described in, e.g., U.S. Pat. No. 7,553,627; U.S. Pat. No. 6,331,393; U.S. patent Ser. No. 12/476,981; U.S. Patent Publication No. 2005/0069879; Rein. et al., 26(10) Nucleic Acids Res. 2255-64 (1998); and Olek et al., 17(3) Nat. Genet. 275-6 (1997).

III. Determination of a Patient's Colorectal Cancer Status

The present invention relates to the use of biomarkers to detect CRC. More specifically, the biomarkers of the present invention can be used in diagnostic tests to determine, qualify, and/or assess CRC status, for example, to diagnose CRC, in an individual, subject or patient. More specifically, the biomarkers to be detected in diagnosing CRC include, but are not limited to, VSX2, NPTX1, BEND4, ALX3, miR34b, BTG4, GLP1R, HOMER2, GJC1, DOCK8, ZNF583, and NME4. Other biomarkers known in the relevant art may be used in combination with the biomarkers described herein including, but not limited to, BMP3, GATA4, GATA5, H1C1, HPP1, ITGA4, MAL, MGMT, NDRG4, NELL1, OSMR, RASSF2, SFRP2, TFPI2, VIM, AND WIF1.

A. Biomarker Panels

The biomarkers of the present invention can be used in diagnostic tests to assess, determine, and/or qualify (used interchangeably herein) CRC status in a patient. The phrase "CRC status" includes any distinguishable manifestation of the disease, including non-disease. For example, CRC status includes, without limitation, the presence or absence of CRC in a patient), the risk of developing CRC, the stage of CRC, the progress of CRC (e.g., progress of CRC over time) and the effectiveness or response to treatment of CRC (e.g., clinical follow up and surveillance of CRC after treatment).

Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker panels of the present invention may show a statistical difference in different CRC statuses of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9.

The biomarkers are differentially methylated in UI (or NC) and CRC, and, therefore, are useful in aiding in the determination of CRC status. In certain embodiments, the biomarkers are measured in a patient sample using the methods described herein and compared, for example, to predefined biomarker levels and correlated to CRC status. In particular embodiments, the measurement(s) may then be compared with a relevant diagnostic amount(s), cut-off(s), or multivariate model scores that distinguish a positive CRC status from a negative CRC status. The diagnostic amount(s) represents a measured amount of a hypermethylated biomarker(s) above which or below which a patient is classified as having a particular CRC status. For example, if the biomarker(s) is/are hypermethylated compared to normal during CRC, then a measured amount(s) above the diagnostic cutoff(s) provides a diagnosis of CRC. Alternatively, if the biomarker(s) is/are hypomethylated in a patient, then a measured amount(s) at or below the diagnostic cutoff(s) provides a diagnosis of non-CRC. As is well understood in the art, by adjusting the particular diagnostic cut-offs) used in an assay, one can increase sensitivity or specificity of the diagnostic assay depending on the preference of the diagnostician. In particular embodiments, the particular diagnostic cut-off can be determined, for example, by measuring the amount of biomarker hypermethylation in a statistically significant number of samples from patients with the different CRC statuses, and drawing the cut-off to suit the desired levels of specificity and sensitivity.

Indeed, as the skilled artisan will appreciate there are many ways to use the measurements of the methylation status of two or more biomarkers in order to improve the diagnostic question under investigation. In a quite simple, but nonetheless often effective approach, a positive result is assumed if a sample is hypermethylation positive for at least one of the markers investigated.

Furthermore, in certain embodiments, the methylation values measured for markers of a biomarker panel are mathematically combined and the combined value is correlated to the underlying diagnostic question. Methylated biomarker values may be combined by any appropriate state of the art mathematical method. Well-known mathematical methods for correlating a marker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in a correlating methylation status of a biomarker combination of the present invention, e.g. to diagnose CRC, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. of Computational and Graphical Statistics 475-511 (2003); Friedman, J. H., 84 J. of the American Statistical Association 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 Machine Learning 5-32 (2001); Pepe, M. S., The Statistical Evaluation of Medical Tests for Classification and Prediction, Oxford Statistical Science Series, 28 (2003); and Duda, R. O., Hart, P. E., Stork, D. O., Pattern Classification, Wiley Interscience, 2nd Edition (2001).

B. Determining Risk of Developing CRC

In a specific embodiment, the present invention provides methods for determining the risk of developing CRC in a patient. Biomarker methylation percentages, amounts or patterns are characteristic of various risk states, e.g., high, medium or low. The risk of developing CRC is determined by measuring the methylation status of the relevant biomarkers and then either submitting them to a classification algorithm or comparing them with a reference amount, i.e., a predefined level or pattern of methylated (and/or unmethylated) biomarkers that is associated with the particular risk level.

C. Determining CRC Severity

In another embodiment, the present invention provides methods for determining the severity of CRC in a patient. Each stage of CRC-stage 0, stage I, stage II, stage III, stage IV—has a characteristic level of hypermethylation of a biomarker or relative hypermethylated levels of a set of biomarkers (a pattern). The severity of CRC is determined by measuring the methylation status of the relevant biomarkers and then either submitting them to a classification algorithm or comparing them with a reference amount, i.e., a predefined methylation level or pattern of methylated biomarkers that is associated with the particular stage.

D. Determining CRC Prognosis

In one embodiment, the present invention provides methods for determining the course of CRC in a patient. CRC course refers to changes in CRC status over time, including CRC progression (worsening) and CRC regression (improvement). Over time, the amount or relative amount (e.g., the pattern) of hypermethylation of the biomarkers changes.

For example, hypermethylation of biomarker "X" and "Y" may be increased with CRC. Therefore, the trend of these biomarkers, either increased or decreased methylation over time toward CRC or non-CRC indicates the course of the disease. Accordingly, this method involves measuring the methylation level or status of one or more biomarkers in a patient at least two different time points, e.g., a first time and a second time, and comparing the change, if any. The course of CRC is determined based on these comparisons.

E. Patient Management

In certain embodiments of the methods of qualifying CRC status, the methods further comprise managing patient treatment based on the status. Such management includes the actions of the physician or clinician subsequent to determining CRC status. For example, if a physician makes a diagnosis of CRC, then a certain regime of monitoring would follow. An assessment of the course of CRC using the methods of the present invention may then require a certain CRC therapy regimen. Alternatively, a diagnosis of non-CRC might be followed with further testing to determine a specific disease that the patient might be suffering from. Also, further tests may be called for if the diagnostic test gives an inconclusive result on CRC status.

F. Determining Therapeutic Efficacy of Pharmaceutical Drug

In another embodiment, the present invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of hypermethylation of one or more of the biomarkers of the present invention may change toward a non-CRC profile. Therefore, one can follow the course of the methylation status of one or more biomarkers in the patient during the course of treatment. Accordingly, this method involves measuring methylation levels of one or more biomarkers in a patient receiving drug therapy, and correlating the levels with the CRC status of the patient (e.g., by comparison to predefined methylation levels of the biomarkers that correspond to different CRC statuses). One embodiment of this method involves determining the methylation levels of one or more biomarkers at at least two different time points during a course of drug therapy, e.g., a first time and a second time, and comparing the change in methylation levels of the biomarkers, if any. For example, the methylation levels of one or more biomarkers can be measured before and after drug administration or at two different time points during drug administration. The effect of therapy is determined based on these comparisons. If a treatment is effective, then the methylation status of one or more biomarkers will trend toward normal, while if treatment is ineffective, the methylation status of one or more biomarkers will trend toward CRC indications.

G. Generation of Classification Algorithms for Qualifying CRC Status

In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition (e.g., diseased versus non-diseased).

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al. "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating System, such as a Unix, Windows® or Linux™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc.

The learning algorithms described above are useful both for developing classification algorithms for the biomarker biomarkers already discovered, and for finding new biomarker biomarkers. The classification algorithms, in turn, form the base for diagnostic tests by providing diagnostic values (e.g., cut-off points) for biomarkers used singly or in combination.

H. Kits for the Detection of CRC Biomarker Biomarkers

In another aspect, the present invention provides kits for qualifying CRC status, which kits are used to detect or measure the methylation status/levels of the biomarkers described herein. Such kits can comprise at least one polynucleotide that hybridizes to at least one of the diagnostic biomarker sequences of the present invention and at least one reagent for detection of gene methylation. Reagents for detection of methylation include, e.g., sodium bisulfite, polynucleotides designed to hybridize to a sequence that is the product of a biomarker sequence of the invention if the biomarker sequence is not methylated (e.g., containing at least one C→U conversion), and/or a methylation-sensitive or methylation-dependent restriction enzyme. The kits can further provide solid supports in the form of an assay apparatus that is adapted to use in the assay. The kits may further comprise detectable labels, optionally linked to a polynucleotide, e.g., a probe, in the kit. Other materials useful in the performance of the assays can also be included in the kits, including test tubes, transfer pipettes, and the like. The kits can also include written instructions for the use of one or more of these reagents in any of the assays described herein.

In some embodiments, the kits of the invention comprise one or more (e.g., I, 2, 3, 4, or more) different polynucleotides (e.g., primers and/or probes) capable of specifically amplifying at least a portion of a DNA region of a biomarker of the present invention including VSX2, NPTX1, BEND4, ALX3, miR34b, BTG4, GLP1R, HOMER2, GJC1, DOCK8, ZNF583, and NME4. Optionally, one or more detectably-labeled polypeptides capable of hybridizing to the amplified portion can also be included in the kit. In some embodiments, the kits comprise sufficient primers to amplify 2, 3, 4, 5, 6, 7, 8, 9, 10, or more different DNA regions or portions thereof, and optionally include detectably-labeled polynucleotides capable of hybridizing to each amplified DNA region or portion thereof. The kits further can comprise a methylation-dependent or methylation sensitive restriction enzyme and/or sodium bisulfite.

In some embodiments, the kits comprise sodium bisulfite, primers and adapters (e.g., oligonucleotides that can be ligated or otherwise linked to genomic fragments) for whole genome amplification, and polynucleotides (e.g., detectably-labeled polynucleotides) to quantify the presence of the converted methylated and or the converted unmethylated sequence of at least one cytosine from a DNA region of a biomarker of the present invention including VSX2, NPTX1, BEND4, ALX3, miR34b, BTG4, GLP1R, HOMER2, GJC1, DOCK8, ZNF583, and NME4.

In some embodiments, the kits comprise methylation sensing restriction enzymes (e.g., a methylation-dependent restriction enzyme and/or a methylation-sensitive restriction enzyme), primers and adapters for whole genome amplification, and polynucleotides to, quantify the number of copies of at least a portion of a DNA region of a biomarker of the present invention including VSX2, NPTX1, BEND4, ALX3, miR34b, BTG4, GLP1R, HOMER2, GJC1, DOCK8, ZNF583, and NME4.

In some embodiments, the kits comprise a methylation binding moiety and one or more polynucleotides to quantify the number of copies of at least a portion of a DNA region of a biomarker of the present invention including VSX2, NPTX1, BEND4, ALX3, miR34b, BTG4, GLP1R, HOMER2, GJC1, DOCK8, ZNF583, and NME4. A methylation binding moiety refers to a molecule (e.g., a polypeptide) that specifically binds to methyl-cytosine. Examples include restriction enzymes or fragments thereof that lack DNA cutting activity but retain the ability to bind methylated DNA, antibodies that specifically bind to methylated DNA, etc.).

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Patients and Nucleic Acid Preparation.

Sporadic CRC tissues were obtained during surgery. Adenomas were obtained during colonoscopy. All adenomas were R1 cm in diameter or exhibited advanced histology (i.e., tubulovillous adenomas, villous adenomas, and adenomas with focal highgrade dysplasia). Recurrent CRC patients, polyposis- or inflammatory bowel disease (CRC)-associated CRC patients, and patients who had ever undergone chemotherapy for CRC or other neoplasias before sampling were excluded from the study.

Three types of non-neoplastic colonic mucosae (NCs) were studied: NCs from CRC patients (CRC-NCs), NCs from neoplasia-free subjects who were 40 years of age or older (control NCs), and NCs from neoplasia-free subjects who were younger than 40 years of age (young control NCs). Neoplasia-free subjects were those who underwent screening colonoscopy but presented no colonoscopic abnormalities and possessed no history of colonic neoplasia, CRC, or chemotherapy for any malignancies.

Tissue acquisition was conducted under a protocol approved by the institutional review board at the Johns Hopkins University (Baltimore, Md., USA). Written consent was obtained from all patients enrolled after full explanation of the purpose and nature of all procedures used. Genomic DNA was extracted from snap-frozen tissues using a DNeasy kit (Qiagen). Demographic data for cases studied in microarray/methylation-specific PCR (MSP) experiments and real-time quantitative MSP (qMSP) experiments are summarized in FIG. 4. All specimens interrogated in microarray experiments were also included in qMSP experiments. CpG island methylator phenotype (CIMP) status of each tumor was determined based on qMSP measurement of the methylation status of five loci (RUNX3, SOCS 1, NEUROG1, IGF2, and CACNA1G). Weisenberger et al., 38 787-93 (2006). Neoplasias demonstrating methylation at ≥3 or <3 of the five loci were classified as CIMP-positive (+) or -negative (−) respectively.

Methylated CpG Island Amplification Coupled with Microarray Analysis.

Figure 9A:
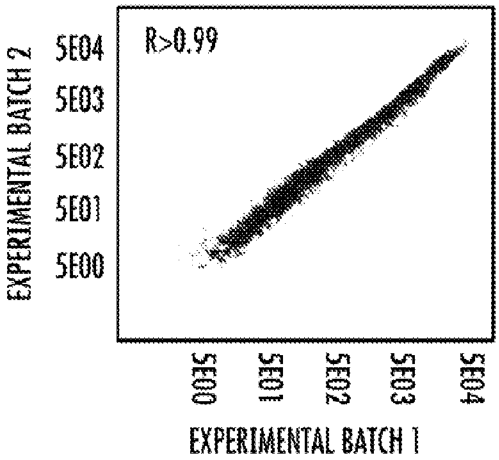
In FIG. 9A, the raw data for two experimental batches of a specimen demonstrated extremely high correlation (R>0.99). Each data point represents a probe. The MCAM experiment for these two batches (i.e., DNA processing, array hybridization, and array scanning) was performed on separate days, two weeks apart.
Figure 9B:
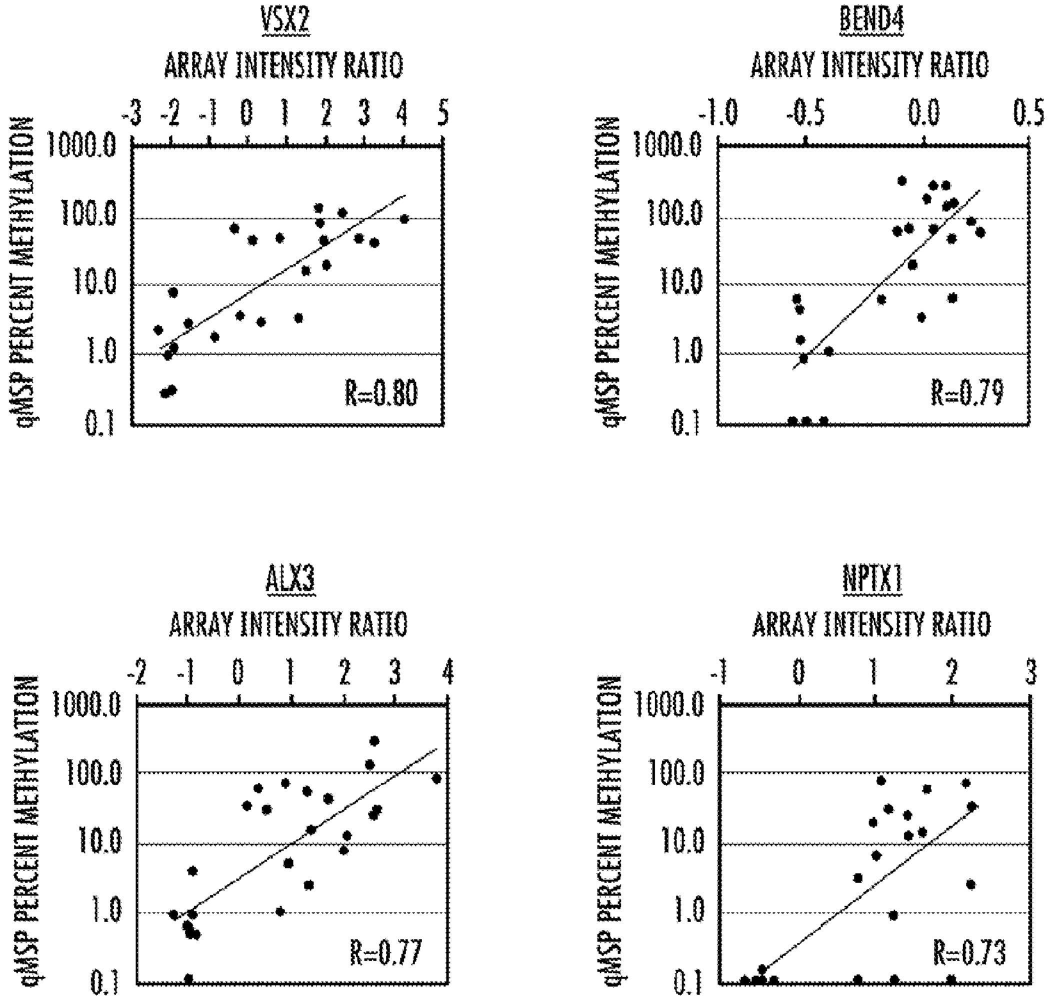
In FIG. 9B, methylation measurements by MCAM (X-axis) and qMSP (Y-axis) are plotted for individual specimens at four loci. The results from MCAM and qMSP assays at these loci correlated well (R>0.70, p<0.0001) despite of the markedly distinctive basis of methylation measurement for MCAM vs. qMSP (e.g., restriction enzyme digestion vs. bisulfite conversion, single CpG methylation status vs. continuous methylation of all or nearly all CpGs within a region that is 70-120 bases in length).

Methylated CpG island amplification coupled with microarray (MCAM) was conducted using the isoschizomers SmaI and XmaI. See Estecio et al., 17 GENOME RES. 1529-36 (2007). 244K Human CGI microarrays (Agilent Technologies, Santa Clara, Calif., USA) were employed as an array platform. Using this methodology, the methylation status of 34 396 SmaI-XmaI restriction fragments that covered to 50.4% of all CGIs in the genome was assessed. Ssst-treated fully methylated DNA was used as a control DNA. Normalized log 2 array intensity ratio to control fully methylated DNA at each locus (log 2 array ratio) was used to represent locus methylation level. The robustness of this MCAM methodology was verified as follows: two separate MCAM experimental batches of a specimen displayed markedly high reproducibility (R>0.99; FIG. 9A) and methylation measurements by MCAM and qMSP were significantly correlated (R>0.70; FIG. 9B). Further methodological details are described in the Supplementary Materials and Methods section below.

Selection of Candidate Cancer-Specific Methylation Targets Based on the MCAM Data.

The criteria for autosomal cancer-specific methylation events in the colon were as follows: 1) mean log 2 array ratio for CRCs greater than that for control NCs by more than 0.5 at t-test P<0.01; 2) no overlap in log 2 array ratio between any CRCs versus any control NCs; 3) mean log 2 array ratio for CRCs greater than the lower 95% confidence limits of mean normalized log 2 array ratios for array normalization control probes (see Supplementary Materials and Methods below); and 4) mean log 2 array ratio for control NCs greater than the upper 95% confidence limits of mean log 2 array ratios for normalization control probes.

Methylation-Specific PCR.

MSP analyses were performed on pooled primary CRC-derived DNAs versus pooled control NC-derived DNAs. Specimens analyzed by MSP were identical to those analyzed by MCAM. Thirty-seven cycles of PCR amplification were carried out, and PCR product quantity was measured by gel electrophoresis using a GelDoc XR system (Bio-Rad). Both the lack of amplification from unmethylated control DNA and efficient amplification from fully methylated control DNA were verified. A given locus was classified as hypermethylated in CRC when the visualized PCR product from pooled CRCs was greater than five-fold more abundant than from pooled control NCs. Primer sequences are shown in FIG. 6, see Supplementary Materials and Methods below. Real-Time Quantitative MSP. qMSP was performed by the same primer set as for MSP and a locus-specific TaqMan probe for each locus. The fraction of densely methylated DNA molecules at each locus (i.e., percent methylation ratio (PMR)) was calculated as described. See Mori et al., 131 GASTROENTEROLOGY 797-808 (2006). TaqMan probe sequences are provided in FIG. 6.

Statistical Analysis.

A P value of 0.05 was used as the cut off for statistical significance. Normalized MCAM data were assessed by Student's t-tests, unless otherwise stated. qMSP data were analyzed by Mann-Whitney U test, unless otherwise stated, due to their non-normal distribution. Receiver operator characteristic (ROC) curve analysis was applied to evaluate the diagnostic performance of PMR data at each locus. ROC curves were generated using the PMR data for each locus as a continuous input variable. The non-parametric Delong-Clarke-Pearson method was applied to compare areas under ROC curves (AUROCs). See DeLong et al., 44 BIOMETRICS 837-45 (1988). Forward stepwise discriminant analysis and fivefold cross validation were employed to generate diagnostic models based on methylation levels at multiple loci.

Supplementary Methods and Materials

Methylated CpG Island Amplification (MCA).

Selective enrichment of methylated DNA in each sample DNA was conducted by utilizing the MCA methodology. In MCA, the methylated DNA-specific amplification was carried out based upon the serial digestion with a set of isoschizomers, methylation-sensitive SmaI and methylation-insensitive XmaI, followed by XmaI-digested fragment-specific linker PCR. In brief, 5 μg of DNA was digested with SmaI and then dephosphorylated using Antarctic phosphatase. DNA was subsequently subjected to digestion with XmaI followed by column-purification with the QIAquick PCR purification kit (Qiagen). The purified DNA was then ligated to linker by using T4 DNA ligase and column-purified again. The linker was prepared by annealing the following two oligomers: RMCA24 (5'-CCACCGCCATCCGAGCCTTTCTGC-3') (SEQ ID NO:43) and RMCA12 (5'-CCGGGCAGAAAG-3) (SEQ ID NO:44). One hundred ng of linker-ligated DNA was PCR-amplified in a 100 μl reaction mix containing 100 μM of RMCA24 as described previously. See Estecio et al., 17 GENOME RES. 1529-36 (2007).

MCA Microarray.

The 244K Human CpG Island microarray (Agilent Technologies, Santa Clara, Calif.) was used as the array platform. The hybridization targets were prepared by labeling 5 μg of MCA-processed DNA with Cy-5 or Cy-3 dUTP using the random primer method (BioPrime DNA Labeling System, Invitrogen, Carlsbad, Calif.). Array hybridization and washing was carried out according to the Agilent CGH microarray protocol. Array raw data acquisition was conducted using an Agilent G2565BA microarray scanner and Feature Extraction Software (Agilent) according to the array-CGH data extraction protocol.

Array Data Processing.

Raw data processing included background subtraction and LOESS normalization using the LIMMA scripts. See Wettenhall et al., 20 Bioinformatics 3705-06 (2004). LOESS normalization was performed based on the probes whose corresponding SmaI-XmaI fragment length were greater than 5 kb and thus were not susceptible to PCR-amplification regardless of the methylation status, as was described previously. See Estecio et al., 17 Genome Res. 1529-36 (2007). The normalized log 2 intensity ratio to the fully methylated control DNA, CpGenome Universal Methylated DNA (Millipore, Billerica, Mass.), at each locus was used as the value representing the locus methylation status. When multiple probes corresponded to a SmaI-XmaI fragment, the median of these probes were used as the representative value. The data for probes whose corresponding SmaI-XmaI fragments were 60-2000 nucleotides in length (i.e., optimal size for PCR amplification) were used for the evaluation of loci methylation status. Id. Fragments were dropped from analyses when only single corresponding probe presented on the array and the raw signal intensity for this probe was low (i.e., <500 AU) in fully methylated control DNA. Id. As the results, this MCAM protocol enabled the methylation status assessment of 34,396 SmaI-XmaI restriction fragments that corresponded to 14,213 CGIs (50.4% of all CGIs in the genome). Twenty percent of these SmaI-XmaI fragments located outside of known coding or non-coding genes, and the remaining fragments located proximal to the transcriptional start sites (−2,000 to +500 bases, 63%) or transcribed regions (17%). Annotation of the probes and SmaI-XmaI fragments was based upon the Human Genome Assembly version 18. Array raw data processing was conducted using a LIMMA library-based R script and an sql script.

Results

A genome-wide search was conducted for novel targets of CRC-specific hypermethylation by employing methylated DNA microarray-based scanning of primary CRCs followed by locus-specific qMSPbased validation. See FIG: 1. A total of 33,414 autosomal CGI loci were interrogated. After performing qualitative validation in the tissue cohort that was used in the microarray analysis, quantitative validation was carried out in a larger tissue cohort utilizing locus-specific qMSP-based assays.

Example 1

Microarray Screening

Methylated DNA microarray analysis was performed by MCAM methodology. See Estecio et al., 17 Genome Res. 1529-36 (2007). Seventeen primary CRCs and eight non-neoplastic colonic mucosae (NCs) from colonic neoplasia-free control subjects who were 40 years of age or older (control NCs) were analyzed (FIG. 6). Aged control individuals were studied to avoid mistakenly identifying age-associated hypermethylation targets as neoplasiaspecific hypermethylation events. Matching nonneoplastic colonic tissues from CRC cases (hereinafter referred to as NC-CRC) were not used as controls, since these tissues may already carry hypermethylation events linked to an increased risk of carcinogenic progression due to a “field defect.” See Belshaw et al., 31 Carcinogenesis 1158-63 (2010), Svrcek et al., 59 Gut 1516-26 (2010), Nosho et al., 137 Gastroenterology 1609-20 (2009), and Shen et al., 97 J. Nat. Cancer Inst. 1330-38 (2005).

Figure 10:
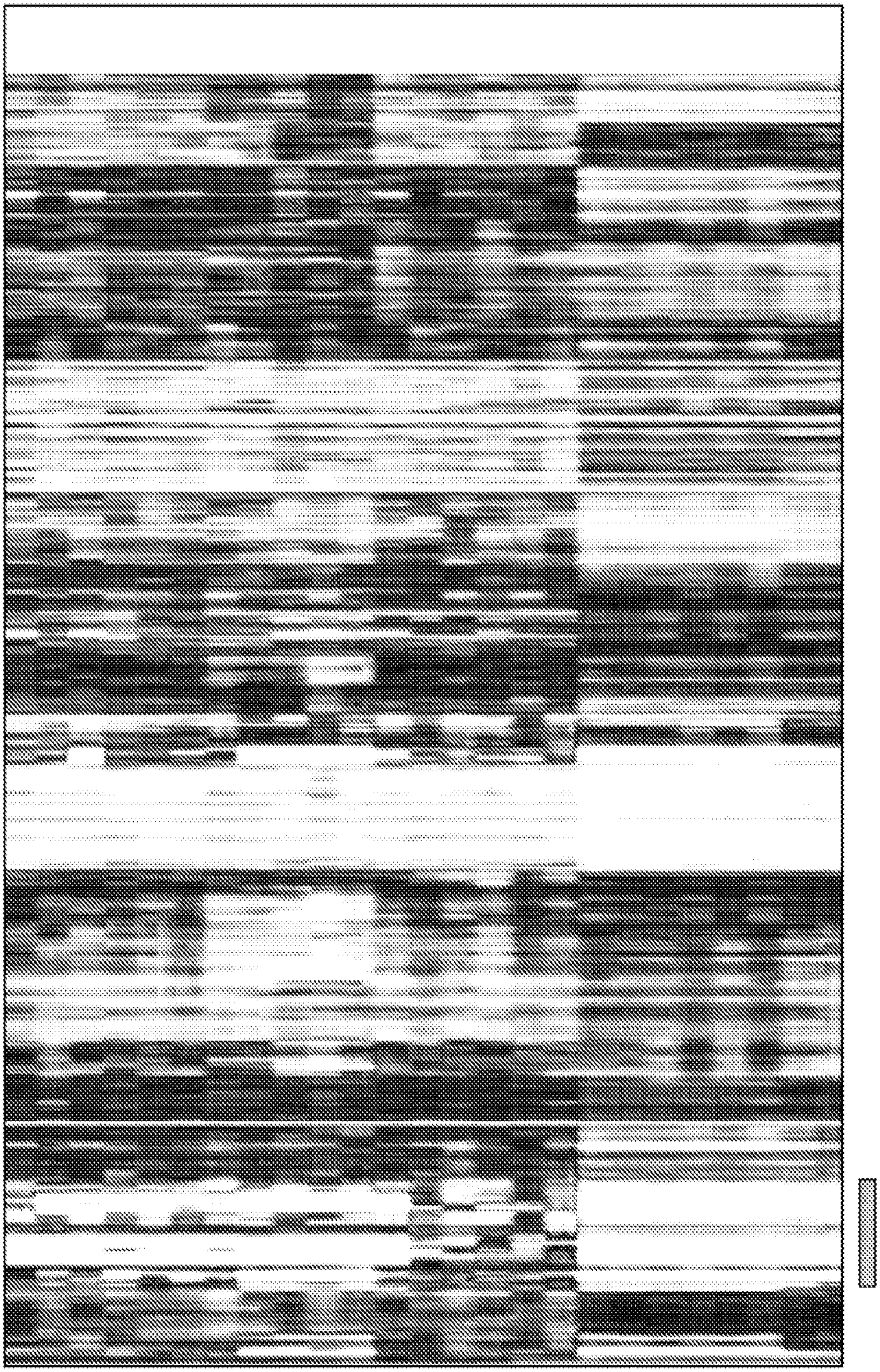
FIG. 10 presents the cluster analysis of the methylation microarray data. The k-mean Clustergram is shown for the analysis of 18,892 autosomal loci that tended to be differentially methylated between 17 CRCs and 8 control NCs (inclusion criteria: t-test p<0.1). The y-axis represents loci alignment, while the x-axis represents tissue alignment: orange, control NCs; pink, CIMP(+) CRCs (CpG island methylator phenotype, CIMP); blue, CIMP(−) CRCs. As expected, control NCs clustered separately from CRCs, and CIMP(−) CRCs formed a cluster separately from most CIMP(−) CRCs. Gray vertical bars indicate the clusters of loci whose methylation status in CIMP(+) CRCs differs from that of CIMP(−) CRCs.

The majority of analyzed loci tended to be differentially methylated in CRCs relative to control NCs (P>0.1:18,892 of 33,414 analyzed autosomal loci). Cluster analyses of these 18,892 loci showed separation of CRCs from control NCs (FIG. 10, see Supplementary Materials and Methods above). As expected, CIMP (+) and CIMP (−) CRCs clustered separately, with the exception of one CIMP (−) CRC that was methylated at two CIMP marker loci and clustered with CIMP (+) CRCs. Candidate autosomal loci were selected for colonic neoplasia-specific methylation based on significant hypermethylation in CRCs relative to control NCs by a mean log 2 array intensity ratio difference ≥0.5. To eliminate markers that would likely to exhibit low sensitivity and specificity in CRC diagnosis, loci whose methylation level overlapped between CRCs and control NCs were excluded (i.e., loci showing hypermethylation in CRC at which minimum log 2 array ratio for CRCs is smaller than maximum log 2 array ratio for control NCs, and vice versa). Based on these criteria, 169 loci were designated as candidate loci showing neoplasiaspecific hypermethylation in colonic mucosae.

One of these 169 loci was SFRP2, a previously published target of cancer-specific methylation in the colon, whose methylation has been reported in 75-90% of stool DNAs from CRC patients by multiple groups. See Nagasaka et al., 101 J. Nat. Cancer Inst. 1244-58 (2009), Wang et al., 14 Gastroenterology 524-31 (2008), Huang et al., 52 Digestive Dis. & Sci. 2287-91 (2007), and Muller et al., 363 Lancet 1283-85 (2004). The current MCAM study also confirmed significant hypermethylation of several other previously reported CRC methylation markers in CRCs relative to control NCs (such as RASSF2 and vimentin; FIG. 7, see Supplementary Materials and Methods above). However, unlike SFRP2, these loci demonstrated overlap in methylation levels between CRCs and control NCs in our study, and were therefore not included among the aforementioned 169 loci.

Example 2

Individual Qualitative Validation of Prioritized Targets in a Pilot Pooled Cohort Twenty of the 169 candidate CRC-specific methylation target loci were prioritized for further individual validation based on having shown the largest differences between CRCs and control NCs and the smallest intra-group variance in array-based methylation levels (FIG. 8, see Supplementary Materials and Methods above). These 20 loci were then analyzed by qualitative MSP, using pooled DNA specimens for CRCs and control NCs that had been studied in microarray scanning experiments. Specimens were pooled to avoid exhaustion of limited clinical DNA resources. It was reasoned that the previous and subsequent non-pooled analyses (i.e., microarray and qMSP assays) would eliminate false-positive findings caused by sample pooling (e.g., massive hypermethylation occurring in only a minority of CRCs). Hypermethylation in pooled CRCs versus pooled control NCs was observed at 16 of the 20 analyzed loci: SFRP2, visual system homeobox 2 (VSX2), BEN domain containing 4 (BEND4), ALX homeobox 3 (ALX3), neuronal pentraxin I (NPTX1), glucagon-like peptide 1 receptor (GLP1R), homer homolog 2 (HOMER2), gap junction protein, gamma 1 (GJC1), dedicator of biomarkersis 8 (DOCK8), nonmetastatic cells 4 (NME4), zinc finger protein 583 (ZNF583), transmembrane protein 42 (TMEM42), tubulin tyrosine ligase-like family, member 12 (TTLL12), miR-34b, and MDFI (FIG. 8). The miR-34b locus flanks the region, that is, proximal to the BTG4 gene transcriptional start site and is hypermethylated in ~90% of primary CRCs. See Toyota et al., 68 Cancer Res. 4123-32 (2008).

Example 2

Quantitative Methylation Assays of Validated Targets in a Larger Cohort

Methylation of the qualitatively validated CRC-specific methylation targets was then assessed in a larger cohort using a quantitative methodology, qMSP. Two loci were eliminated before performing qMSP: MDFI, for failure to establish a successful qMSP assay and SFRP2, for having already been established as a CRC detection marker. See Nagasaka et al., 101 J. Nat. Cancer Inst. 1244-58 (2009), Wang et al., 14 Gastroenterology 524-31 (2008), Huang et al., 52 Digestive Dis. & Sci. 2287-91 (2007), and Muller et al., 363 Lancet 1283-85 (2004). The 14 qMSP-tested loci comprised VSX2, BEND4, ALX3, NPTX1, GLP1R, HOMER2, GJC1, DOCK8, NME4, ZNF583, TMEM42, TTLL12, miR-34b, and BTG4 (i.e., the previously analyzed miR-34b-flanking region). The analyzed case-control cohort contained 113 specimens: 51 primary CRCs, nine adenomas, 26 control NCs from non-neoplasia patients, 19 NCs from CRC patients (CRC-NCs), and nine NCs from colon neoplasia-free cases who were younger than 40 years of age (young control NCs). The control NCs were analyzed as a base control group representing the target population for average-risk CRC screening. Case demographic data are given in FIG. 4. There were no significant differences in case age, a well-established non-neoplastic methylation promoting factor, between any groups except for the young control NCs.

Figure 2:
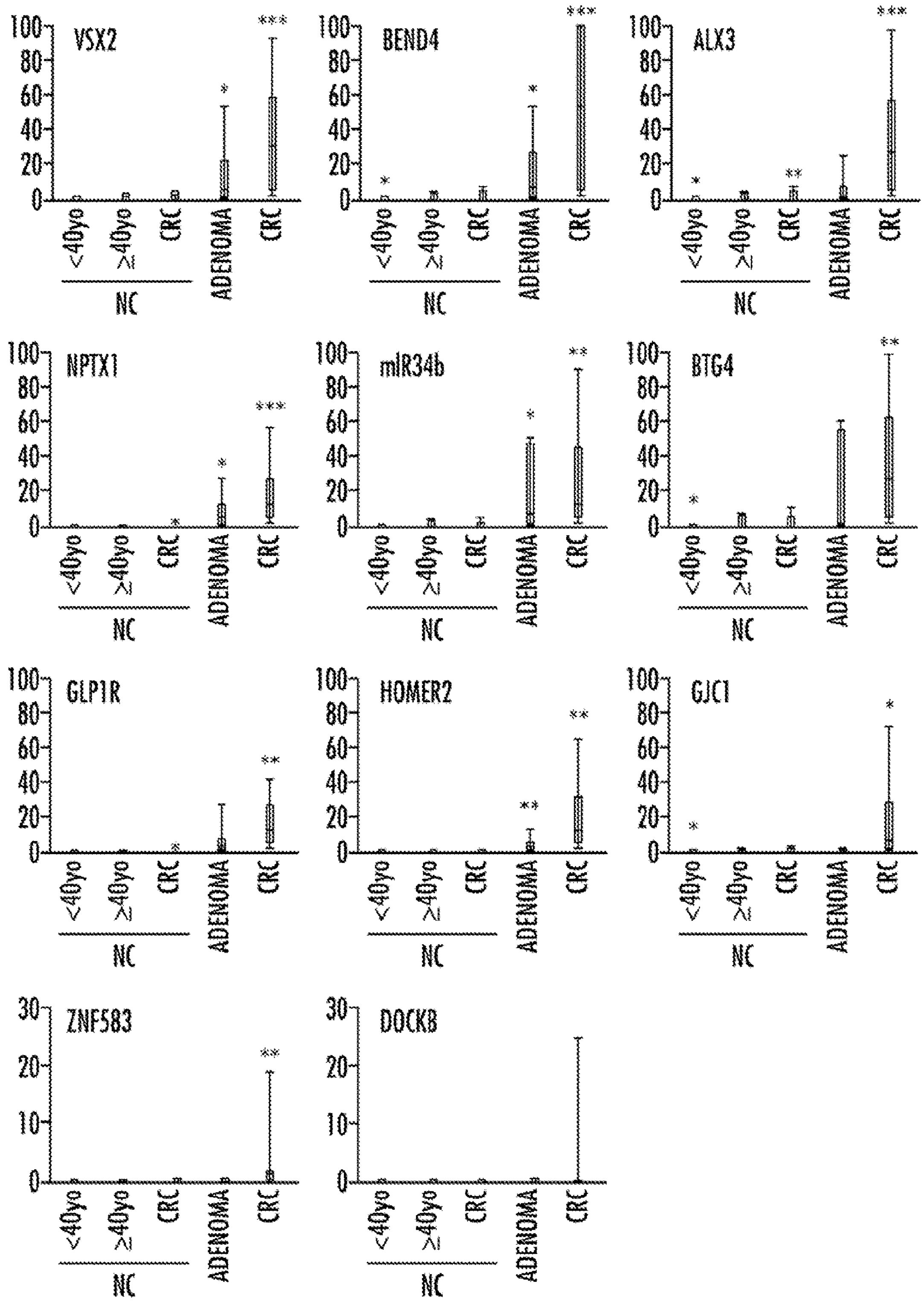
FIG. 2 shows loci percent methylation ratio (PMR) for neoplastic and non-neoplastic colonic tissues. The box plots represent the quantitative methylation-specific PCR (qMSP) results of 51 colorectal cancers (CRCs) and nine adenomas, and 53 non-neoplastic colonic mucosal tissues (NCs, eight young control NCs, 26 control NCs, and 19 CRC-NCs). The Y-axis represents PMR value. Data on 11 loci that demonstrated methylation in at least one of the neoplastic tissues are shown. Median (bar), 25-75 percentile range (box), and 10-90 percentile range (whisker) of all informative specimens are displayed for each tissue category. Single-, double-, and triple asterisks indicate significant difference from control NCs at P level <0.05, <0.01, and $<1\times10^{-6}$, respectively.

All 14 tested loci demonstrated varying degrees of hypermethylation in CRCs by qMSP assays. Significant hypermethylation in CRCs relative to control NCs was observed at all tested loci except DOCK8, NME4, TMEM42, and TTLL12 (FIG. 2). These four loci demonstrated tumor-specific methylation in a minor subset of CRCs. NME4, TMEM42, and TTLL12 were methylated in <10% of the 51 CRCs, and methylation of these loci was observed only in CRCs that had been studied by MCAM. Thus, these three loci were eliminated from further analyses, leaving 11 loci for further study. No significant differences in methylation levels according to the gender, Dukes stage (AB versus CD), or microsatellite instability (MSI) status were observed at any of these 11 loci (data not shown). GJC1 was significantly more heavily methylated in proximal CRCs (median percent methylation, or PMR, 10.8%) than in distal CRCs (0.8%; PZ0.02). CIMP (C) CRCs demonstrated significantly higher PMR levels than did CIMP (K) CRCs at ALX3, NPTX1, BTG4, GLP1R, HOMER2, DOCK8, and GJC1, although the majority of CIMP (K) CRCs were hypermethylated at all of these loci except DOCK8 (data not shown). DOCK8 was methylated in only 11 (25.6%) of 43 CIMP (K) CRCs, in contrast to CIMP (C) CRCs (four of five, or 80%; Fisher's exact test, PZ0.03).

Significant hypermethylation in adenomas relative to control NCs was observed at BEND4, VSX2, NPTX1, miR-34b, and HOMER2 (FIG. 2). Only miR-34b was methylated at equal levels in CRCs and adenomas (median PMR 10.9 vs. 11.4% for CRCs versus adenomas respectively; P=0.76). Remaining four loci were methylated at lesser degrees in adenomas than in CRCs, but these differences were insignificant. Tumor demographic data analyses were not performed for adenomas.

Figure 11:
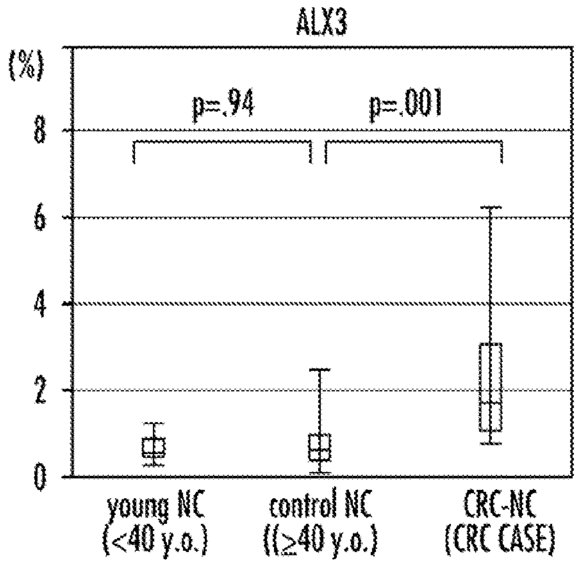
FIG. 11 shows the ALX3 methylation status for non-neoplastic colonic tissues from CRC cases as well as neoplasia-free control cases. Median (bar), 25-75 percentile range (box), and 10-90 percentile range (whisker) of all informative specimens are displayed for each tissue category. P-values were calculated by Mann-Whitney test.

Notably, ALX3 was mildly but significantly hypermethylated in CRC-NCs relative to control NCs (median PMR 1.6 vs. 0.6% for NC-CRCs versus control NCs respectively; P=0.001; FIG. 2 and FIG. 11, see Supplementary Materials and Methods above). ALX3 methylation in CRC-NCs showed no significant association with age or corresponding CRC stage (data not shown). Methylation levels of NC from all CRC-free cases (viz., control NCs and young control NCs) at BEND4, GJC1, VSX2, and miR-34b were significantly correlated JO with age (Spearman rank correlation R=0.55, 0.51, 0.39, and 0.38 respectively; P<0.05). However, differences between older and younger control NCs were small: median PMRs for old versus young NCs were 0.3 vs. 0.0%, 0.1 vs. 0.0%, 0.3 vs. 0.0%, and 1.4 vs. 0.6%, for BEND4, GJC1, VSX2, and miR-34b respectively. These differences were smaller than those reported for classic age-dependent hypermethylation targets (e.g., N33 and estrogen receptor a (ESR1); see Ahuja et al., 58 Cancer Res. 5489-94 (1998), and Issa et al., 7 Nat. Gen. 536-40 (1994)). Association between gender and gene methylation was not assessed due to the small number of female control NC cases studied (n=2).

Example 3

Evaluation of Methylated Loci as Colonic Neoplasia Markers

Figure 3A:
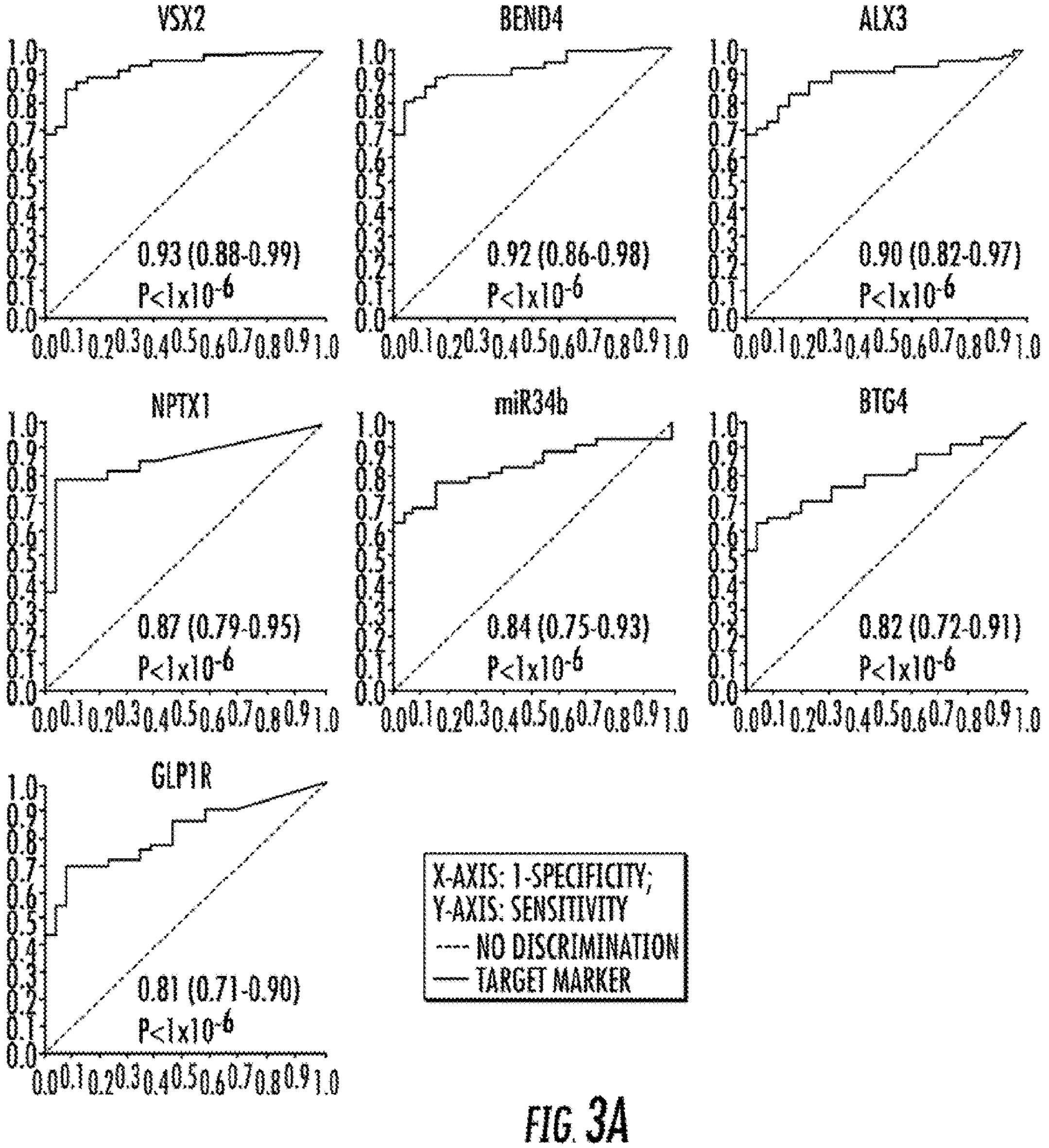
In FIG. 3A, ROC curves representing the distinction of CRCs from control NC are shown for the seven loci demonstrating area under ROC (AUROC) values >0.8. Mean and 95% confidence interval (CI) of AUROC as well as P value are shown in each panel.
Figure 3B:
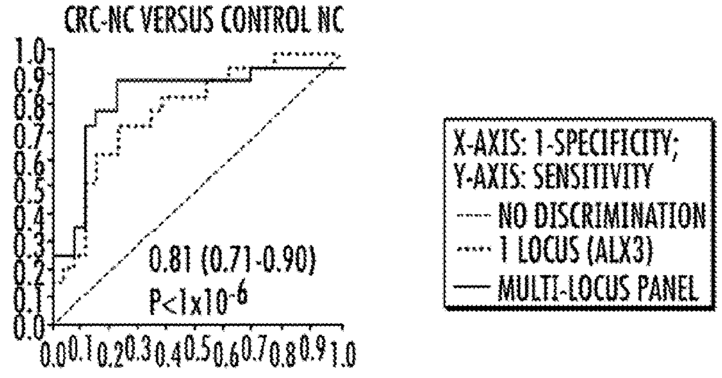
In FIG. 3B, ROC curves based on multi-loci diagnostic panels are shown for the distinction of CRCs from control NCs. Gray solid line and black solid line correspond to the profiles for best single locus (ALX3) and the multilocus panels (ALX3, ZNF583, miR-34b, and VSX2), respectively.

The 11 CRC-specific methylation targets were next tested for their abilities to distinguish colonic neoplasias from control NCs by employing ROC curve analysis. Methylation levels at all loci significantly distinguished CRCs from control NCs (P<0.05; FIG. 5). VSX2 achieved the highest discriminative accuracy (AUROC, 92.3, 83.3% sensitivity and 92.3% specificity; FIG. 3A). BEND4, ALX3, NPTX1, miR-34b, BTG4, and GLP1R also achieved particularly high diagnostic accuracy (AUROC>0.8, $P<1\times10^{-6}$; FIG. 3A). There was no statistically significant difference in AUROC between discrimination of Dukes AB versus Dukes CD CRCs from control NCs for all but one locus: ALX3 discriminated Dukes AB CRCs significantly better than Dukes CD CRCs (P<0.03; FIG. 5). Five loci significantly distinguished adenomas from control NCs: VSX2, BEND4, NPTX1, miR-34b, and HOMER2 (P<0.05; FIG. 5), despite our relatively small adenoma cohort size (n=9). BTG4 also demonstrated weak discriminative capacity in this regard (P=0.09). ALX3 was capable of significantly distinguishing CRC-NCs from control NCs ($P=5.1\times10^{-5}$; FIG. 5). ZNF583 and BEND4 exerted similar significant discriminative abilities (P<0.05), but the lower 95% confidence limit for their AUROCs did not exceed 0.5. Age did not significantly discriminate any diseased tissue classes from control NCs, as expected from the age-matched study enrollment strategy (data not shown). The use of a multilocus methylation panel improved the discrimination of CRC-NCs from control. NCs (AUROC 0.83; 95% CI 0.69-0.92) relative to the best-performing single locus (ALX3), although this improvement was insignificant (FIG. 3B). The loci included in this multilocus panel were ALX3, ZNF583, miR-34b, and VSX2. The use of multilocus methylation panels did not improve the discrimination of CRCs from NCs relative to the best-performing single locus (VSX2; data not shown).

Example 4

Evaluation of Methylation Biomarkers in Stool Specimens

Figure 12A:
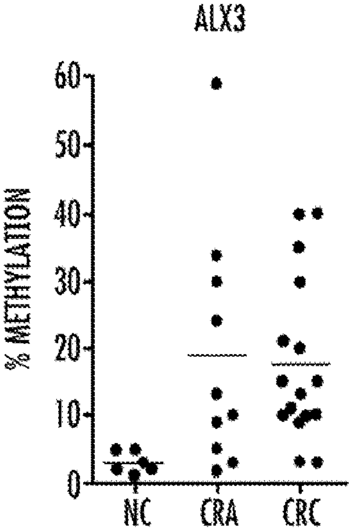
FIG. 12A shows the bisulfate pyrosequencing results of ALX3 in stool samples from CRC and CRA patients, and subjects without colonic lesions (NC).
Figure 12B:
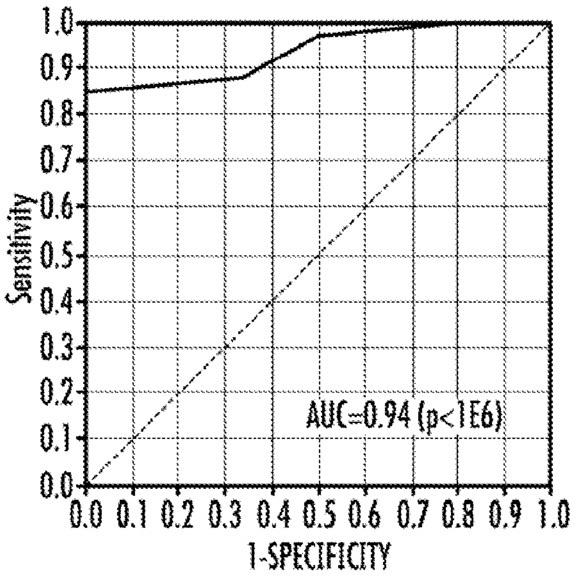
FIG. 12B shows the ROC (receiver-operating characteristics) curves for ALX3 in subjects with colorectal neoplasia (CRA and CRC) vs. subjects without any colonic lesions.

To determine whether methylation biomarkers identified in primary tumors are also useful in fecal DNA-based diagnosis, feces was collected and DNA was analyzed from 54 cases comprising 27 colorectal cancer (CRC), 21 colorectal adenoma (CRA) and 6 non-neoplastic control subjects (NC). Using quantitative bisulfate pyrosequencing, the performance of the novel methylation biomarker ALX3 was evaluated in stool DNA from CRC and CRA patients vs. NCs. As shown in FIG. 12A, stool methylation level was significantly higher in CRA and CRC patients than in healthy controls (t-test $p<0.05$ for both comparisons). The performance of this marker in diagnosing patients with advanced colorectal neoplasis (i.e., both CRA and CRC) is extremely high (AUROC, 0.94; FIG. 12B). Overall, these results reinforce the robustness and capability of the present approach to identify reliable and accurate methylation biomarkers for the early detection of colorectal neoplasia.

Example 5

Evaluation of Serum Methylation Biomarkers

Figure 13A:
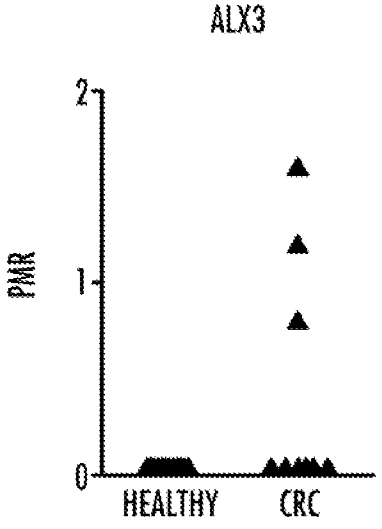
FIG. 13A shows the methylation of ALX3 and FIG. 13B shows the methylation of miR-34b in serum samples. The PMR (percentage or methylated reference) measured by MethyLight is plotted for serum samples from 10 healthy individuals and 9 CRC patients. Methylation was undetectable in all healthy control subjects' serums for both loci.
Figure 13B:
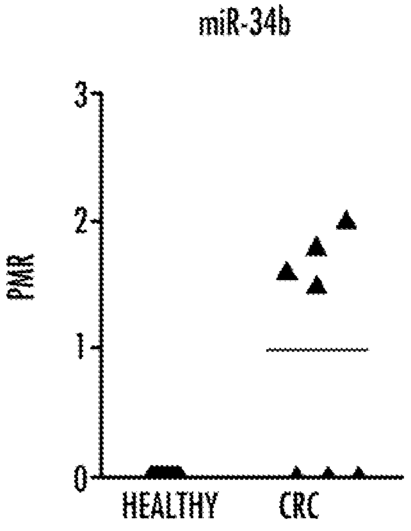

The performance of two methylation biomarkers, ALX3 and miR-34b, identified in a preliminary cohort of plasma samples from CRC patients (n=9) and healthy subject (n=10) was analyzed. DNA was extracted from 1 ml of serum, bisulfite conversion was performed, and methylation was analyzed using MethyLight that detects densely methylated DNA molecules in a sequence-specific fashion. Methylated DNA molecules were detected at both ALX3 and miR-34b in a subset of CRC patients' serum (FIG. 13). In contrast, no methylation was detected at ALX3 or miR-34b in any of the healthy subjects' serum. This experiment establishes the feasibility of detecting methylated alleles of ALX and miR-34b as plasma-based potential biomarkers for diagnosing CRC patients. Due to the small number of the cohort size, AUROC was no assessed.

Discussion

This unbiased genome-wide methylomics scan identified 169 candidate hypermethylation targets in human primary CRCs. The validity of the method was supported by finding significant hypermethylation of previously reported genes undergoing hypermethylation in CRC, including SFRP2. See Nagasaka et al., 101 J. Nat. Cancer Inst. 1244-58 (2009); Huang et al., 52 Digestive Dis. & Sci. 2287-91 (2007); and Muller et al., 363 Lancet 1283-85 (2004). Individual qMSP assessment of systematically prioritized loci validated frequent hypermethylation in primary CRCs at 11 loci: VSX2, NPTX1, BEND4, ALX3, miR-34b, BTG4, GLP1R, HOMER2, GJC1, DOCK8, and ZNF583. Infrequent but neoplasiaspecific methylation was observed at three additional loci: NME4, TTLL12, and TMEM42. Hypermethylation at each of these 11 loci effectively discriminated CRCs from colonic mucosae of age-matched neoplasia-free cases (i.e., control NCs). Most of these loci exhibited high discriminative accuracy (i.e. AUROC>0.8 and $P<1\times10^{-6}$), with VSX2 performing the best (AUROC=0.93). Methylation levels of VSX2, NPTX1, BEND4, miR-34b, and HOMER2 also significantly differentiated adenomas from control NCs (AUROC 0.74-0.83) and may constitute ideal markers for early-stage disease detection and/or risk stratification. The observed AUROC values for CRC and adenoma discrimination were very high even under the current study conditions (i.e., use of age-matched control cases and lack of tumor cell enrichment by microdissection, both of which reduce methylation-based discriminative accuracy).

It is also notable that CRC cases, regardless of their CIMP status, were distinguished from age-matched neoplasia-free cases based on hypermethylation of normeoplastic colonic mucosae at certain loci (such as ALX3). This finding is reminiscent of recent reports showing that CRC-associated hypermethylation target loci are mildly hypermethylated in non-neoplastic colonic mucosae from colonic neoplasia patients. See Worthley et al., 29 Oncogene 1653-62 (2010); Ahlquist et al., 7 Mol. Cancer 94 (2008); Belshaw et al., 99 Br. J. Cancer 136-42 (2008); Menigatti et al., 17 Oncology Reports 1421-27 (2007). However, in these published reports, differential methylation of normeoplastic mucosae was CIMP (+) neoplasia case-specific, or based on data from non-age-matched subjects. The present findings in non-neoplastic mucosae support the notion that CRC-associated hypermethylation initiates at an early, non-neoplastic stage, representing a widespread 'field defect.' See Belshaw et al., 31 Carcinogenesis 1158-63 (2010); Svrcek et al., 59 Gut 1516-26 (2010); Nosho et al., 137 Gastroenterology 1609-20 (2009); and Shen et al., 97 J. Nat. Cancer Inst. 1330-38 (2005). These non-neoplastic mucosal methylation events should be clinically translatable into CRC risk prediction, by non-neoplastic colonic or rectal mucosa as an analytic substrate. Moreover, CRC detection markers whose CRC-associated hypermethylation initiates at non-neoplastic stage may perform better in stool DNA-based tests than in primary tissue DNAbased tests, since stool DNA is derived from both nonneoplastic and neoplastic colonic mucosal cells.

The current MCAM study also detected CRC-associated hypermethylation of multiple previously published CRC-specific methylation markers, including the most extensively studied methylation marker to date, vimentin. See Li et al., 27 Nat. Biotech. 858-63 (2009); Baek et al., 52 Dis. Colon and Rectum 1452-63 (2009); Ahlquist et al., 149 Ann. Internal Med. 441-50 (2008); Itzkowitz et al., 5 Clin. Gastroenterology & Hepatology 111-17 (2007); Chen et al., 97 J. Nat. Cancer Inst. 1124-32 (2005). However, these markers, except for SFRP2, demonstrated methylation overlap between CRCs and NCs in the MCAM tissue cohort, and thus did not satisfy the selection criteria. Estecio et al. (2007) also performed MCAM on CRCs mainly focusing on CIMP class-based profiling, and reported hypermethylation of BARHL1 and RSH1. Estecio et al., 17 Genome Res. 1529-36 (2007). The present MCAM study verified significant CRC-associated hypermethylation of BARHL1, but not of RSHL1. Selection criteria was designed to eliminate CRC-associated hypermethylation targets that were also moderately methylated in nonneoplastic colonic mucosae of neoplasia-free cases, since they would not be anticipated to perform well as stool biomarkers, due to normal DNA contamination in stool DNA. As proof-of-principle of the success of the strategy, the current candidates did not include previously reported targets exhibiting this type of methylation (e.g., SST and CAV1, which were previously identified, Mod et al., 131 Gastroenterology 797-808 (2006)).

The present study represents the first report of neoplasia-associated hypermethylation of VSX2, BEND4, GL1R, HOMER2, GJC1, ZNF583, and NME4 in any tumor type. The loci detected in this study should be explored for use as broad-spectrum malignancy biomarkers, especially in blood-based detection studies.

In summary, this study has successfully applied an unbiased, extensive genome-wide scanning strategy to discover neoplasia-specific methylation targets in the colon, identifying 169 candidate novel loci. Quantitative PCR-based analysis of prioritized loci in a larger patient cohort revealed that methylation events at 11 loci were accurate in distinguishing both neoplastic and non-neoplastic colonic mucosae of colonic neoplasia patients from control colonic mucosae of neoplasia-free patients. Two of these genes have been implicated in endocrine-related carcinogenesis. Methylation at these loci now merits further investigation in studies of independent cohort validation, stool- and plasma-based CRC detection, as well as in the evaluation of non-neoplastic mucosa for field defects, potentially indicating increased CRC susceptibility.

REFERENCES

1. Ahlquist et al., 149 Ann. Internal Med. 441-50 (2008)
2. Ahlquist et al., 7 Mol. Cancer 94 (2008)
3. Ahuja et al., 58 Cancer Res. 5489-94 (1998)
4. Ausch et al., 55 Clin. Chem. 1559-63 (2009)
5. Ayala et al., 151 Endocrinology 4678-87 (2010)
6. Baek et al., 52 Dis. Colon and Rectum 1452-63 (2009)
7. Belshaw et al., 13 Cancer Epidemiol. Biomarkers Prev. 1495-1501 (2004)
8. Belshaw et al., 99 Br. J. Cancer 136-42 (2008)
9. Belshaw et al., 31 Carcinogenesis 1158-63 (2010)
10. Campos et al., 134 Endocrinology 2156-64 (1994)
11. Chen et al., 97 J. Nat. Cancer Inst. 1124-32 (2005)
12. DeLong et al., 44 Biometrics 837-45 (1988)
13. Dong et al., 387 Biochem. & Biophys. Res. Comm. 132-38 (2009)
14. Eads et al., 28 Nucl. Acids Res. E32 (2000)
15. Ebert et al., 131. Gastroenterology 1418-30 (2006)
16. Estecio et al., 17 Genome Res. 1529-36 (2007)
17. Fraga et al., 23 Trends in Gen. 413-18 (2007)
18. Glockner et al., 69 Cancer Res. 4691-99 (2009)
19. Gomes et al., 84 Biol. Reproduction 52-61 (2011)
20. Hadjiyanni et al., 53 Diabetologia 730-40 (2010)
21. Hagihara et al., 23 Oncogene 8705-10 (2004)
22. Hellebrekers et al., 15 Clin. Cancer Res. 3990-97 (2009)
23. Hiyama et al., 34 Exp. Lung Res. 373-90 (2008)
24. Hogan et al., 307 Mol. Cell. Endocrinology 19-24 (2009)
25. Huang et al., 52 Digestive Dis. & Sci. 2287-91 (2007)
26. Issa et al., 7 Nat. Gen. 536-40 (1994)
27. Itzkowitz et al., 287 Am. J. Physiol., Gastrointestinal & Liver Physiol. G7-17 (2004)
28. Itzkowitz et al., 11 Inflammatory Bowel Diseases 314-21 (2005)
29. Itzkowitz et al., 5 Clin. Gastroenterology & Hepatology 111-17 (2007)
30. Jemal et al., 58 Cancer J. For Clinicians 71-96 (2008)
31. Kahi et al., 135 Gastroenterology 380-99 (2008)
32. Kim et al., 4 PLoS One e6555 (2009)
33. Kim et al., 45 Genes, Chromosomes & Cancer 781-89 (2006)
34. Kozaki et al., 68 Cancer Res. 2094-2105 (2008)
35. Larsson et al., 27 Nat. Biotech. 1679-87 (2005)
36. Lee et al., 15 Clin. Cancer Res. 6185-91 (2009)
37. Lenhard et al., 3 Clin. Gastroenterol. Eiepatol. 142-49 (2005)
38. Li et al., 27 Nat. Biotech. 858-63 (2009)
39. Lin et al., Int. J. Cancer (2011) (in press)
40. Lujambio et al., 105 Proc. Natl. Acad. Sci. U.S.A. 13556-61 (2008)
41. Maher et al., 250 Ann. Surgery 729-37 (2009)
42. Melotte et al., 101 J. Natl. Cancer Inst. 916-27 (2009)
43. Menigatti et al., 17 Oncology Reports 1421-27 (2007)
44. Mori et al., 131 Gastroenterology 797-808 (2006)
45. Muller et al., 363 Lancet 1283-85 (2004)
46. Nagasaka et al., 101 J. Nat. Cancer Inst. 1244-58 (2009)
47. Nosho et al., 137 Gastroenterology 1609-20 (2009)
48. Ogawa et al., 21 Diseases of the Esophagus 288-97 (2008)
49. Ongenaert et al., 1 Bmc Medical Genomics 57 (2008)
50. Shen et al., 97 J. Nat. Cancer Inst. 1330-38 (2005)
51. Svrcek et al., 59 Gut 1516-26 (2010)
52. Takahashi et al., 28 Int. J. Oncology 321-28 (2006)
53. Tanzer et al., 5 PLoS One e9061 (2010)
54. Toyota et al., 68 Cancer Res. 4123-32 (2008)
55. Uhlmann et al., 23 Electrophoresis 4072-79 (2002)
56. Wang et al., 14 Gastroenterology 524-31 (2008)
57. Weisenberger et al., 38 787-93 (2006)
58. Wettenhall et al., 20 Bioinformatics 3705-06 (2004)
59. Wimmer et al., 33 Genes, Chromosomes & Cancer 285-94 (2002)
60. Worthley et al., 29 Oncogene 1653-62 (2010)
61. Xu et al., 56 Diabetes 1551-58 (2007)
62. Yang et al., 18 Biomarkers & Prev. 3000-07 (2009)
63. Yasuhara et al., 79 Biol. Reproduction 432-41 (2008)
64. Zou et al., 16 Cancer Epidemiol. Biomarkers Prev. 2686-96 (2007)

We claim:

1. A diagnostic kit for determining colorectal cancer (CRC) status in a patient comprising:

a substrate for collecting a biological sample from the patient; and primers and probes for performing real-time quantitative methylation-specific polymerase chain reaction on DNA obtained from a biological sample from the patient to amplify the following panel of genes ALX, GJC1, VSX2, NPTX1, BEND4, miR34b and HOMER2, wherein the primers and probes comprise SEQ ID NOS: 1-3 (ALX3), SEQ ID NOS: 51-53 (GJC1), SEQ ID NOS: 45-47 (VSX2), SEQ ID NOS: 31-33 (NPTX1), SEQ ID NOS: 48-50 (BEND4), SEQ ID NOS: 25-27 (miR34b), and SEQ ID NOS: 19-21 (HOMER2).

2. A method for identifying colorectal cancer in a patient comprising the steps of:

a. performing real-time quantitative methylation-specific polymerase chain reaction on DNA obtained from a biological sample from the patient using primers and probes to amplify the following panel of genes ALX3, GJC1, VSX2, NPTX1, BEND4, miR34b and HOMER2, wherein the primers and probes comprise SEQ ID NOS: 1-3 (ALX3), SEQ ID NOS: 51-53 (GJC1), SEQ ID NOS: 45-47 (VSX2), SEQ ID NOS: 31-33 (NPTX1), SEQ ID NOS: 48-50 (BEND4), SEQ ID NOS: 25-27 (miR34b), and SEQ ID NOS: 19-21 (HOMER2);

b. determining a methylation level of each of the genes in the panel;

c. comparing the methylation level of each of the genes in the panel to a methylation level of each of the genes of the same panel in a control; and d. identifying the patient as having colorectal cancer when a combined methylation value of the panel of genes from the biological sample is increased relative to a combined methylation value of the panel of genes in the control, or identifying the patient as not having colorectal cancer when a combined methylation value of the panel of genes from the biological sample is not increased relative to a combined methylation value of the panel of genes in the control.

3. The method of claim 2, wherein the sample is a stool, blood or serum sample.

4. The method of claim 2, wherein the sample is a stool sample.

5. The method of claim 2, wherein the sample is a serum sample.

* * * * *